(12) United States Patent
Davison et al.

(10) Patent No.: US 6,855,143 B2
(45) Date of Patent: Feb. 15, 2005

(54) ELECTROSURGICAL SYSTEMS AND METHODS FOR RECANALIZATION OF OCCLUDED BODY LUMENS

(75) Inventors: Paul O. Davison, Montara, CA (US); Jean Woloszko, Mountain View, CA (US)

(73) Assignee: Arthrocare Corporation, Sunnyvale, CA (US)

(*) Notice: Subject to any disclaimer, the term of this patent is extended or adjusted under 35 U.S.C. 154(b) by 0 days.

(21) Appl. No.: 09/735,426

(22) Filed: Dec. 12, 2000

(65) Prior Publication Data

US 2001/0001314 A1 May 17, 2001

Related U.S. Application Data

(63) Continuation-in-part of application No. 09/062,869, filed on Apr. 20, 1998, now Pat. No. 6,572,423, and a continuation-in-part of application No. 08/874,173, filed on Jun. 13, 1997, now Pat. No. 6,179,824, and a continuation-in-part of application No. 09/002,315, filed on Jan. 2, 1998, now Pat. No. 6,183,469.
(60) Provisional application No. 60/057,691, filed on Aug. 27, 1997, and provisional application No. 60/203,443, filed on May 10, 2000.

(51) Int. Cl.$^7$ ................................................ A61B 18/14
(52) U.S. Cl. .......................... 606/41; 606/45; 606/48; 607/99
(58) Field of Search ........................ 606/41, 49; 607/99

(56) References Cited

U.S. PATENT DOCUMENTS

| | | |
|---|---|---|
| 2,056,377 A | 10/1939 | Wappler |
| 3,815,604 A | 6/1974 | OMalley et al. |
| 3,828,780 A | 8/1974 | Morrison, Jr. et al. |
| 3,901,242 A | 8/1975 | Storz |
| 3,920,021 A | 11/1975 | Hiltebrandt |
| 3,939,839 A | 2/1976 | Curtiss |
| 3,970,088 A | 7/1976 | Morrison |

(List continued on next page.)

FOREIGN PATENT DOCUMENTS

| | | | |
|---|---|---|---|
| DE | 3930451 | 3/1991 | ........... A61B/17/39 |
| DE | 29609350 | 5/1996 | |

(List continued on next page.)

OTHER PUBLICATIONS

Pearce, John A. (1986) *Electrosurgery*, pp. 17, 69–75, 87, John Wiley & Sons, New York.

(List continued on next page.)

*Primary Examiner*—Lee S. Cohen
(74) *Attorney, Agent, or Firm*—John T. Raffle; Richard R. Batt

(57) ABSTRACT

The present invention comprises electrosurgical apparatus and methods for maintaining patency in body passages subject to occlusion by invasive tissue growth. The apparatus includes an electrode support disposed at a shaft distal end having at least one active electrode arranged thereon, and at least one return electrode proximal to the at least one active electrode. In one embodiment, a plurality of active electrodes each comprising a curved wire loop portion are sealed within a distal portion of the electrode support. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue in-growth in or around stents anchored therein.

36 Claims, 50 Drawing Sheets

U.S. PATENT DOCUMENTS

| | | |
|---|---|---|
| 4,040,426 A | 8/1977 | Morrison, Jr. |
| 4,043,342 A | 8/1977 | Morrison, Jr. |
| 4,060,087 A | 11/1977 | Hiltebrandt |
| 4,074,718 A | 2/1978 | Morrison, Jr. |
| 4,092,986 A | 6/1978 | Schneiderman |
| 4,116,198 A | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,582,056 A | 4/1986 | McCorkle, Jr. |
| 4,582,057 A | 4/1986 | Auth |
| 4,590,934 A | 5/1986 | Malis et al. |
| 4,593,691 A | 6/1986 | Lindstrom et al. |
| 4,641,649 A | 2/1987 | Walinsky |
| 4,643,186 A | 2/1987 | Rosen |
| 4,646,737 A | 3/1987 | Hussein |
| 4,654,024 A | 3/1987 | Crittendon |
| 4,658,817 A | 4/1987 | Hardy |
| 4,660,571 A | 4/1987 | Hess et al. |
| 4,672,962 A | 6/1987 | Hershenson |
| 4,674,499 A | 6/1987 | Pao |
| 4,682,596 A | 7/1987 | Bales et al. |
| 4,706,667 A | 11/1987 | Roos |
| 4,727,874 A | 3/1988 | Bowers et al. |
| 4,765,331 A | 8/1988 | Petruzzi et al. |
| 4,785,806 A | 11/1988 | Deckelbaum |
| 4,785,815 A | 11/1988 | Cohen |
| 4,785,823 A | 11/1988 | Eggers et al. |
| 4,799,479 A | 1/1989 | Spears |
| 4,805,616 A | 2/1989 | Pao |
| 4,823,791 A | 4/1989 | DAmelio et al. |
| 4,832,048 A | 5/1989 | Cohen |
| 4,860,743 A | 8/1989 | Abela |
| 4,907,586 A | 3/1990 | Bille |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,966,597 A | 10/1990 | Cosman |
| 4,967,765 A | 11/1990 | Turner et al. |
| 4,968,314 A | 11/1990 | Michaels |
| 4,976,709 A | 12/1990 | Sand |
| 4,976,711 A | 12/1990 | Parins et al. |
| 4,979,948 A | 12/1990 | Geddes et al. |
| 4,998,933 A | 3/1991 | Eggers et al. |
| 5,007,908 A | 4/1991 | Rydell |
| 5,009,656 A | 4/1991 | Reimels |
| 5,035,696 A | 7/1991 | Rydell |
| 5,041,109 A | 8/1991 | Abela |
| 5,047,026 A | 9/1991 | Rydell |
| 5,047,027 A | 9/1991 | Rydell |
| 5,078,717 A | 1/1992 | Parins et al. |
| 5,078,736 A | 1/1992 | Behl |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,093,877 A | 3/1992 | Aita |
| 5,098,431 A | 3/1992 | Rydell |
| 5,099,840 A | 3/1992 | Goble |
| 5,102,410 A | 4/1992 | Dressel |
| 5,108,391 A | 4/1992 | Flachenecker et al. |
| RE33,925 E * | 5/1992 | Bales et al. .................. 606/48 |
| 5,112,330 A | 5/1992 | Nishigaki et al. |
| 5,122,138 A | 6/1992 | Manwaring |
| 5,125,924 A | 6/1992 | Rudko |
| 5,125,926 A | 6/1992 | Rudko |
| 5,125,928 A * | 6/1992 | Parins et al. .................. 606/48 |
| 5,137,530 A | 8/1992 | Sand |
| 5,140,987 A | 8/1992 | Schuger |
| 5,152,759 A | 10/1992 | Parel |
| 5,156,151 A | 10/1992 | Imran |
| 5,167,659 A | 12/1992 | Ohtomo et al. |
| 5,171,311 A | 12/1992 | Rydell et al. |
| 5,178,618 A | 1/1993 | Kandarpa |
| 5,178,620 A | 1/1993 | Eggers et al. |
| 5,188,635 A | 2/1993 | Radtke |
| 5,190,517 A | 3/1993 | Zieve et al. |
| 5,190,540 A | 3/1993 | Lee |
| 5,192,280 A | 3/1993 | Parins |
| 5,195,959 A | 3/1993 | Smith |
| 5,196,006 A | 3/1993 | Klopotek |
| 5,197,466 A | 3/1993 | Marchosky et al. |
| 5,197,963 A | 3/1993 | Parins |
| 5,200,604 A | 4/1993 | Rudko |
| 5,207,675 A | 5/1993 | Canady |
| 5,217,455 A | 6/1993 | Tan |
| 5,217,457 A | 6/1993 | Delahuerga et al. |
| 5,217,459 A | 6/1993 | Kamerling |
| 5,222,938 A | 6/1993 | Behl |
| 5,224,953 A | 7/1993 | Morgentaler |
| 5,230,334 A | 7/1993 | Klopotek |
| 5,242,386 A | 9/1993 | Holzer |
| 5,246,438 A | 9/1993 | Langberg |
| 5,250,045 A | 10/1993 | Bohley |
| 5,261,410 A | 11/1993 | Alfano |
| 5,263,951 A | 11/1993 | Spears |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,279,299 A | 1/1994 | Imran |
| 5,281,211 A | 1/1994 | Parel |
| 5,282,797 A | 2/1994 | Chess |
| 5,290,273 A | 3/1994 | Tan |
| 5,290,282 A | 3/1994 | Casscells |
| 5,292,321 A | 3/1994 | Lee |
| 5,293,868 A | 3/1994 | Nardella |
| 5,300,069 A | 4/1994 | Hunsberger et al. |
| 5,304,170 A | 4/1994 | Green |
| 5,306,238 A | 4/1994 | Fleenor |
| 5,312,395 A | 5/1994 | Tan |
| 5,312,400 A | 5/1994 | Bales et al. |
| 5,314,406 A | 5/1994 | Arias et al. |
| 5,318,525 A | 6/1994 | West |
| 5,324,254 A | 6/1994 | Phillips |
| 5,330,470 A | 7/1994 | Hagen |
| 5,330,496 A | 7/1994 | Alferness |
| 5,334,140 A | 8/1994 | Philips |
| 5,334,190 A | 8/1994 | Seiler |
| 5,335,668 A | 8/1994 | Nardella |
| 5,336,217 A | 8/1994 | Buys |
| 5,342,357 A | 8/1994 | Nardella |
| 5,348,554 A | 9/1994 | Imran |
| 5,366,443 A | 11/1994 | Eggers et al. |
| 5,370,642 A | 12/1994 | Keller |
| 5,370,644 A | 12/1994 | Langberg |
| 5,370,675 A | 12/1994 | Edwards et al. |
| 5,374,265 A | 12/1994 | Sand |
| 5,375,588 A | 12/1994 | Yoon |
| 5,380,277 A | 1/1995 | Phillips |

| Patent No. | Date | Inventor |
|---|---|---|
| 5,380,316 A | 1/1995 | Aita |
| 5,383,876 A | 1/1995 | Nardella |
| 5,383,917 A | 1/1995 | Desai et al. |
| 5,389,096 A | 2/1995 | Aita |
| 5,395,312 A | 3/1995 | Desai |
| 5,400,428 A | 3/1995 | Grace |
| 5,403,311 A | 4/1995 | Abele |
| 5,417,687 A | 5/1995 | Nardella et al. |
| 5,419,767 A | 5/1995 | Eggers et al. |
| 5,423,803 A | 6/1995 | Tankovich |
| 5,423,806 A | 6/1995 | Dale |
| 5,423,810 A | 6/1995 | Goble et al. |
| 5,423,882 A | 6/1995 | Jackman et al. |
| 5,425,355 A | 6/1995 | Kulick |
| 5,429,144 A | 7/1995 | Wilk |
| 5,429,604 A | 7/1995 | Hammersmark |
| 5,433,708 A | 7/1995 | Nichols |
| 5,436,566 A | 7/1995 | Thompson et al. |
| 5,437,658 A | 8/1995 | Muller |
| 5,437,662 A | 8/1995 | Nardella |
| 5,438,302 A | 8/1995 | Goble |
| 5,441,499 A | 8/1995 | Fritzsch |
| 5,445,634 A | 8/1995 | Keller |
| 5,451,224 A | 9/1995 | Goble et al. |
| 5,454,809 A | 10/1995 | Janssen |
| 5,456,680 A | 10/1995 | Taylor |
| 5,462,544 A | 10/1995 | Sakesena |
| 5,464,404 A | 11/1995 | Abela |
| 5,484,433 A | 1/1996 | Taylor |
| 5,487,385 A | 1/1996 | Avitall |
| 5,496,312 A | 3/1996 | Klicek |
| 5,496,314 A | 3/1996 | Eggers |
| 5,496,317 A | 3/1996 | Goble et al. |
| 5,500,012 A | 3/1996 | Brucker |
| 5,505,725 A | 4/1996 | Samson |
| 5,507,771 A | 4/1996 | Gianturco |
| 5,514,128 A | 5/1996 | Hillsman |
| 5,514,130 A | 5/1996 | Baker |
| 5,540,712 A | 7/1996 | Kleshinski |
| 5,542,928 A | 8/1996 | Evans |
| 5,545,161 A | 8/1996 | Imran |
| 5,545,211 A | 8/1996 | An |
| 5,554,152 A | 9/1996 | Aita |
| 5,556,397 A | 9/1996 | Long et al. |
| 5,567,890 A | 10/1996 | Lindberg et al. |
| 5,569,242 A | 10/1996 | Lax et al. |
| 5,571,100 A | 11/1996 | Goble et al. |
| 5,571,169 A | 11/1996 | Plaia |
| 5,579,764 A | 12/1996 | Goldreyer |
| 5,584,872 A | 12/1996 | LaFontaine et al. |
| 5,591,159 A | 1/1997 | Taheri |
| 5,603,731 A | 2/1997 | Whitney |
| 5,607,421 A | 3/1997 | Jeevanandam |
| 5,609,151 A | 3/1997 | Mulier et al. |
| 5,620,438 A | 4/1997 | Amplatz |
| 5,626,576 A * | 5/1997 | Janssen .................. 606/41 |
| 5,633,578 A | 5/1997 | Eggers et al. |
| 5,643,251 A | 7/1997 | Hillsman |
| 5,643,255 A | 7/1997 | Organ |
| 5,647,869 A | 7/1997 | Goble et al. |
| 5,662,680 A | 9/1997 | Desai |
| 5,669,907 A | 9/1997 | Platt |
| 5,672,170 A | 9/1997 | Cho |
| 5,673,695 A | 10/1997 | McGee |
| 5,676,693 A | 10/1997 | LaFontaine et al. |
| 5,681,282 A | 10/1997 | Eggers et al. |
| 5,681,308 A | 10/1997 | Edwards |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,725,524 A | 3/1998 | Mulier et al. |
| 5,749,914 A | 5/1998 | Janssen |
| 5,766,153 A | 6/1998 | Eggers et al. |
| 5,766,192 A | 6/1998 | Zacca |
| 5,769,843 A | 6/1998 | Abela |
| 5,775,338 A | 7/1998 | Hastings |
| 5,807,384 A | 9/1998 | Mueller |
| 5,807,395 A | 9/1998 | Mulier et al. |
| 5,810,764 A | 9/1998 | Eggers et al. |
| 5,810,809 A | 9/1998 | Rydell |
| 5,817,013 A | 10/1998 | Ginn |
| 5,823,955 A | 10/1998 | Kuck |
| 5,836,868 A | 11/1998 | Ressemann |
| 5,840,059 A | 11/1998 | March |
| 5,843,019 A | 12/1998 | Eggers et al. |
| 5,860,951 A | 1/1999 | Eggers |
| 5,860,974 A | 1/1999 | Abele |
| 5,860,975 A | 1/1999 | Goble et al. |
| 5,871,469 A | 2/1999 | Eggers et al. |
| 5,873,855 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,893,885 A | 4/1999 | Webster, Jr. |
| 5,897,553 A | 4/1999 | Mulier et al. |
| 5,902,272 A | 5/1999 | Eggers et al. |
| 5,944,715 A | 8/1999 | Goble et al. |
| 6,004,319 A | 12/1999 | Goble et al. |
| 6,013,076 A | 1/2000 | Goble et al. |
| 6,015,406 A | 1/2000 | Goble et al. |
| 6,024,733 A | 2/2000 | Eggers et al. |
| 6,027,501 A | 2/2000 | Goble et al. |
| 6,039,734 A | 3/2000 | Goble et al. |
| 6,056,746 A * | 5/2000 | Goble et al. .................. 606/48 |
| 6,063,079 A | 5/2000 | Hovda et al. |
| 6,066,134 A | 5/2000 | Eggers et al. |
| 6,068,628 A | 5/2000 | Fanton et al. |
| 6,074,386 A | 6/2000 | Goble et al. |
| 6,090,106 A | 7/2000 | Goble et al. |
| 6,093,186 A | 7/2000 | Goble et al. |
| 6,102,046 A | 8/2000 | Weinstein et al. |
| 6,109,268 A | 8/2000 | Thapliyal et al. |
| 6,117,109 A | 9/2000 | Eggers et al. |
| 6,126,682 A | 10/2000 | Sharkey et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,161,543 A | 12/2000 | Cox |
| 6,168,593 B1 | 1/2001 | Sharkey et al. |
| 6,174,308 B1 * | 1/2001 | Goble et al. .................. 606/41 |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,224,592 B1 | 5/2001 | Eggers et al. |
| 6,228,081 B1 | 5/2001 | Goble |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,264,652 B1 | 7/2001 | Eggers et al. |
| 6,277,112 B1 | 8/2001 | Underwood et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,306,134 B1 | 10/2001 | Goble et al. |

| | | | |
|---|---|---|---|
| 6,312,408 | B1 | 11/2001 | Eggers et al. |
| 6,322,549 | B1 | 11/2001 | Eggers et al. |
| 6,355,032 | B1 | 3/2002 | Hovda et al. |
| 6,363,937 | B1 | 4/2002 | Hovda et al. |
| 6,379,351 | B1 | 4/2002 | Thapliyal et al. |
| 6,391,025 | B1 | 5/2002 | Weinstein et al. |
| 6,416,507 | B1 | 7/2002 | Eggers et al. |
| 6,416,508 | B1 | 7/2002 | Eggers et al. |
| 6,432,103 | B1 | 8/2002 | Ellsberry et al. |
| 6,530,922 | B2 | 3/2003 | Cosman |
| 6,602,248 | B1 | 8/2003 | Sharps et al. |
| 2002/0029036 | A1 | 3/2002 | Goble et al. |

FOREIGN PATENT DOCUMENTS

| | | | |
|---|---|---|---|
| DE | 19537084 | 4/1997 | |
| DE | 29619029 | 4/1997 | |
| EP | 0 703 461 | 3/1996 | G01R/27/02 |
| EP | 0553576 | 4/1996 | |
| EP | 0 740 926 A2 | 11/1996 | A61B/17/39 |
| EP | 0 754 437 | 1/1997 | A61B/17/39 |
| EP | 0515867 | 7/1999 | |
| EP | 0 694 290 | 11/2000 | A61B/18/04 |
| FR | 2313949 | 1/1977 | A61N/3/02 |
| GB | 2 308 979 | 7/1997 | A61B/17/36 |
| GB | 2 308 980 | 7/1997 | A61B/17/36 |
| GB | 2 308 981 | 7/1997 | A61B/17/36 |
| GB | 2 327 350 | 1/1999 | A61B/17/39 |
| GB | 2 327 351 | 1/1999 | A61B/17/39 |
| GB | 2 327 352 | 1/1999 | A61B/17/39 |
| JP | 57-57802 | 4/1982 | A61B/1/00 |
| JP | 57-117843 | 7/1982 | A61B/17/39 |
| WO | 90/03152 | 4/1990 | A61B/17/39 |
| WO | 90/07303 | 7/1990 | A61B/17/39 |
| WO | 92/21278 | 12/1992 | A61B/5/04 |
| WO | 93/13816 | 7/1993 | A61B/17/36 |
| WO | 93/20747 | 10/1993 | A61B/5/00 |
| WO | 94/04220 | 3/1994 | |
| WO | 94/08654 | 4/1994 | A61M/37/00 |
| WO | 94/14383 | 7/1994 | |
| WO | 95/34259 | 12/1995 | A61F/5/48 |
| WO | 96/00042 | 1/1996 | A61B/17/39 |
| WO | 96/35469 | 11/1996 | |
| WO | 96/39962 | 12/1996 | |
| WO | 96/39963 | 12/1996 | |
| WO | 96/39965 | 12/1996 | |
| WO | 97/00646 | 1/1997 | A61B/17/39 |
| WO | 97/00647 | 1/1997 | A61B/17/39 |
| WO | 97/24073 | 7/1997 | A61B/17/39 |
| WO | 97/24074 | 7/1997 | A61B/17/39 |
| WO | 97/24993 | 7/1997 | A61B/17/39 |
| WO | 97/24994 | 7/1997 | A61B/17/39 |
| WO | 97/25101 | 7/1997 | |
| WO | 97/34540 | 9/1997 | |
| WO | 97/44071 | 11/1997 | |
| WO | 97/48345 | 12/1997 | A61B/17/39 |
| WO | 97/48346 | 12/1997 | A61B/17/39 |
| WO | 98/07468 | 2/1998 | A61N/1/40 |
| WO | 98/17185 | 4/1998 | |
| WO | 98/17186 | 4/1998 | |
| WO | 98/19614 | 5/1998 | |
| WO | 98/23324 | 6/1998 | |
| WO | 98/27877 | 7/1998 | |
| WO | 98/27879 | 7/1998 | A61B/17/36 |
| WO | 98/27880 | 7/1998 | A61B/17/36 |
| WO | 98/30144 | 7/1998 | |
| WO | 98/38925 | 9/1998 | |
| WO | 98/39038 | 9/1998 | |
| WO | 99/51155 | 10/1999 | A61B/17/36 |
| WO | 99/51158 | 10/1999 | A61B/17/39 |

OTHER PUBLICATIONS

J.W. Ramsey et al. *Urological Research* vol. 13, pp. 99–102 (1985).

V.E. Elsasser et al. *Acta Medicotechnica* vol. 24, No. 4, pp. 129–134 (1976).

P.C. Nardella (1989) *SPIE* 1068:42–49 Radio Frequency Energy and Impedance Feedback.

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

Slager et al. *JACC* 5(6) :1382–6 (1985).

Olsen MD, Bipolar Laparoscopic Cholecstectomy Lecture (marked confidential), Oct. 7, 1991.

Codman & Shurtleff, Inc. "The Malis Bipolar Electrosurgical System CMC–III Instruction Manual" Jul. 1991.

Valley Forge's New Products CLINICA, 475, 5, Nov. 6, 1991.

Valley Forge Scientific Corp., "Summary of Safety and Effective Information from 510K, " 1991.

Codman and Shurtleff, Inc. "The Malis Bipolar Coagulating and Bipolar Cutting System CMC–II" brochure, early 1991.

L. Malis, "The Value of Irrigation During Bipolar Coagulation" See ARTC 21602, early Apr. 9, 1993.

L. Malis, "Excerpted from a seminar by Leonard I. Malis, M. D. at the 1995 American Association of Neurological Surgeons Meeting, " 1995.

L. Malis, "Electrosurgery, Technical Note, " *J. Neursurg.*, vol. 85, 970–975, 11/96.

Ian E. Shuman, "Bipolar Versus Monopolar Electrosurgery: Clinical Applications," *Dentistry Today*, vol. 20, No. 12, 12/01.

Protell et al., "Computer–Assisted Electrocoagulation: Bipolar v. Monopolar in the Treatment of Experimental Canine Gastric Ulcer Bleeding, " *Gastroenterology* vol. 80, No. 3, pp. 451–455.

Cook and Webster, "Therapeutic Medical Devices: Application and Design, " 1982.

Valleylab SSE2L Instruction Manual, Jan. 6, 1983.

Robert D. Tucker et al., "Demodulated Low Fequency Currents from Electrosurgical Procedures, " *Surgery, Gynecology and Obstetrics*, 159:39–43, 1984.

Lu, et al., "Electrical Thermal Angioplasty: Catheter Design Features, In Vitro Tissue Ablation Studies and In Vitro Experimental Findings, " *Am J. Cardiol* vol. 60, pp. 1117–1122.

Selikowitz & LaCourse, "Electric Current and Voltage Recordings on the Myocardium During Electrosurgical Procedures in Canines, " *Surgery, Gynecology & Obstetrics*, vol. 164, 219–224, Mar. 1987.

J. O'Malley, Schaum's Outline of Theory and Problems of Basic Circuit Analysis, McGraw–Hill, $2^{nd}$ Ed., 1992, pp. 3–5.

Arnaud Wattiez et al., "Electrosurgery in Operative Endoscopy, " Electrosurgical Effects, Blackwell Science, pp. 85–93, 1995.

Leslie A. Geddes, "Medical Device Accidents: With Illustrative Cases" CRC Press, 1998.

Wyeth, "Electrosurgical Unit" pp. 1181–1202.
C.P. Swain, et al., *Gut* vol. 25, pp. 1424–1431 (1984).
Piercey et al., *Gastroenterology* vol. 74(3), pp. 527–534 (1978).
A.K. Dobbie *Bio–Medical Engineering* vol. 4, pp. 206–216 (1969).
B. Lee et al. JACC vol. 13(5), pp. 1167–1175 (1989).
K. Barry et al. *American Heart Journal* vol. 117, pp. 332–341 (1982).
W. Honig *IEEE* pp. 58–65 (1975).
Jacob Kline, *Handbook of Biomedical Engineering*, Academic Press Inc., N.Y., pp. 98–113, 1988.
M.B. Dennis et al. "Evolution of Electrofulguration in Control of Bleeding of Experimental Gastric Ulcers, " Digestive Diseases and Sciences, vol. 24, No. 11, 845–848.
Letter from Department of Health to Jerry Malis dated Apr. 15, 1985.
Letter from Jerry Malis to FDA dated Jul. 25, 1985.
Letter from Department of Health to Jerry Malis dated Apr. 22, 1991.

Leonard Malis, "Instrumenation for Microvascular Neurosurgery" *Cerebrovascular Surgery*, vol. 1, 245–260, 1985.
Valleylab, Inc. "Valleylab Part No. 945 100 102 A" Surgistat Service Manual, 7/88.
Leonard I. Malis, "New Trends in Microsurgery and Applied Technology, " *Advanced Technology in Neurosurgery*, 1–16, 1988.
Regional myocardial blood flow and cardiac mechanics in dog hearts with $CO_2$ laser–induced intramyocardial revascularization, Basic Research in Cardiology 85:179–197 (1990) R. Hardy, F. James, R Millard and S. Kaplan.
Transventricular Revascularization by Laser, Lasers in Surgery and Medicine 2:187–198 (1982) M. Mirhoseini MD, Muckerheide, and Cayton RN.
Transmyocardial Laser Revascularization: A Review; J. Of Clinical Laser Medicine & Surgery V. 11, No. 1 1993 pp 15–19; M. Mirohoseini, MD, S. Shelgikar MD, M Cayton RN.

* cited by examiner

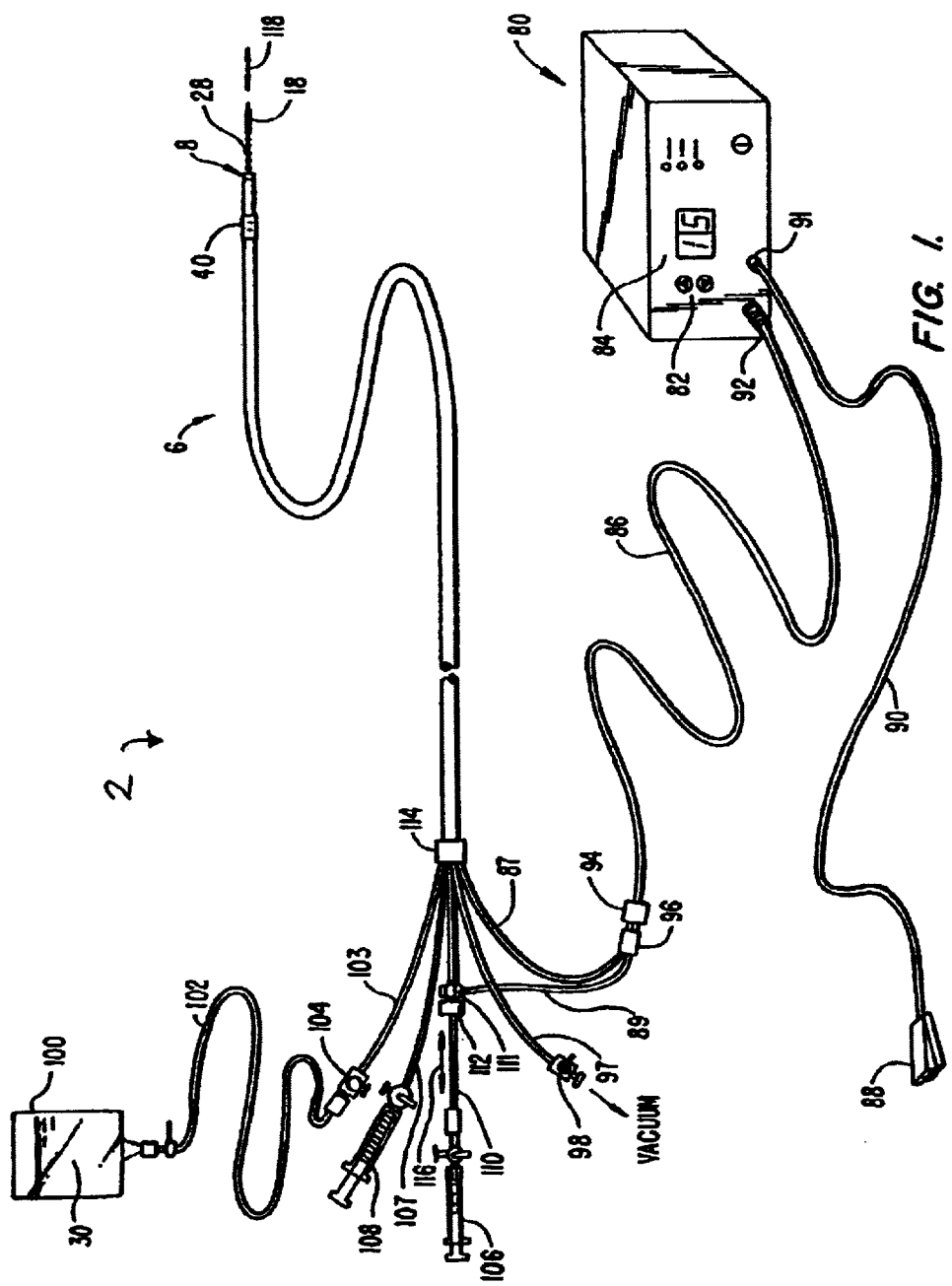

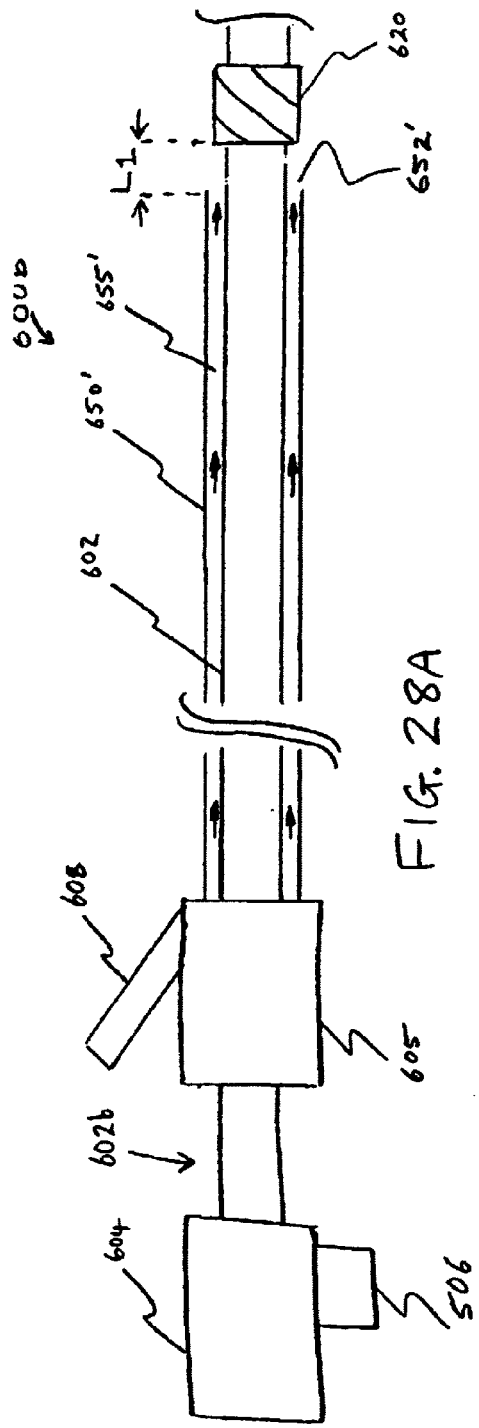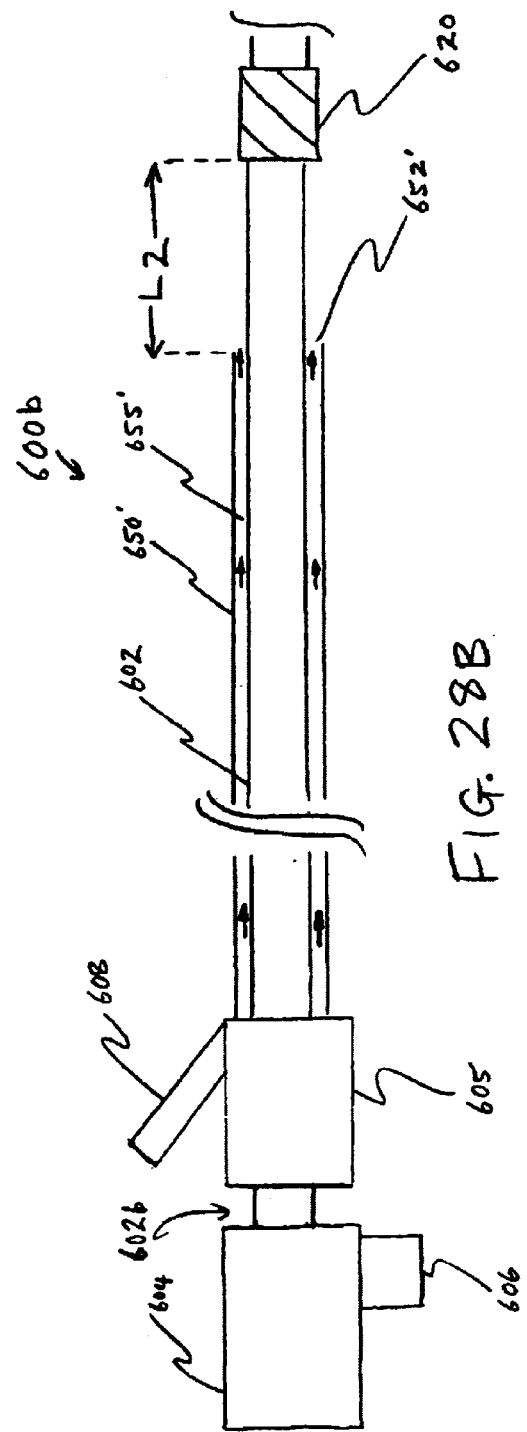

ELECTROSURGICAL SYSTEMS AND METHODS FOR RECANALIZATION OF OCCLUDED BODY LUMENS

CROSS-REFERENCE TO RELATED APPLICATIONS

The present application claims priority from Provisional Patent Application No. 60/203,443, filed May 10, 2000, which is a continuation-in-part of U.S. application Ser. No. 09/062,869, filed Apr. 20, 1998 U.S. Pat. No. 6,582,423 and U.S. application Ser. No. 08/874,173, filed Jun. 13, 1997 U.S. Pat. No. 6,179,824 and derives priority from U.S. application Ser. No. 09/002,315, filed Jan. 2, 1998 U.S. Pat. No. 6,183,469, which claims benefit of 60/057,691 filed Aug. 27, 1997, the complete disclosures of which are incorporated herein by reference for all purposes.

The present invention also claims the benefit of U.S. application Ser. Nos. 09/477,832 and 09/248,763 filed Jan. 5, 2000 and Feb. 12, 1999, respectively, the full disclosure of which is incorporated herein by reference for all purposes.

The present invention is further related to commonly assigned U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, Provisional Patent Application No. 60/075,059, filed on Feb. 18, 1998, U.S. patent application Ser. No. 09/010,382, filed Jan. 21, 1998, and U.S. patent application Ser. No. 09/032,375, Feb. 27, 1998, U.S. patent application Ser. Nos. 08/977,845, filed on Nov. 25, 1997, 08/942,580, filed on Oct. 2, 1997, 09/026,851, filed Feb. 20, 1998, U.S. application Ser. No. 08/753,227, filed on Nov. 22, 1996, U.S. application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to apparatus and methods for maintaining patency in body passages and more particularly to a catheter system capable of selectively ablating occlusive media within a body lumen. The present invention is particularly useful for the electrosurgical removal or ablation of invasive tissue growth or atheromatous material in or around an intraluminal prosthesis or stent anchored in the body lumen, whereby restenosis of the body lumen is reduced or eliminated.

When a patient is suffering from atherosclerosis, significant occlusions or blockages are formed on the interior wall of the artery. As a result of these occlusions, the organ or extremity to which blood is to be supplied is compromised and the patient may experience a myocardial infarction or stroke. In less severe cases, it is often sufficient to treat the symptoms with pharmaceuticals and lifestyle modification to lessen the underlying causes of the disease. In more severe cases, however, a coronary artery blockage can often be treated using endovascular techniques such as balloon angioplasty, atherectomy, laser or hot tip ablation, placement of stents, and the like.

Percutaneous transluminal balloon angioplasty (PTBA) has become a recognized method of reducing the occlusion of blood vessels. The procedure involves routing a catheter having an inflatable balloon at the distal end thereof through the vascular system until the balloon is positioned at the site of the stenotic lesion to be treated. The balloon is then inflated to compress the atherosclerotic plaque into the wall of the blood vessel, thus increasing the size of the opening and enhancing blood flow through the affected artery. However, this successful procedure is overshadowed by the occurrence of restenosis, a re-narrowing of the artery. Studies have shown that 30–40 percent of angioplasty patients experience restenosis within 3–6 months of the angioplasty procedure. When restenosis occurs, patients may be treated with cardiovascular medications, additional angioplasty procedures or bypass surgery.

Restenosis often occurs because the wall of the dilated artery tends to spring back to its original shape following deflation of the dilation balloon. Arterial stenting has been introduced as a solution to the recoil of the vessel wall. Arterial stenting involves the placement of an expandable coil spring or wire-mesh tube within the occluded artery to reopen the lumen of the blood vessel. One example of an arterial stent is disclosed in U.S. Pat. No. 4,739,792 to Julio Palmaz. The Palmaz device comprises an expandable wire-mesh graft or prosthesis which is mounted upon an inflatable balloon catheter. The catheter assembly, including the graft, is delivered to the occluded area and the balloon is then inflated to radially force the graft into contact with the occlusion. As the graft expands, the lumen of the blood vessel is opened and blood flow is restored. After complete expansion of the graft, the balloon catheter is deflated and removed, leaving behind the graft to buttress and prevent elastic recoil of the blood vessel wall.

Although this method is successful in preventing recoil of the vessel wall, restenosis will often still occur. Smooth muscle cells which form the vessel wall tend to proliferate and build-up in the newly stented area of the blood vessel. This cellular build-up may eventually become large enough to block the lumen of the blood vessel.

It has recently been determined that localized heating of the blood vessel wall may inhibit the proliferation of smooth muscle cells which are believed to cause restenosis. One example of localized blood vessel heating is disclosed in U.S. Pat. No. 4,799,479 to Spears. The Spears patent discloses an apparatus for angioplasty having an inflatable balloon catheter which is provided with a meshwork of electrical wires to supply heat to a vessel wall. Following balloon angioplasty, the external surface of the balloon is heated to fuse together disrupted tissue elements and to kill smooth muscle cells which are believed to lead to restenosis. Unfortunately, the Spears device does not adequately prevent the spontaneous elastic recoil of the arterial wall. Immediately following angioplasty the arterial wall begins to spring back to its original shape.

Thus stenting in and of itself is ineffective in preventing restenosis due to the occurrence of cellular proliferation. Likewise, balloon dilation in combination with localized heating does not adequately prevent restenosis since the vessel wall tends to spontaneously return to its original occluded shape.

Other techniques have recently been developed to help reduce incidences of restenosis. For example, procedures for irradiating the angioplasty site with UV light to reduce the proliferation of smooth muscle cells at the site have been disclosed. In addition, techniques have been disclosed for the controlled application of thermal and/or electrical energy directly to the stent by, for example, including resistive or inductive heating elements that may include radiofrequency electrodes within the stent. The radiofrequency energy is then applied to the stent to disrupt the cellular growth in or around the stent. One major disadvantage of these procedures is that it is difficult to selectively apply the energy to the invasive tissue without causing thermal damage to the body lumen wall. In particular, methods that apply energy, such as RF energy, directly to the stent will often cause thermal damage to the surrounding body lumen in which the stent is anchored.

Thus, there is a need for apparatus and methods for removing an occlusion from a body lumen or passage, or from a stent positioned within a body passage, wherein the walls of the body passage are subjected to minimal or no thermal damage, and wherein the application of electrical energy to the stent is avoided. The present invention provides such apparatus and methods, as is described in enabling detail hereinbelow.

SUMMARY OF THE INVENTION

The present invention comprises apparatus and methods for maintaining patency in body passages subject to occlusion, for example, by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around intraluminal prostheses or stents anchored therein.

The principles of the present invention are generally applicable to any body lumen which becomes partially or totally occluded. Methods of the present invention comprise advancing an electrosurgical catheter within the body passage such that an active electrode is positioned near the occlusive media. High frequency voltage is applied to one or more active electrode(s) at the distal end of the catheter such that an electrical current flows from the active electrode(s), through the region of the occlusive media, and to a return electrode to volumetrically remove the occlusive media in situ. In exemplary embodiments, the high frequency voltage is sufficient to effect molecular dissociation or disintegration of the occlusive media, thus converting the solid material of the occlusion into non-condensable gases.

The present invention is particularly useful in a lumen containing a lumenal prosthesis, such as a stent, stent-graft, or graft, which may be metallic, non-metallic, or a non-metallic coated metallic structure. Restenosis often occurs by the proliferation of smooth muscle cells, or when atheromatous material (lipid deposits) or thrombus (clotted blood components) move or form in or around the cylindrical wall of the prosthesis to partially occlude the body passage. Methods of the present invention comprise advancing an electrosurgical catheter within the body passage such that an active electrode is positioned near the occlusive media. High frequency voltage is applied to one or more active electrode(s) at the distal end of the catheter such that an electrical current flows from the active electrode(s), through the region of the occlusive media, and to a return electrode to selectively remove the occlusive media without directly applying thermal or electrical energy to the prosthesis or the lumenal wall. The active electrode may then be advanced through the vacancy left by the removed occlusive media to recanalize the vessel. By selectively removing the occlusive media without passing energy directly to the stent, thermal damage to the surrounding lumenal wall is minimized.

In an exemplary embodiment, the return electrode is located on the catheter so that the current flow paths are confined between the return electrode and one or more active electrodes in the vicinity of the working end of the catheter. This confinement of current flow paths minimizes the undesired flow of current through portions or all of the stent, which may otherwise induce non-specific tissue injury beyond the site of recanalization of the occluded lumen. In one configuration, the return electrode is a movable guide wire positioned radially inward from the active electrode such that the electrical current flows from the active electrode radially inward to the return electrode, thereby inhibiting current flow through the prosthesis. In another embodiment, the return electrode is an annular band positioned proximal of the active electrode(s).

In preferred embodiments, the high frequency voltage is applied in the presence of electrically conductive fluid such that a current flow path is generated between the active electrode(s) and the return electrode through the electrically conductive fluid. Preferably, the electrically conductive fluid is delivered through an internal or external fluid delivery lumen of the catheter (or through a separate instrument) to a region around the occlusive media to displace naturally occurring bodily fluids. This region may be fluidly isolated to confine the electrically conductive fluid around the tissue ablation site. In some embodiments, the fluid is delivered with a positive pressure so as to clear the target site of bodily fluids, such as blood. In one embodiment, the region is isolated by advancing proximal and distal balloons to either side of the region, and inflating these balloons to effect a seal with the interior wall of the body passage.

In one embodiment, the supply of electrically conductive fluid is continuously delivered to the region and can be balanced with the aspiration of fluid from the site of intended recanalization. The active electrode(s) are energized by applying a high frequency voltage between active electrode(s) and the return electrode, which can be a movable guide wire, an electrode on a separate instrument, a fixed electrode on the same instrument, or the like. A high electric field is created at the surface of the electrode(s) which causes the volumetric removal or ablation or target tissue in close proximity with the active electrode(s). As the occlusive media is ablated, gaseous products are generated which may be entrained in the electrically conductive fluid and removed through an aspiration lumen. In exemplary embodiments, the current flux lines are generally confined to the central portion of the region of tissue ablation because they generally flow inward towards the return electrode, and because the occlusive media generally shields the outer region of the body passage (including the stent) from the current flux lines. This minimizes undesirable interaction between the electrical current and the stent. In an exemplary embodiment, the distal portion of the catheter shaft is reciprocally rotated as the active electrode is energized to selectively ablate the occlusive media. The catheter shaft is then advanced through the vacancy left by the ablated occlusive media to recanalize the vessel. In alternative embodiments, the catheter shaft can be advanced longitudinally through the occlusive media without any reciprocating rotational motion.

In a specific configuration, the occlusive media is removed by molecular dissociation or disintegration processes. In these embodiments, the high frequency voltage applied to the active electrode(s) is sufficient to vaporize an electrically conductive fluid (e.g., saline or blood) between the active electrode(s) and the occlusive media. Within the vaporized fluid, an ionized plasma is formed and charged particles (e.g., electrons) cause the molecular breakdown or disintegration of the occlusive media. This molecular dissociation is accompanied by the volumetric removal of the media. This process can be precisely controlled to effect the volumetric removal of tissue or media as thin as 10 to 150 microns with minimal heating of, or damage to, surrounding or underlying tissue structures. A more complete description of this phenomenon is described in commonly assigned U.S. Pat. No. 5,683,366 and in commonly assigned U.S. Pat. No. 5,697,882, the complete disclosure of both of which is incorporated herein by reference.

An apparatus of the present invention generally comprises a catheter having a flexible shaft with a proximal end portion and a distal end portion with one or more active electrode(s), and a connector extending through the shaft for coupling the active electrode(s) to a source of high frequency voltage. The apparatus will preferably include an electrically insulating electrode spacing structure, preferably comprising a support material such as silicone, ceramic, glass, glass/ceramic, or the like, and having a tissue treatment surface at the distal end of the instrument shaft which spaces the active electrode(s) from the return electrode. In one embodiment, the instrument includes an electrode array having a plurality of electrically isolated active electrodes arranged in a circular pattern and embedded into the spacing structure such that the active electrodes extend about 0.0 mm to about 10 mm distally from the tissue treatment surface of the spacing structure.

Upon the application of a sufficient high frequency voltage to the active electrode(s), the occlusive media is volumetrically removed from the body lumen to recanalize the body lumen. In some embodiments, the apparatus will further include one or more fluid delivery element(s) for delivering electrically conductive fluid to the active electrode(s) and the target site. In a specific configuration, an opening of the fluid delivery element is proximal of both the return electrode and the active electrode. The fluid delivery element(s) may be located on the catheter, e.g., one or more fluid lumen(s) or tube(s), or they may be part of a separate instrument. Alternatively, an electrically conductive gel or spray, such as a saline electrolyte or other conductive fluid, may be applied to the target site. In both embodiments, the electrically conductive fluid will preferably generate a current flow path between the active electrode(s) and one or more return electrode(s). In other embodiments, the apparatus may not have a fluid delivery element.

In an exemplary embodiment, the return electrode(s) are located on the catheter and spaced a sufficient distance from the active electrode(s) to substantially avoid or minimize current shorting therebetween and to shield the return electrode(s) from tissue at the target site. Alternatively, the return electrode(s) may comprise a dispersive pad located on the outer surface of the patient (i.e., a monopolar modality).

In a specific configuration, the apparatus includes a plurality of electrically isolated active electrodes extending from the distal end of the catheter shaft. The active electrodes are each mounted within an electrically insulating spacing structure and arranged in a circular pattern. Preferably, the active electrodes are spaced peripherally around a distal opening of the catheter body. In these embodiments, the catheter may include a single, annular return electrode located proximal of the distal opening, or a plurality of return electrodes mounted to the support members proximal of the active electrodes. The catheter body can also include one or more fluid delivery lumens spaced peripherally around the central lumen for delivering electrically conductive fluid to the active electrodes. Additionally, the catheter body can also include one or more suction lumens spaced peripherally around the central lumen and suitably coupled to an external suction source for aspirating fluid, tissue and/or gaseous products of ablation (e.g., non-condensable gases) from the target site.

In a specific configuration, the apparatus includes a shaft having a proximal end and a distal end. Between two and six active electrodes, and preferably two or four electrodes, are arranged in at the distal end of the shaft. A silicone insulating electrode spacing structure seals around the active electrodes so that the active electrodes extend distally approximately 0.1 mm from the spacing structure. The active electrodes are coupled to an energy source through connection wires. A return electrode is spaced at least about 2 mm to 3 mm and sometimes more than 15 mm proximal of the spacing structure and the exposed portion of the active electrodes.

Some embodiments of the present invention comprise a spacing structure which has a larger outer diameter than the outer diameter of the shaft. The larger outer diameter of the spacing structure allows the spacing structure to tunnel through the occlusive media in the vessel while allowing the catheter shaft to traverse through the occlusive media and/or vessel relatively unimpeded. In some embodiments, the catheter will further include one or more lumens for delivering electrically conductive fluid and/or for aspirating the target site to/from one or more openings at the distal end of the catheter. In an exemplary embodiment, the one or more lumens of the catheter will extend through a fluid tube exterior to the catheter shaft that ends proximal to the return electrode.

In one embodiment, the method of the present invention comprises positioning an electrosurgical probe or catheter adjacent the target site so that one or more active electrode(s) and one or more return electrode(s) are positioned in the region of the body structure or lumen. The return electrode(s) are electrically insulated from the active electrode(s) and the patient's body, and a high frequency voltage difference is applied between the active and return electrode(s) to modify or ablate at least a portion of the body structure.

In some embodiments of the present invention, the instrument will comprise a catheter designed for percutaneous and/or transluminal delivery. In other embodiments, the instrument will comprise a more rigid catheter designed for percutaneous or direct delivery in either open procedures or port access type procedures. In both embodiments, the apparatus will include a high frequency power supply for applying a high frequency voltage to the active electrode(s).

In another aspect, the present invention provides an instrument comprising one or more active electrode(s) at the distal end, and a return electrode on the instrument shaft and spaced proximally from the active electrode(s). A thin, electrically insulating jacket surrounds the return electrode to insulate the return electrode from the active electrode. The insulating jacket has a material and thickness selected that will allow for sufficient charge to build on the electrodes to ablate or otherwise modify the tissue ingrowth or stenotic material adjacent to the active electrode(s). In the representative embodiment, the insulating jacket comprises a polytetrafluoroethylene (e.g., Teflon), a polyimide, , a urethane, or a silicone material, and has a thickness in the range of about 0.01 mm to 0.5 mm.

According to one aspect of the invention, the occlusive media is ablated with high frequency voltage through a capacitive charge process. Specifically, the active electrodes(s) on the catheter distal end are positioned adjacent to, or in the region of, occlusive media within a body passage. The active electrodes(s), together with a surrounding electrically conductive fluid, function as the first conducting plate of a capacitor device. The return electrode (second conducting plate), having a dielectric thereon, is spaced proximally from the active electrode(s). A high frequency voltage is applied between the conducting plates to create a potential difference that results in a charge on the conducting plates and creates an electric field therebetween. The electric field intensity is sufficient to volumetrically remove the occlusive media. Capacitive charge electrosurgical devices and methods are described in commonly-assigned U.S. patent application Ser. No. 09/477,832, the contents of which are incorporated herein by reference.

The amount of charge, Q, built up on the conductors of a capacitor is proportional to the applied voltage. The constant of proportionality, C, is the capacitance in farads (F) and depends on the capacitor construction. The capacitance, C, is generally proportional to the dielectric constant of the insulator times the surface area of the conductors times the distance between the active conductor and the return conductor (i.e., the thickness of the insulator). In one configuration, a conductive medium is present between the first or active conductor and the insulator which effectively creates a virtual conductor that includes the active conductor and the conductive medium. In this manner, the active conductor and return conductor may be spaced a larger distance away from each other (typically from 1 to 50 mm) without effectively reducing the capacitance of the capacitor, because the distance between the conductors is measured as the distance from the conductive fluid/insulator interface and the return conductor/insulator interface.

In one aspect of this embodiment, the first conductor of the capacitor comprises one or more active electrodes positioned at the distal end of an instrument shaft. The second conductor comprises a return electrode spaced proximally from the active electrode(s) on the shaft, and the insulator comprises a thin, insulating jacket around the return electrode. In this manner, the return electrode is also insulated from the patient's body. Conductive fluid is present around the instrument shaft such that the insulator and the active electrode(s) contact the conductive fluid. The insulator may comprise Teflon, silicone rubber, urethane, a polyimide, or similar material, and will typically have a thickness of about 0.01 to 0.5 mm which effectively represents the distance between the two electrodes of the capacitor. The return electrode will typically have a larger surface area than the active electrode(s) to provide a more uniform distribution of charge across the return electrode surface and to minimize the charge at any point on this surface. The active electrodes will typically have a smaller surface area to maximize the charge on the surface of the active electrode(s).

In a specific configuration, the active and return electrode(s) are spaced from each other on the distal end portion of a surgical instrument. The return electrode(s) are insulated from the active electrode(s) and the patient's body by an insulator, preferably a thin, insulating jacket that surrounds the shaft of the instrument and the return electrode. In one embodiment, the distal end of the catheter is immersed in electrically conductive fluid such that a conductive path is created between the insulator and the active electrode(s). The electrically conductive fluid may be delivered directly to the active electrode(s) or the entire target site may be submersed within the conductive fluid. Applicant believes that the conductive fluid creates a virtual conductor or virtual electrode that includes the active electrode(s) and the conductive fluid surrounding the distal end portion of the instrument. With this configuration, a capacitor is created with the return electrode functioning as the second parallel plate or conductor, and the insulator functioning as the dielectric between the electrodes. When high frequency voltage is applied between the electrodes, a potential difference is created that results in a charge on the electrodes, creating an electric field therebetween.

According to one embodiment of the present invention, the active and return electrode(s) are configured such that the charge on the electrodes, and the intensity of the electric field, is sufficient to ablate or volumetrically remove the occlusive media in contact with, or in close proximity to, the active electrode(s). Since, in this embodiment, current is not flowing into the occlusive media, the modification or ablation of the occlusive material is accomplished at substantially lower temperatures than traditional electrosurgery, which reduces collateral tissue damage. In addition, the current does not penetrate beyond the target site, which further reduces damage to the surrounding lumenal wall. Moreover, the electric current is precisely controlled, which allows the device to be used adjacent to electrically sensitive structures, such as nerves, the heart or the spine. Another advantage of the present invention is that the alternating current flow between the electrodes is more uniform across the surface of the return electrode, rather than collecting at the distal corner of the return electrode, as may occur with traditional electrosurgical devices.

In another application, an electrosurgical catheter is advanced within the body passage such that an active electrode and a return electrode are positioned near the occlusive media. A high frequency voltage is applied between the active and return electrodes as described above, to produce a charge sufficient to volumetrically remove the occlusive media in situ. In exemplary embodiments, the high frequency voltage is sufficient to effect molecular dissociation or disintegration of the occlusive media, thus converting the solid media into non-condensable gases or other low molecular weight ablation by-products. According to the present invention, the return electrode is insulated from the active electrode and the patient's body to eliminate the potential for contact between the return electrode and the body lumen, which could otherwise cause thermal damage to the walls of the vessel.

The present invention is particularly useful in a lumen containing a lumenal prosthesis, such as a stent, stent-graft or graft, which may be metallic, non-metallic or a non-metallic coated metallic structure. Restenosis often occurs when artheromatous material or thrombus move or from in or around the cylindrical wall of the prosthesis to partially occlude the body passage. In this application, it is particularly useful to insulate the return electrode from the conductive stent, and to control the flow of current at the target site to minimize current flow through the stent.

In one aspect of the invention, there is provided a catheter having a spacer or electrode support and a plurality of active electrodes on the electrode support; wherein the electrode support includes a support distal portion, and the support distal portion tapers from narrow to broad in a proximal direction to a position of maximum width or girth of the electrode support. In one embodiment, the plurality of active electrodes are located on the support distal portion at a location distal to the position of maximum width of the electrode support, and the position of maximum width of the electrode support is wider than the width or diameter of the catheter shaft.

In another aspect of the invention, there is provided a catheter including a plurality of active electrode leads or connection wires, wherein each of the plurality of active electrode leads is a hybrid electrode lead including a distal portion comprising a first metallic composition, and a proximal portion comprising a second metallic composition. In one embodiment, the first metallic composition comprises platinum or platinum/iridium, and the second metallic composition comprises molybdenum. In one embodiment, an exposed distal portion of each active electrode lead forms an active electrode terminal, including a first free end, a loop portion, and a second connected end, wherein the first free end terminates in the electrode support, the loop portion defines a gap between the active electrode and the electrode support, and the second connected end is in communication with the active electrode lead.

In another aspect of the invention, the electrode support distal portion is substantially conical in shape, and the loop portion of each active electrode comprises a curved wire radiating proximally from a position proximal to the apex of the electrode support on the support distal portion, wherein the loop portion of each active electrode terminates at a location distal to the position of maximum width of the electrode support.

In another aspect of the invention, there is provided a catheter including at least one return electrode lead or connection wire coupled to a return electrode, wherein the return electrode lead is a hybrid lead including a distal portion comprising platinum or platinum/iridium, and a proximal portion comprising molybdenum. In one embodiment, the hybrid return electrode lead is coupled to a return electrode in the form of an annular band of platinum or platinum/iridium alloy.

In another aspect of the invention, there is provided a catheter having a distal spacer or electrode support and at least one active electrode sealably arranged on the electrode support; wherein the electrode support includes a support distal portion having at least one active electrode socket therein for accommodating a loop portion of an active electrode, and the active electrode is recessed within the electrode support.

In another embodiment of the invention, the catheter system includes a high frequency power supply configured to reduce or interrupt power when the active electrode(s) contact a low impedance object, such as a stent within the body lumen. In one embodiment, the power supply includes a spark prevention device for eliminating or reducing sudden pulses in current when an instrument powered by the power supply contacts a low impedance source. The spark limiting device is coupled to one or more current sensors on the active electrode(s) to substantially continuously monitor current output, interrupting current output from the output driver when current output from the output current sensor exceeds a predetermined threshold level. The spark prevention mechanism, which may be used in conjunction with other power regulatory devices or elements, preferably turns off output from the power supply when output current from the supply exceeds a predetermined current level.

In another aspect of the invention, there is provided an electrosurgical system including a high frequency power supply and a catheter having a plurality of electrodes, wherein each of the plurality of electrodes are independently coupled to the power supply via a catheter cable, and the catheter cable is integral with the catheter, wherein the power supply includes a current sensor and at least one power regulatory component, such as a power limiting device or a spark limiting device. In one aspect, power supplied from the power supply is interrupted to an electrode which inadvertently contacts a metal prosthesis or other low impedance object. In another aspect, power supplied from the power supply continues without interruption to the remainder of a plurality of electrodes in the event that one or more of the plurality of electrodes inadvertently contacts a metal prosthesis or other low impedance object. In another aspect of the invention, the catheter includes a fluid delivery device for delivering an electrically conductive fluid to a target site, the high frequency power supply includes a fluid interlock element, and the fluid interlock element causes interruption of power supplied to the catheter in the event that an amount of the electrically conductive fluid at the target site is less than a minimum threshold quantity.

In a further aspect of the invention, there is provided a method of recanalizing a body lumen or passage by a cool ablation procedure, in which occlusive material within the body passage is volumetrically removed by the molecular dissociation of components of the occlusive material, to yield low molecular weight ablation by-products. In a currently preferred embodiment, the cool ablation procedure is performed at a temperature in the range of 40° C. to 45° C., thereby minimizing thermal damage to the body passage. According to one aspect of the invention, neither the walls of the body passage, nor the stent, are exposed to a temperature in excess of 45° C. during the entire recanalization procedure.

In another aspect of the invention, there is provided a method of making an electrosurgical catheter adapted for maintaining patency in a body lumen or for recanalizing a body lumen. The method includes providing a catheter shaft, together with a return electrode assembly, as well as an active electrode assembly; and assembling the return electrode assembly and the active electrode assembly to the shaft. The method further includes sealably arranging each of a plurality of active electrodes on or within an electrically insulating electrode support or spacer. In one embodiment, the plurality of active electrodes are forced through a spacer comprising a pliable, electrically insulating material, after which the active electrodes may be bent to form a loop portion defining a gap which separates the active electrode from the spacer. In another embodiment, the plurality of active electrodes are first bent to form a loop portion, and the spacer is molded around the active electrodes such that the loop portion of each active electrode is exposed on the surface of the spacer.

Other aspects, features, and advantages of the present invention will become apparent upon consideration of the remaining portions of the specification and drawings.

BRIEF DESCRIPTION OF THE DRAWINGS

FIG. 1 schematically illustrates a lumen recanalization catheter system according to the present invention;

FIGS. 28A, 28B show a catheter including a moveable, external fluid delivery unit;

DESCRIPTION OF SPECIFIC EMBODIMENTS

Figure 2A:
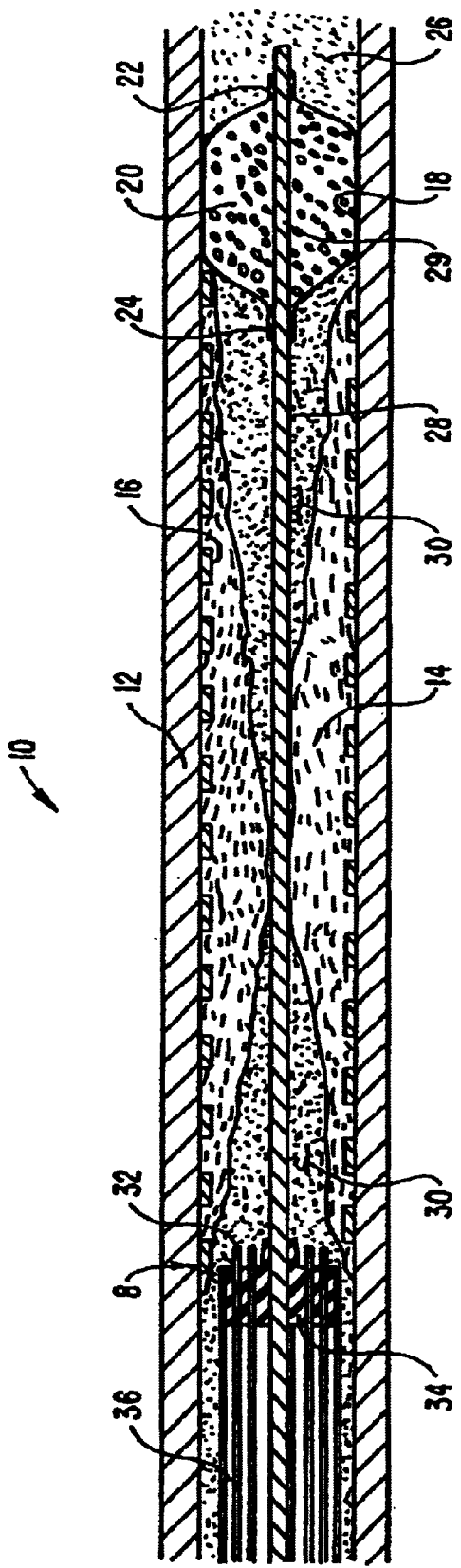
FIGS. 2A–2C illustrate a method of recanalizing an obstructed lumen according to the present invention.

The present invention relates generally to the field of electrosurgery, and more particularly to surgical devices, systems and methods which employ high frequency electrical energy to remove or ablate tissue attached to implanted objects within the body. The systems and methods of the present invention are particularly useful for removing atheromatous material which partially or fully occludes the body lumen, such as a blood vessel or for removing tissue or other material from the interior of stents or other implanted objects. Moreover, other body lumens that may be treated by the method and apparatus of the present invention include the urinary tract (which for example may be occluded by an enlarged prostrate in males), the fallopian tubes (which may be occluded and cause infertility), and the like. In fact, the methods and apparatus disclosed herein may be used in a wide variety of procedures, including open procedures, intravascular procedures, urology, laparascopy, arthroscopy, thoracoscopy or other cardiac procedures, dermatology, orthopedics, gynecology, otorhinolaryngology, spinal and neurologic procedures, oncology and the like. For convenience, the remaining disclosure will be directed specifically to the removal of occlusive media within body lumens.

The stenotic material in blood vessels will be, by way of example but not limited to, atheroma or atheromatous plaque. It may be relatively soft (fresh) or it may be calcified and hardened. The invention applies energy selectively to the stenotic material to remove this material while limiting unwanted heating of the blood, the surrounding vessel wall and the stent anchored therein. In some embodiments, the present invention confines the current flow paths between the return electrode and active electrodes to the vicinity of the tissue ablating region of the electrosurgical catheter. This confinement of current flow paths minimizes the undesired flow of current through the walls of the body passage, or through portions or all of the stent, which may otherwise induce non-specific tissue injury beyond the site of recanalization of the occluded lumen.

In the present invention, high frequency (RF) electrical energy is applied to one or more active electrodes (usually in the presence of electrically conductive fluid) to remove and/or modify body structures, tissue, or occlusive media. Depending on the specific procedure, the present invention may be used to: (1) volumetrically remove occlusive media in a body passage; (2) volumetrically remove body structures (i.e., ablate or effect molecular dissociation of the structure); (3) cut or resect body structures; (4) vaporize, cauterize or desiccate structures and/or (5) coagulate and seal severed blood vessels.

In the preferred method of the present invention, the occlusive media is volumetrically removed or ablated. In this procedure, the high frequency voltage difference applied across the electrodes is sufficient to develop high electric field intensities in the vicinity of the occlusive media. The high electric field intensities adjacent the first conductor or active electrode(s) lead to electric field induced molecular breakdown of occlusive media through molecular dissociation (rather than thermal evaporation or carbonization). Applicant believes that the occlusive media is volumetrically removed through molecular disintegration of larger organic molecules into smaller molecules and/or atoms, such as hydrogen, oxygen, oxides of carbon, hydrocarbons and nitrogen compounds. This molecular disintegration completely removes the occlusive media, as opposed to dehydrating the tissue or occlusive media by the removal of water from the tissue or occlusive media, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the occlusive media. The electrically conductive fluid may be a liquid or gas, such as isotonic saline or blood, delivered to the target site, or a viscous fluid, such as a gel, applied to the target site. Since the vapor layer or vaporized region has a relatively high electrical impedance, it minimizes the current flow into the electrically conductive fluid. This ionization, under the conditions described herein, induces the discharge of energetic electrons and photons from the vapor layer and to the surface of the target media. A more detailed description of this phenomenon, termed Coblation® can be found in commonly assigned U.S. Pat. No. 5,697,882 the complete disclosure of which is incorporated herein by reference.

Applicant believes that the principle mechanism of ablation in the Coblation® mechanism of the present invention is energetic electrons or ions that have been energized in a plasma adjacent to the active electrode(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating gas and ionizing the gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in Applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conductive fluid environment to remove (i.e., resect, cut or ablate) the occlusive media. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the active electrode(s). In other embodiments, the power supply is combined with the coagulation instrument such that the coagulation electrode is used when the power supply is in the coagulation mode (low voltage), and the active electrode(s) are used when the power supply is in the ablation mode (higher voltage).

In addition to the above, Applicant has discovered that the Coblation® mechanism of the present invention can be manipulated to ablate or remove occlusive media, while having little effect on the surrounding body structures. As discussed above, the present invention uses a technique of vaporizing electrically conductive fluid to form a plasma layer or pocket around the active electrode(s), and then inducing the discharge of energy from this plasma or vapor layer to break the molecular bonds of the occlusive media. Based on initial experiments, applicants believe that the free electrons within the ionized vapor layer are accelerated in the high electric fields near the electrode tip(s). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) has double bonds that require a substantially higher energy level than 4 to 5 eV to break. Accordingly, the present invention in its current configuration generally does not ablate or remove such fatty tissue. However, the present invention may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998 the complete disclosure of which is incorporated herein by reference.

The present invention applies high frequency (RF) electrical energy in an electrically conductive fluid environment to remove (i.e., resect, cut or ablate) a body structure, occlusive media, or an occlusion within a body passage, lumen, orifice, or an in situ prosthesis.

The electrosurgical instrument of this embodiment comprises a shaft having a proximal end and a distal end which supports one or more active electrode(s). The shaft may assume a wide variety of configurations, with the primary purpose being to mechanically support one or more active electrode(s) and permit the treating physician to manipulate the electrode(s) from a proximal end of the shaft. Usually, an electrosurgical catheter shaft will be a narrow-diameter rod or tube, more usually having dimensions which permit it to be introduced through a cannula into the patient's body. Thus, the catheter shaft will typically have a length of at least 5 cm for open procedures and at least 10 cm, more typically being 20 cm, or longer for endoscopic procedures. The catheter shaft will typically have a diameter of at least 1 mm and frequently in the range from 1 mm to 10 mm. For dermatology or other procedures on the skin surface, the shaft will have any suitable length and diameter that would facilitate handling by the surgeon.

The electrosurgical instrument may also be a catheter that is delivered percutaneously and/or endoluminally into the patient by insertion through a conventional or specialized guide catheter, a rapid exchange catheter, or a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The catheter may also include other internal lumens for providing separate functions, such as delivering fluid and aspirating products of ablation from the target site. Preferably, the catheter will have a fluid delivery lumen for delivering electrically conductive fluid to the target site. The catheter may have an aspiration lumen coupled to a vacuum source for aspirating non-condensable gases and other products of ablation from the site.

The catheter may also include an isolation system for fluidly isolating the region around the target site. In one embodiment, the isolation system includes proximal and distal balloons that are movable to portions of the body passage proximal and distal to the region of the target site. The distal balloon, by way of example, may be formed on a hollow guide wire that is fluidly coupled to an inflation source, such as a syringe. The proximal balloon, for example, may be coupled to the catheter body proximal to the active and return electrodes.

In one embodiment, the invention typically includes guiding apparatus for guiding the catheter along a pathway approximating the central region of the occluded blood vessel. The guiding apparatus is usually an electrically conducting wire that may serve as the return electrode. The electrically conducting wire is extensible from the distal tip of the catheter and is located within and concentric to the catheter conveniently being in the form of a movable or fixed guidewire, usually being a movable guidewire.

The active electrode(s) are preferably supported within or by an electrically insulating spacing structure, such as silicone, urethane, Teflon, polyimide, or similar material, which is positioned near the distal end of the instrument shaft. The return electrode may be either integral with the instrument shaft, or may be on another instrument located in close proximity to the distal end of the catheter shaft. The proximal end of the catheter will include the appropriate electrical connections for coupling the return electrode(s) and the active electrode(s) to a high frequency power supply, such as an electrosurgical generator. One or more insulators will be positioned around the return electrode to insulate the return electrode from the electrically conductive fluid and the patient's body.

A current flow path may be generated by submerging the tissue site in an electrically conductive fluid (e.g., within a viscous fluid, such as an electrically conductive gel) or by directing an electrically conductive fluid along a fluid path to the target site (i.e., a liquid, such as isotonic saline, hypotonic saline; or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, the contents of which are incorporated herein by reference in their entirety. Alternatively, the body's natural conductive fluids, such as blood, may be sufficient to establish a current flow path, and to provide the conditions for establishing a vapor layer, as described above. However, electrically conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. patent application Ser. No. 09/058,336, filed Apr. 10, 1998 the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, co-pending patent application Ser. No. 09/010,382, filed Jan. 21, 1998, the complete disclosure of which is incorporated herein by reference.

In one configuration, each individual active electrode in the electrode array is electrically insulated from all other active electrodes in the array within said instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument (catheter), connectors, cable, power supply, or elsewhere along the conductive path from the power supply to the distal end of the instrument. Alternatively, the resistance and/or capacitance may occur on the surface of the active electrode(s) due to oxide layers which form selected active electrodes (e.g., titanium or a resistive coating on the surface of metal, such as platinum).

In some configurations, the spacing structure and the fluid outlet may be recessed from an outer surface of the instrument or handpiece to confine the electrically conductive fluid to the region immediately surrounding the spacing structure. In addition, the shaft may be shaped so as to form a cavity around the spacing structure and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the occlusive media at the treatment site throughout the procedure, which reduces the thermal damage to the lumen that might otherwise occur if the vapor layer were extinguished due to a lack of conductive fluid. Provision of the electrically conductive fluid around the target site also helps to maintain the temperature of the target site at desired levels.

In other configurations, the active electrodes are spaced from the occlusive media a sufficient distance to minimize or avoid contact between the occlusive media and the vapor layer formed around the active electrodes. In these embodiments, contact between the heated electrons in the vapor layer and the occlusive media is minimized as these electrons travel from the vapor layer back through the conductive fluid to the return electrode. The ions within the plasma, however, will have sufficient energy, under certain conditions such as higher voltage levels, to accelerate beyond the vapor layer to the occlusive media. Thus, the molecular bonds are dissociated or broken as in previous embodiments, while minimizing the electron flow, and thus the thermal energy, in contact with the occlusive media.

The electrical conductivity of the electrically conductive fluid (in units of milliSiemens per centimeter or mS/cm) will usually be greater than 0.2 mS/cm, preferably greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than isotonic saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with electrically conductive fluids comprising elements other than sodium, such as potassium, magnesium, calcium and other metals on the left side of the Periodic Table (e.g., elements in Groups IA and IIA). In addition, other electronegative elements may be used in place of chlorine, such as fluorine. In some applications, Applicant has found that a frequency of about 100 kHz is useful because the tissue impedance is much greater at this frequency as compared with a frequency of about 500 kHz. In other applications, such as procedures in or around the heart or head and neck, higher frequencies may be desirable (e.g., 400–600 kHz) to minimize low frequency current flow into the heart or the nerves of the head and neck.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). For removal of occlusive media within body lumens, the voltage will usually be in the range of about 100 Vrms to 300 Vrms. Typically, the peak-to-peak voltage will be in the range of 10 volts to 2000 volts and preferably in the range of 20 volts to 500 volts and more preferably in the range of about 40 volts to 450 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed at about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular cardiac surgery, arthroscopic surgery, dermatological procedure, ophthalmic procedures, open surgery or other endoscopic surgery procedure. For cardiac procedures, the power source may have an additional filter, for filtering leakage voltages at frequencies below 100 kHz, particularly voltages around 60 kHz. A description of a suitable power source can be found in U.S. Provisional Application No. 60/062,997, filed on Oct. 23, 1997, the full disclosure of which is incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from the active electrode into the low resistance medium (e.g., saline irrigant, blood).

In yet another aspect of the invention, the power supply or controller is "tuned" so that it will not apply excessive power to the blood (e.g., in the ventricle), once it crosses the wall of the heart and enters the chamber of the left ventricle. This minimizes the formation of a thrombus in the heart (i.e., will not induce thermal coagulation of the blood). The power supply may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the probe can be used to detect the boundary between the wall of the heart and the blood filled left ventricle chamber, turning off the electrode array just as the probe crosses the boundary.

It should be clearly understood that the invention is not limited to electrically isolated active electrodes, or even to a plurality of active electrodes. For example, the array of active electrodes may be connected to a single lead that extends through the catheter shaft to a power source of high frequency current. Alternatively, the catheter may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter comprises a single active electrode that extends from an insulating member, e.g., ceramic, at the distal end of the shaft. The insulating member is preferably a tubular structure that separates the active electrode from a tubular or annular return electrode positioned proximal to the insulating member and the active electrode. In another embodiment, the catheter includes a single active electrode that can be rotated relative to the rest of the catheter body, or the entire catheter may be rotated relative to the body lumen.

Referring to the drawings in detail, wherein like numerals indicate like elements, FIG. 1 shows a lumen recanalization catheter system 2 constructed according to the principles of the present invention. Catheter system 2 generally comprises an electrosurgical catheter 6 connected to a power supply 80 by an interconnecting cable 86 for providing high frequency voltage to a target tissue and an irrigant reservoir or source 100 for providing electrically conductive fluid to the target site. Catheter 6 generally comprises an elongate, flexible shaft body 12 including a tissue ablating region 8 at the distal end of body 12, and a proximal balloon 40 positioned on body 12 proximal to region 8. In a specific embodiment, a guide wire 28 (which may also serve as a return electrode) includes a distal balloon 18 which may be axially translated relative to region 8 and proximal balloon 40, as discussed in further detail below.

The proximal portion of catheter 6 includes a multi-lumen fitment 114 which provides for interconnections between lumens and electrical leads within catheter 6 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 6 extend between one or more active electrodes at tissue ablating region 8 and one or more corresponding electrical terminals (also not shown) in catheter connector 96 via active electrode cable branch 87. In the illustrative embodiment, hollow guide wire 28 functions as the return electrode, and is electrically attached within a contact housing 111 by a sliding electrical contact (not shown). A return electrode cable branch 89 couples the sliding electrical contact to catheter connector 96. Electrical leads within cable 86 allow connection between terminals corresponding to return electrode 28 and one or more active electrodes 32 (e.g., FIG. 2A) in distal cable connector 94 and power supply 80.

Power supply 80 has an operator controllable voltage level adjustment 82 to change the applied voltage level, which is observable at a voltage level display 84. Power supply 80 also includes a foot pedal 88 and a cable 90 which is removably coupled to power supply 80 for remotely adjusting the energy level applied to active electrodes 32. In an exemplary embodiment, power supply 80 includes three such foot pedals (not shown), wherein the first foot pedal is used to place the power supply into the "ablation" mode and the second foot pedal places power supply 80 into the "subablation" mode. The third foot pedal allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, and ionizing charged particles within the vapor layer). As discussed above, the requisite voltage level for ablation will vary depending on the number, size, shape and spacing of the electrodes, the distance to which the electrodes extend from the support member, etc. Once the surgeon places the power supply in the "ablation" mode, voltage level adjustment 82 or the third foot pedal may be used to adjust the voltage level to adjust the degree or aggressiveness of the ablation.

Of course, it will be recognized that the voltage and modality of the power supply may be controlled by other input devices. However, applicant has found that foot pedals are convenient means for controlling the power supply while manipulating the probe during a surgical procedure.

In the subablation mode, the power supply 80 applies a low enough voltage to the active electrodes to avoid vaporization of the electrically conductive fluid and subsequent molecular dissociation of the tissue. The surgeon may automatically toggle the power supply between these modes by alternatively stepping on the foot pedals. This allows the surgeon to quickly move between subablation (e.g., coagulation) and ablation in situ, without having to remove his/her concentration from the surgical field or without having to request an assistant to switch the power supply.

Figure 13:
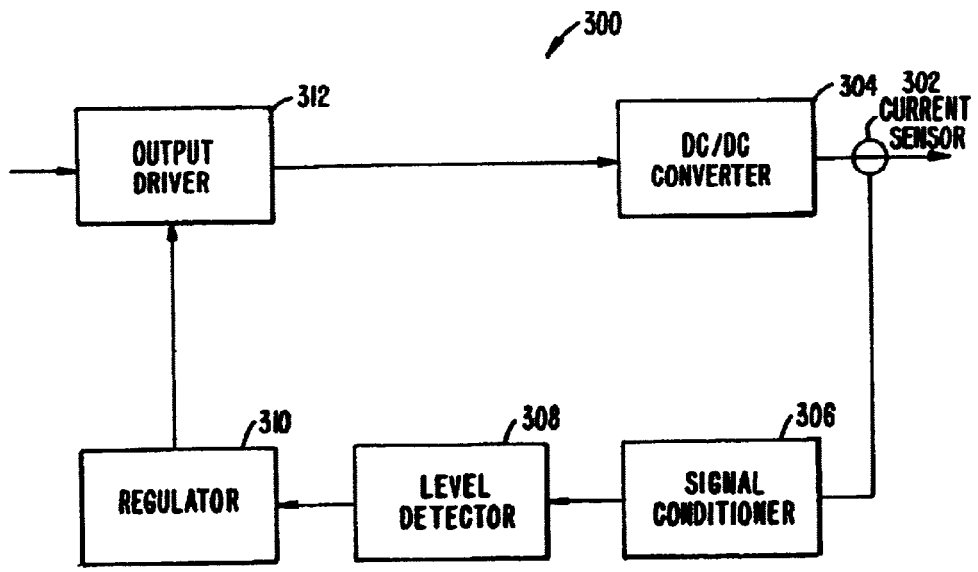
FIG. 13 is a block diagram of a power limiting device according to the present invention.

Referring now to FIGS. 13–22, an exemplary power supply will be described. The power supply of the present invention may include power limiting devices to protect attached electrosurgical catheters from excessive power delivery and to sustain controlled operation of the catheter or instrument. Power is the time rate of transferring or transforming energy, and for electricity, power is measured in watts, where one watt is the power to create energy at the rate of one joule per second. Referring to FIG. 13, a power limiting device 300 is designed to reduce the power drawdown from the power supply when an attached device, such as a monopolar or bipolar surgical instrument, is not engaging body tissue or draws excessive power. For example, excessive power is delivered from the power supply if the RF catheter is in saline or blood and is not engaging target media. Device 300 conveniently conserves power supplied to the catheter without completely deactivating the power supply or requiring the user to manually reduce power. Excessive power draw will overheat the power supply and corrupt power supply performance. Device 300 also acts as a safety feature by reducing the stray emission of energy when the catheter is in transit through the body to a target site.

Figure 14:
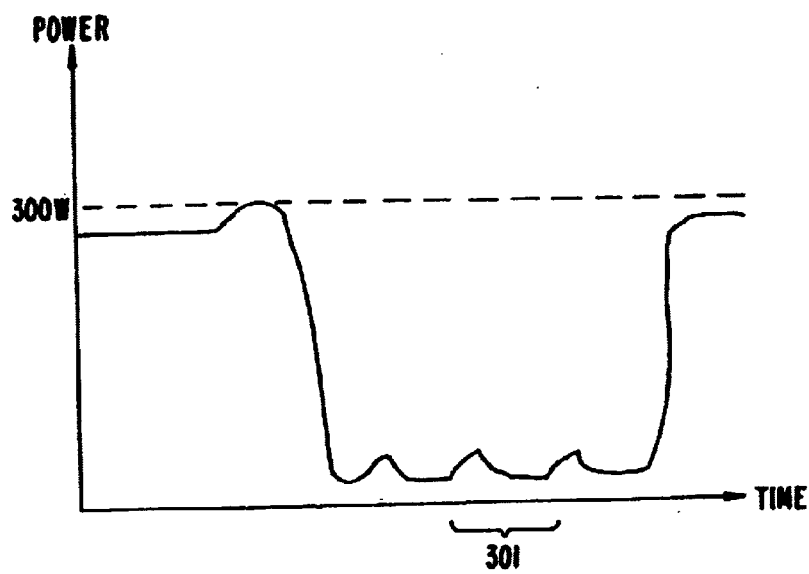
FIG. 14 is a graph of the power output of the power supply during normal operations and standby mode.

In general terms, the power limiting device 300 operates on a continuous basis to detect excessive power output. The device 300 is responsive to the "total power" delivered by the power supply. FIG. 14 illustrates the power output of the power supply when an excessive power is detected. Device 300 limits the overall output power from the power supply to be lower than about 240–360 watts, preferably less than about 300 watts. Once power output exceeds a predetermined threshold level, the device 300 then operates on a duty cycle or periodic detection cycle 301 between about 50 and 300 ms, where the device 300 checks every cycle to determine if it is safe to resume power output. Preferably, the device 300 has a fixed duty cycle wave form and includes a fixed periodical pulsing circuit which is about 10 ms on and 90 ms off. Once the fault condition is gone, power output returns to operating levels.

In one embodiment (FIG. 13), the device 300 uses a current sensor 302 attached to the output electrodes to derive the power output of the power supply. The current limit, which may be set at any desired level, is about 5 amps for a 300 watt power limit when voltage is set at about 60V. When current output reaches 5 amps, the device 300 reduces the output of the power supply to a standby mode. Once in standby mode, the power supply preferably has a pulsatile power output. As shown in FIG., the device 300 allows the current output to be activated during each duty cycle to determine if the power supply may return to normal operation.

Figure 15:
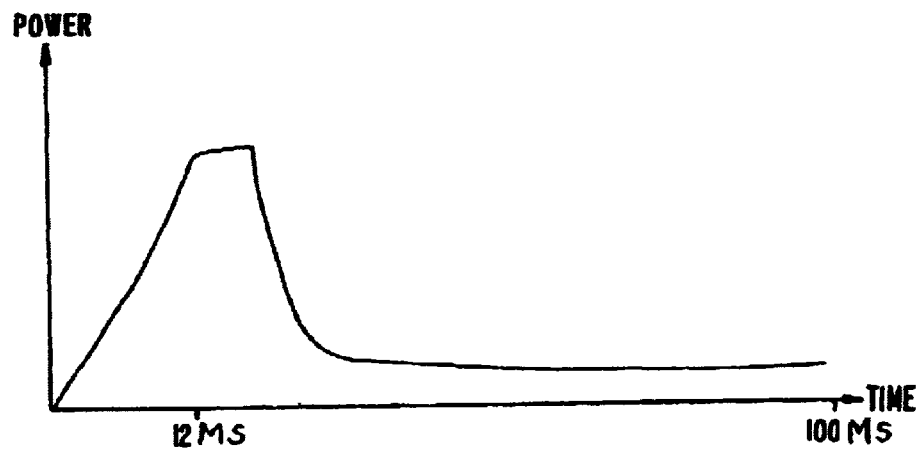
FIG. 15 is a graph of the power output of the power supply in a low power, pulsatile mode.

When in the standby mode, the pulsatile power output may be described as shown in FIG. 15. In the pulsatile mode, the duty cycle is about 10–15 ms on, preferably about 12 ms on, and about 85–90 ms off, preferably about 88 ms off. This creates a cycle of about 100 ms, during which time, power is increased and then reduced if the probe senses that it is not in the vicinity of body tissue or other higher impedance material. This sensing step is the initial portion of the duty cycle where current is activated for a period of time, described as being between 10–15 ms. If current again reaches the 5 amp level or some other predetermined level, the output is reduced and the device 300 waits for the next duty cycle. The total power output during this short period is only about 10 watts. However, the current output is sufficient to show that the fault condition still exists. Thus, when in the standby mode, the device 300 tests for potentially excessive power output with a fault condition that occurs without actually reaching the power level against which the device is protecting. This pulsatile power output continues until power drawdown returns to within acceptable ranges (FIG. 14). The power limiting feature reduces power output on a fault condition that is current based (so long as there is constant voltage).

Alternatively, the power limiting device 300 in the standby mode checks the impedance (instead of current) encountered by the probe every 100 ms or over some other interval selected by the user. As long as the instrument is in a low impedance environment and impedance is below a predetermined level, the power supply will operate in the pulsatile mode, never fully activating to therapeutic power levels such as for ablation or coagulation. The low impedance is indicative of a potential over power scenario. In alternative embodiments, the device 300 may check the impedance over variable time intervals that change as desired. When the instrument reaches a target site or comes in the vicinity of higher impedance tissue, in one embodiment, a higher impedance is noted by a drop in current draw (i.e. power draw) from the probe, signaling the regulator or logic unit 310 to increase power on the current or the next duty cycle. This brings the power supply out of the pulsatile mode. The power limiting device 300, however, will continue to check the impedance encountered every duty cycle.

Figure 16A:
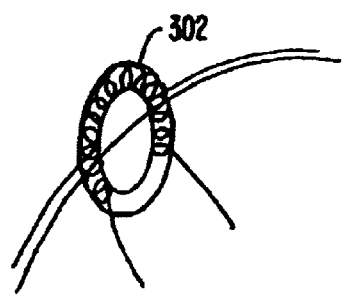
FIGS. 16A–16C show various embodiments of a current sensor.
Figure 16C:
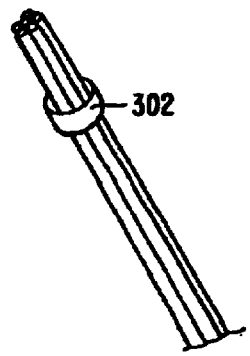
Figure 16B:
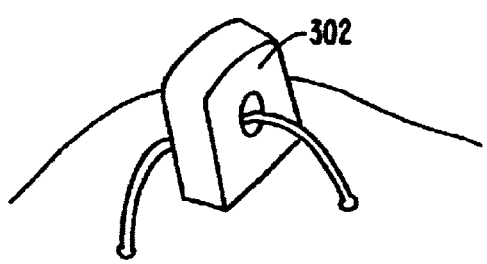

Referring to FIGS. 16A–16C, a preferred embodiment of the device 300 comprises of at least one current sensor 302 detecting the current output from DC/DC converter 304. The current sensor 302 may be configured as one sensor for one electrode or one sensor for a plurality of electrodes. In the present embodiment, one sensor 302 is used for six electrodes on the probe, although more preferably one sensor is used for three electrodes. Typically, the sensors 302 (noted as T1, T4, T5, etc.) are configured to wrap around the electrodes as shown in FIG. 16. Signals from sensors 302 are passed through a plurality of rectifying diodes and capacitors which filter and condition the typically analog signal from the current sensor. In the block diagram of FIG. 13, these diodes and components are represented by signal conditioner 306. The conditioned signal from the sensor 302 is then passed to a level detector or voltage comparator 308. The comparator 308 determines if the current output has exceeded the predetermined threshold level. A regulator or logic unit 310 then determines power of output driver 312 based on the value of the output current compared to a predetermined current value. In the standby or power limited mode, the logic unit 310 of the device 300 will preferably duty cycle the output from output driver 312. Although the logic unit 310 is preferably an integrated circuit such as a Field Programmable Gate Array (FPGA) to maximize cost efficiency, it should be understood that other devices such as computers or microprocessors may also be used to perform the required logic functions.

Figure 17A:
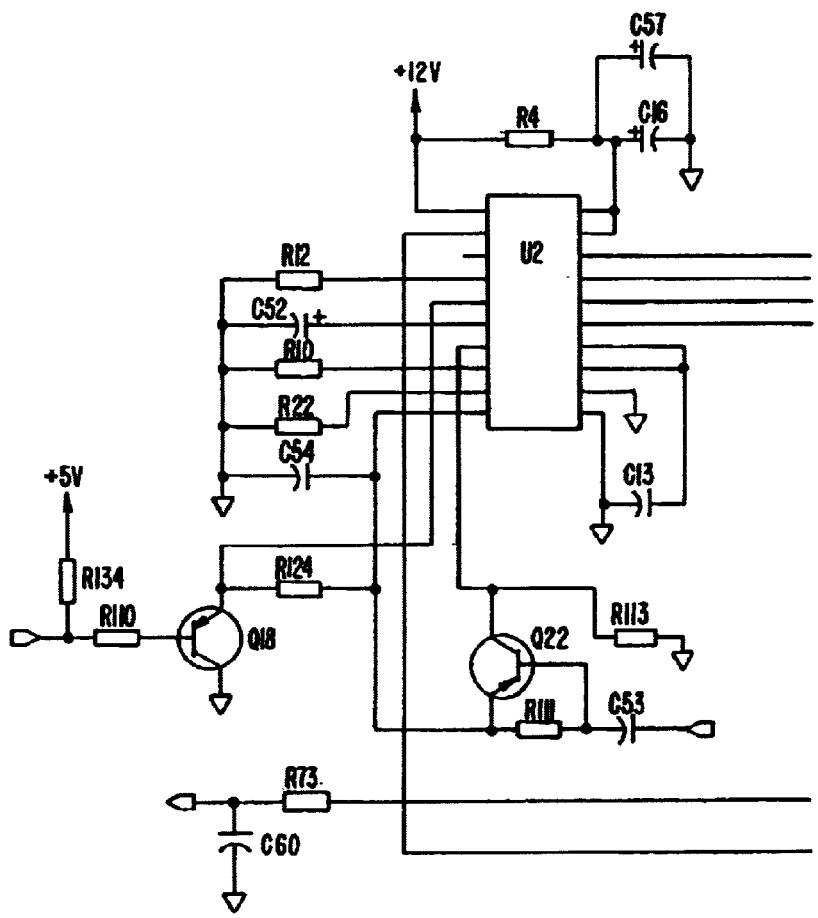
FIGS. 17A–C each show a circuit schematic of an exemplary embodiment of a power limiting device.
Figure 17:
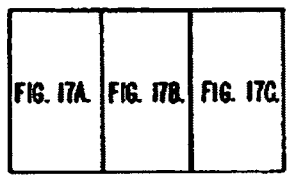
Figure 17B:
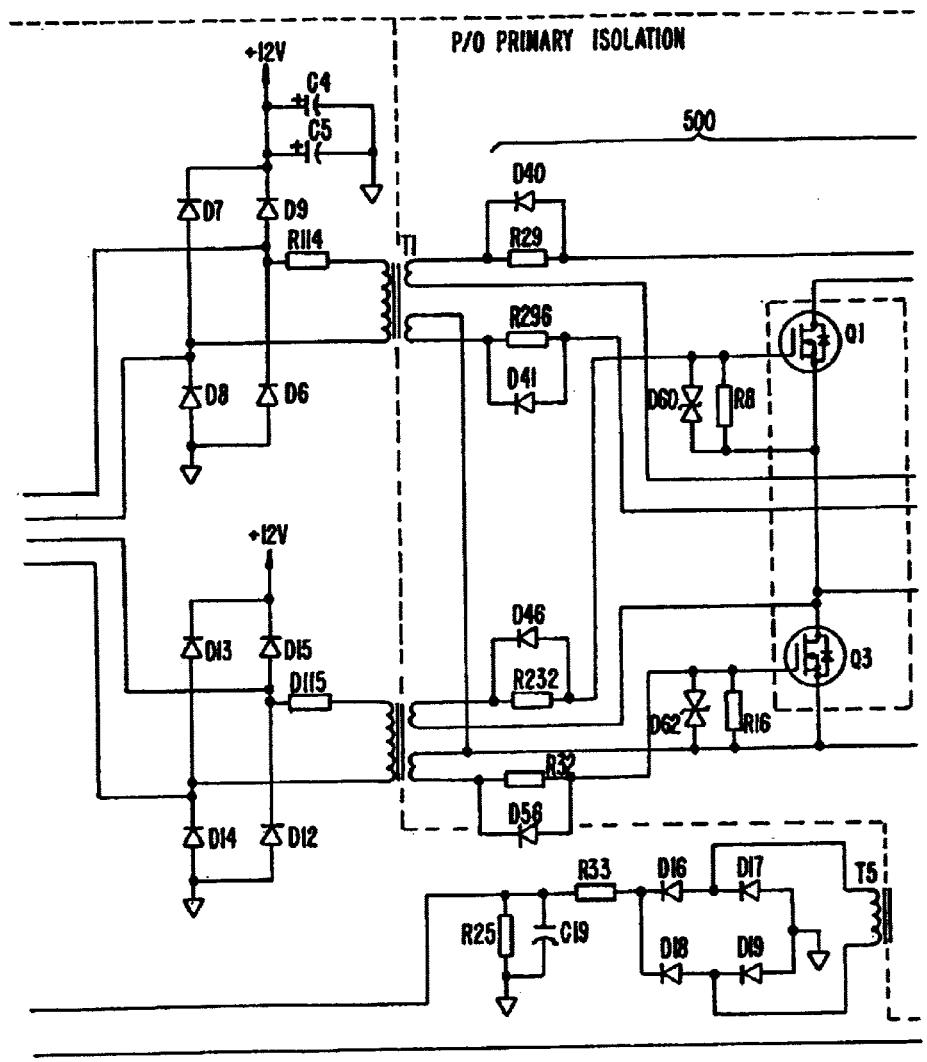
Figure 17C:
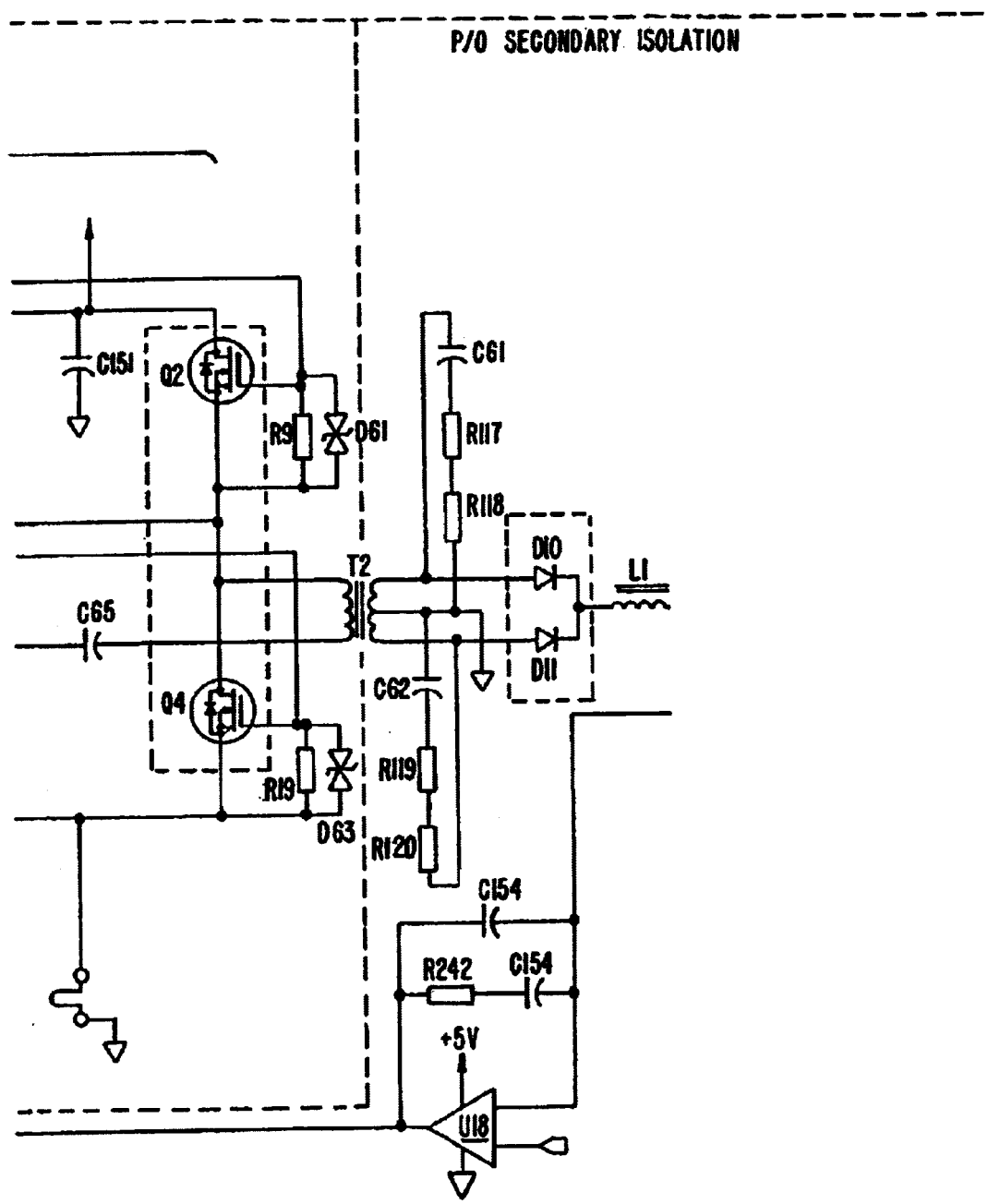

FIGS. 17A–C show an exemplary embodiment of power limiting device 300. The circuit diagram shows that overcurrent is sensed by T5. It is rectified and filtered by D16, D17, D18, D19, R33, and C19 etc. The rectified and filtered signals are fed into voltage comparator 308 which determines if power threshold has been reached. The output of voltage comparator 308 is fed into the FPGA which controls the power supply to the power limiting mode (e.g. it turns on DC/DC converter 10 ms on and 90 ms off). Device 300 includes a converter of a full-wave bridge arrangement with all four switching elements driven by a single transformer. It is capable, through the antiparallel diodes within the MOSFETs, of four-quadrant operation, returning reactive load energy to the power supply for self-protection. 100 kHz sync arrives as 500 nanosecond pull-up pulses from a differentiation network connected to the FPGA. The FPGA also exerts direct on/off control via DC_EN. The output smoothly ramps to regulation when allowed by the FPGA. Options for current limiting are provided. Both linear and digital (pulsatile) limiting are possible. Current limits may also respond to FPGA commands and change under logic control. The inverter is running at zero voltage switching mode to reduce EMI and indirectly reduces leakage current. A cycle-by-cycle current limit circuit serves to protect the switching elements from energy stored in filter and bypass capacitors. Cycle-by-cycle current limit control is applied by the FPGA removing the gate drive. The inverter runs at a fixed 50% duty cycle whenever drive (of about 100 kHz or other) from the FPGA is available. The inverter is running at zero voltage switching mode to reduce EMI and indirectly reduces leakage current.

The power supply of the present invention may also include a spark limiting device 330 (FIG. 18) to prevent sudden current spikes which may char or otherwise damage the electrosurgical instrument and surgical target site. For example, when an instrument attached to the power supply touches a metallic object, the impedance encountered by the instrument (relative to human tissue) decreases suddenly and this undesirably draws a large amount of current from the power supply. This sudden current increase may create sparks between the probe and the metal object. The large amount of current passing through the probe will likely char items along the electrical pathway and may melt electrodes on the electrosurgical instrument.

Figure 18:
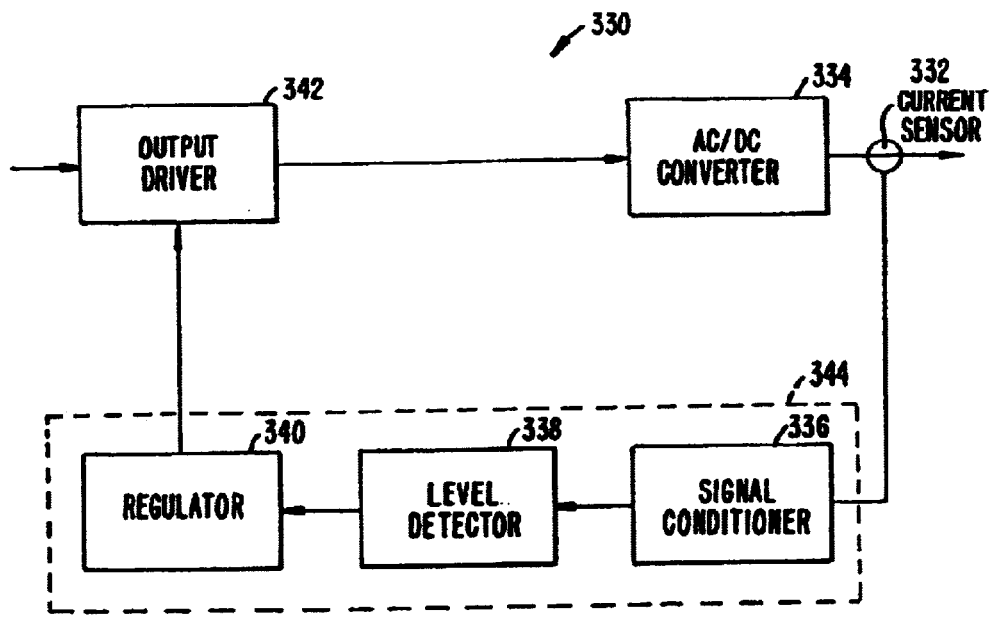
FIG. 18 is a block diagram of a spark limiting device according to the present invention.
Figure 19:
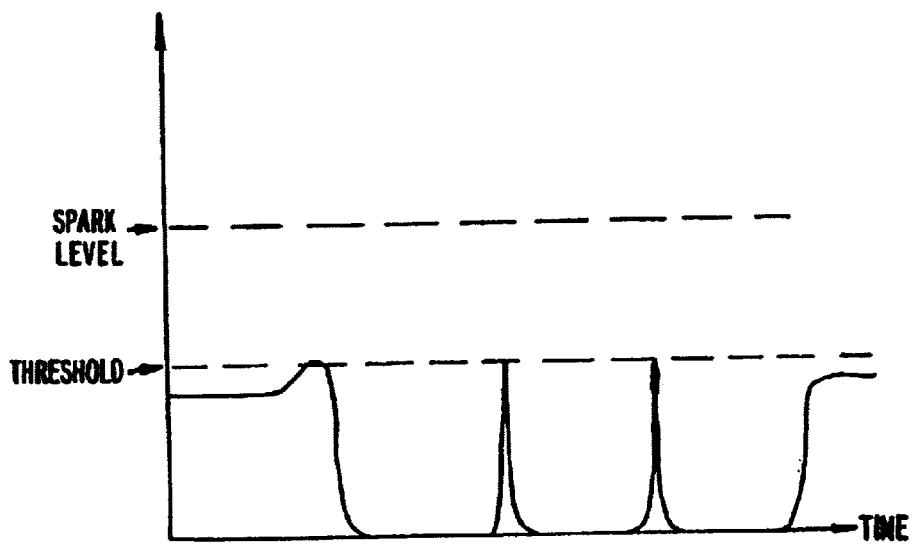
FIG. 19 is a chart of the current output of a spark limiting device according to the present invention.

Referring now to FIG. 18, the spark limiting device 330 will be described in detail. In general terms, the spark limiting device 330 will reduce current output to zero when an extremely low impedance source such as a metal screw or a metal cannula or stent creates a high current drawdown. The spark limiting device 330 is located close to the output electrode. This reduces the delay of the device 330 and allows the device to respond more quickly. The spark limiting device 330 is directed to reduce current output to prevent sparking, not total power output. Although the block diagram of FIG. 18 appears similar to that of the power limiting device 300 (FIG. 13), the spark limiting device 330 is not a fixed periodical pulsing circuit of the type described with reference to FIG. 17. The spark limiting device 330 preferably processes continuous signals, such as analog signals, from the current sensor 332. The spark limiting device 330 continuously monitors current fluctuations of the power output of converter 334 (typically an AC/DC converter). The continuous flow of signal in the spark limiting device 330 allows it to detect the sudden increase in current almost instantaneously and almost certainly before the isolated, power limiting device 300. Current output is preferably turned off after an overcurrent is detected.

The current output during normal therapeutic operation may be in the range of 0.2 amperes or less. The spark limiting device 330 preferably interrupts output when current exceeds about 1.0 to 3.0 amperes. These current levels are insufficient to cause sparking, but enough to warrant concern over potential sparking. When current exceeds levels higher than those stated, the device 330 will preferably prevent any current output from the instrument. The output of the power supply is similar to that shown in FIG. 19. In one embodiment, the spark limiting device 330 has a built-in delay device that turns off current output for a duration of 2–90 ms. Preferably, the delay is programmed into the FPGA. At the end of the delay period, the device 330 will allow current to flow through the probe, albeit at extremely low power, to detect if the extremely low impedance state still exists. If current again exceeds the threshold level of about 1.0 to 3.0 amperes (FIG. 19), the device 330 will zero the output of the power supply and pause for the built-in delay. This delay acts in some ways to give the spark limiting device 330 a duty cycle-like operation.

It should be understood that although it is preferred that no current, preferably, is being emitted from the probe during the delay period, the power supply does not shutoff. This is a particularly useful feature in that it eliminates down time associated with restarting the power supply from power-off. As soon as the probe is removed from the area of extremely low impedance, the spark limiting device 330 will allow power to flow from the RF probe as usual. Preferably, as long as the probe is exposed to the low impedance source, the device 330 will not allow power to be transmitted. Of course, it may be possible to configure the spark limiting device 330 to allow a low level of current to be emitted, versus shutting off the power output completely.

Figure 20:
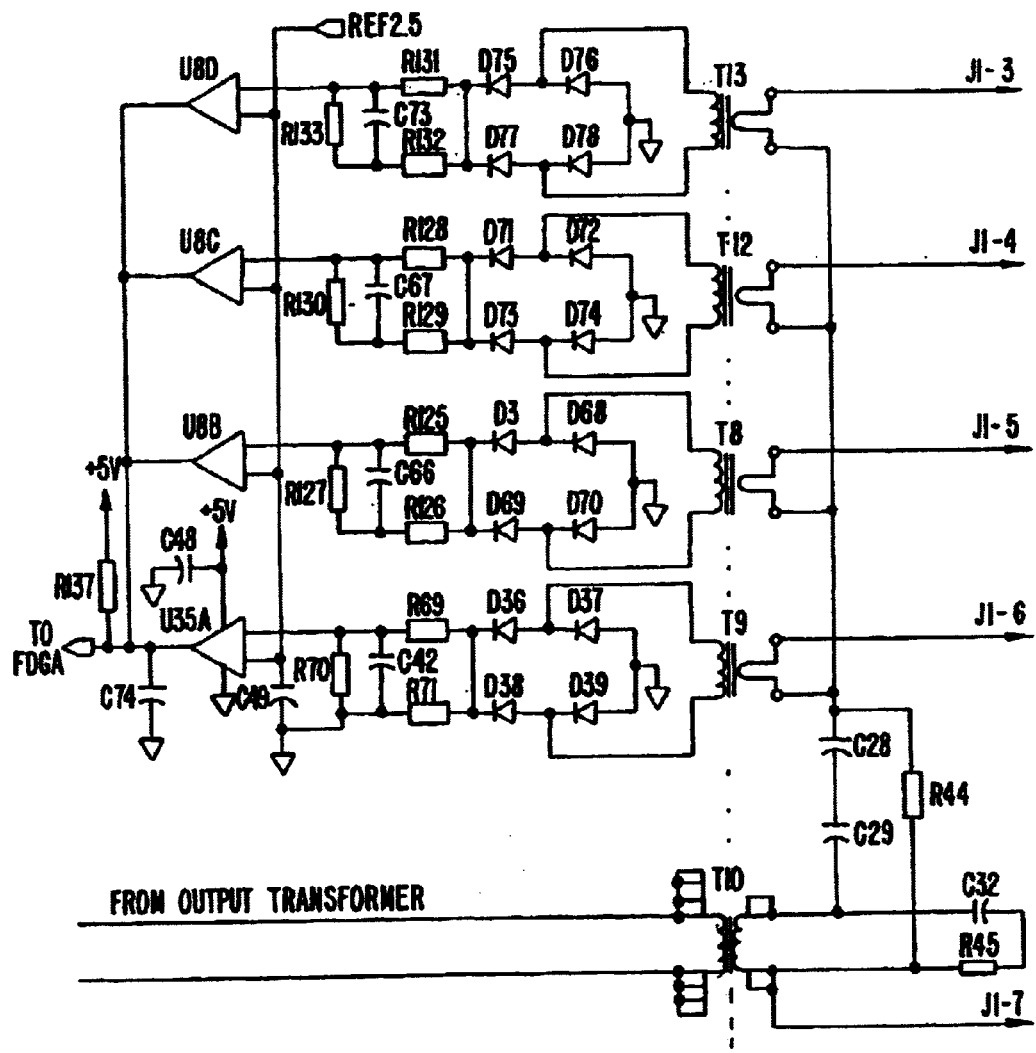
FIG. 20 is a circuit schematic of an exemplary embodiment of a spark limiting device.

The block diagram of FIG. 18 shows that the spark limiting device 330 includes a signal conditioner 336, a level detector 338, a regulator or logic unit 340, and an output driver 342 (such as an RF source known in the art). Although the preferred embodiment of the spark limiting device 330 is based on analog signals, it should be understood that the device 330 may be adapted to use analog signals or digital signals with extremely short duty cycles to approximate a continuous system. The logic unit 340, level detector 338, and signal conditioner 336 may all be combined into a single device or processor as indicated by the dotted line 344. The same may also apply to the power limiting device 300 which has components that may be integrated together. Referring to FIG. 20, a circuit diagram of the spark limiting device 330 is shown. The current sensors 332 are denoted by elements T8, T9, T12, and T13. The diodes D36–D76 and resistors/capacitors R131–R133/C73 etc. are used to condition the analog signal to remove noise and other undesirable qualities. A voltage comparator U8D and the FPGA, corresponding to level detector 338 and logic device 340, are used to determine if the output current detected by sensor 332 is above a predetermined level.

Figure 21:
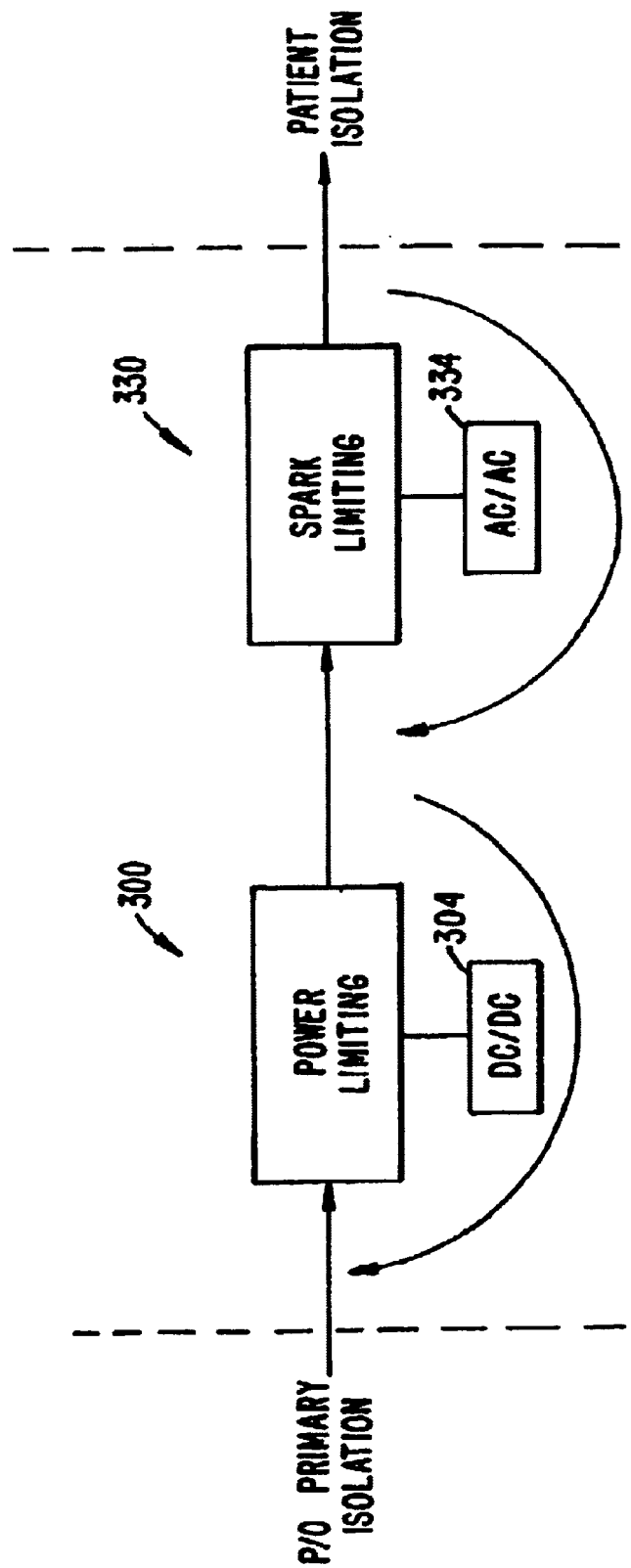
FIG. 21 is a block diagram of the relationship between power limiting and spark limiting devices.
Figure 22A:
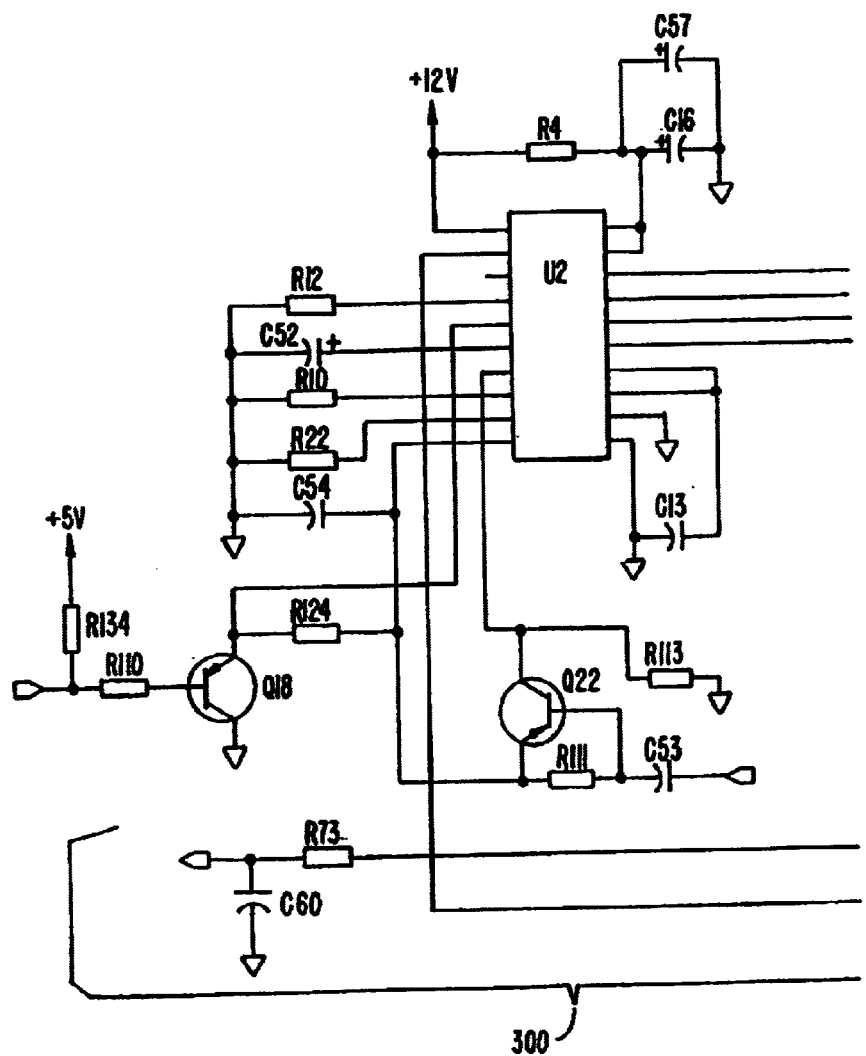
FIGS. 22A–E show a circuit schematic of both the power limiting and spark limiting devices.
Figure 22B:
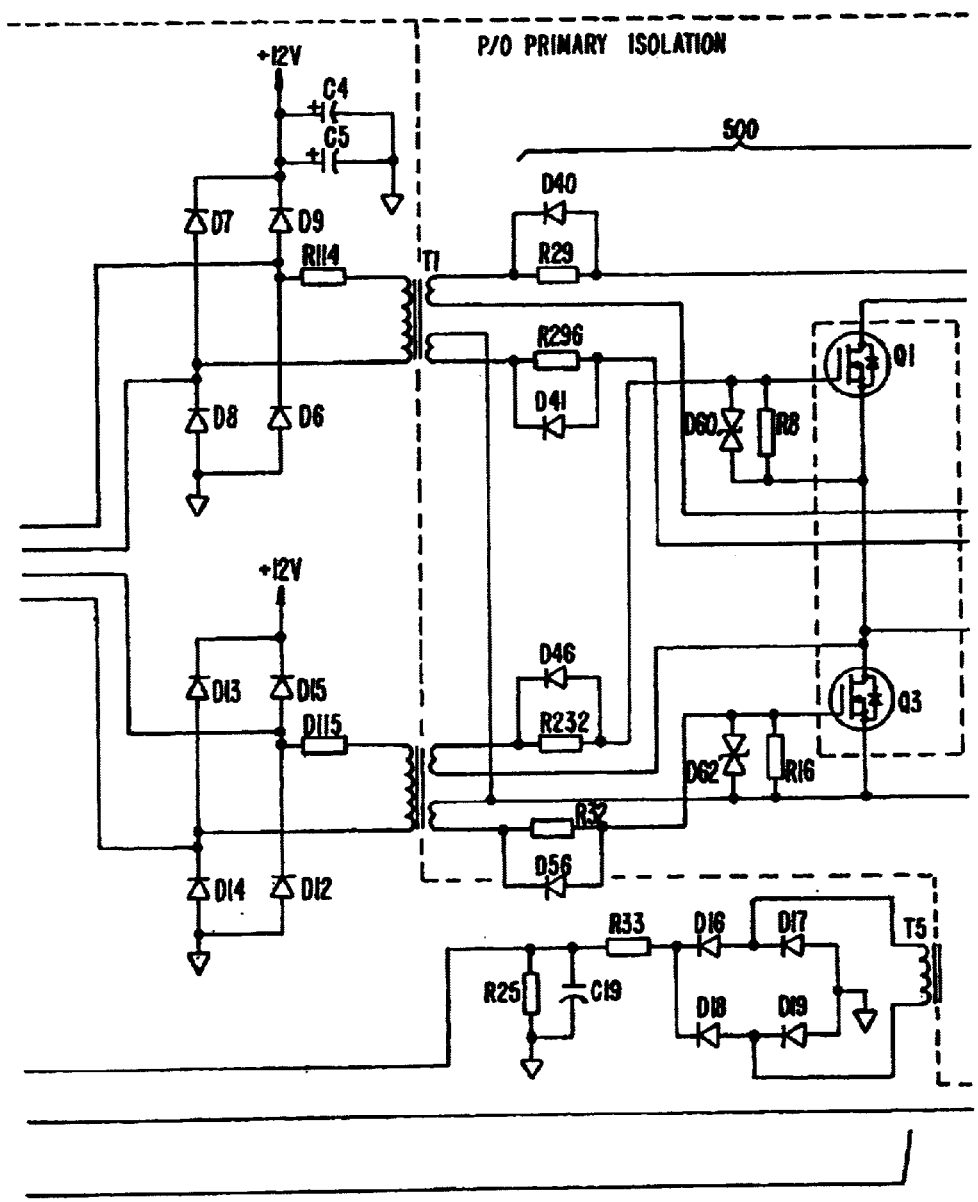
Figure 22C:
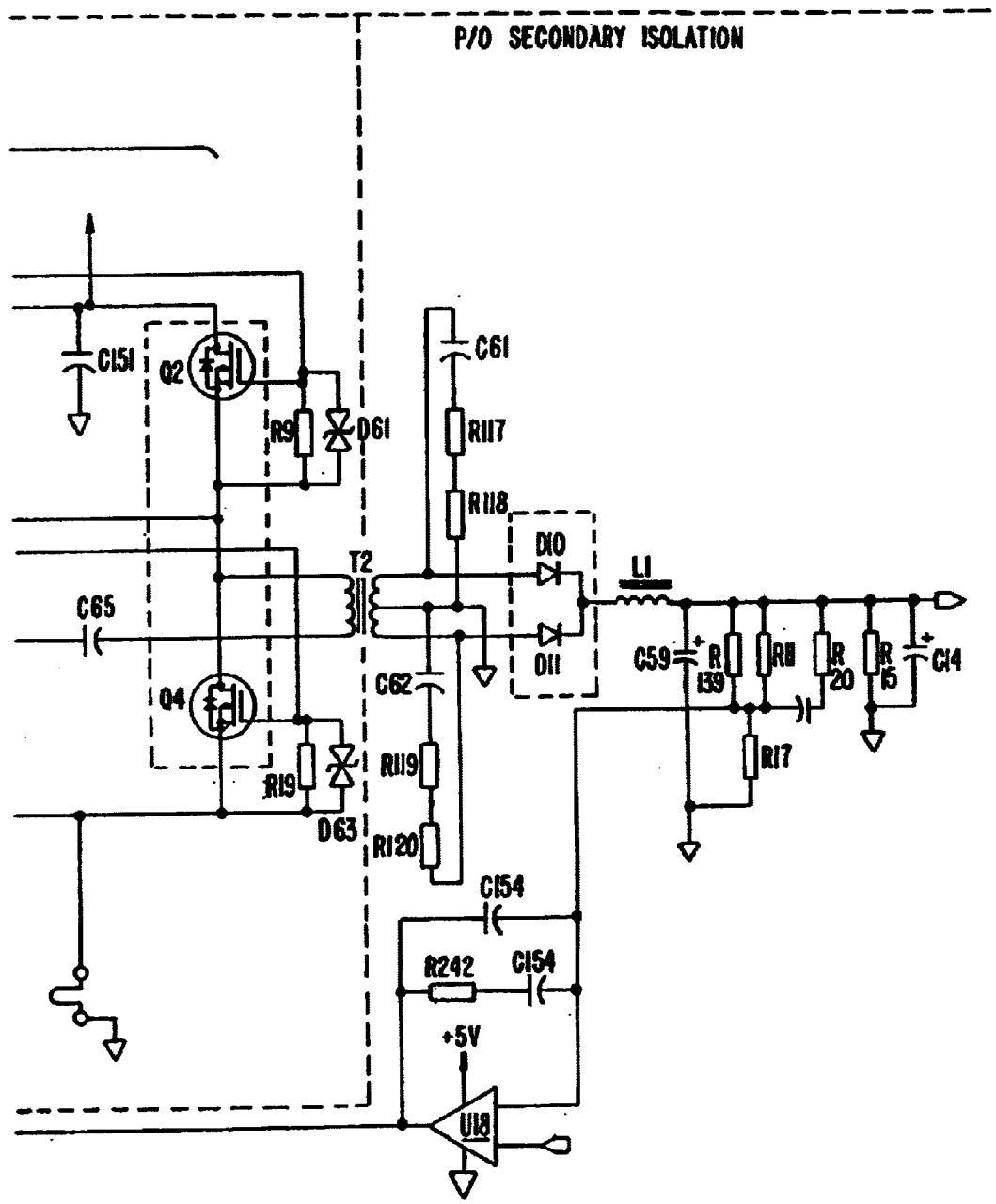
Figure 22D:
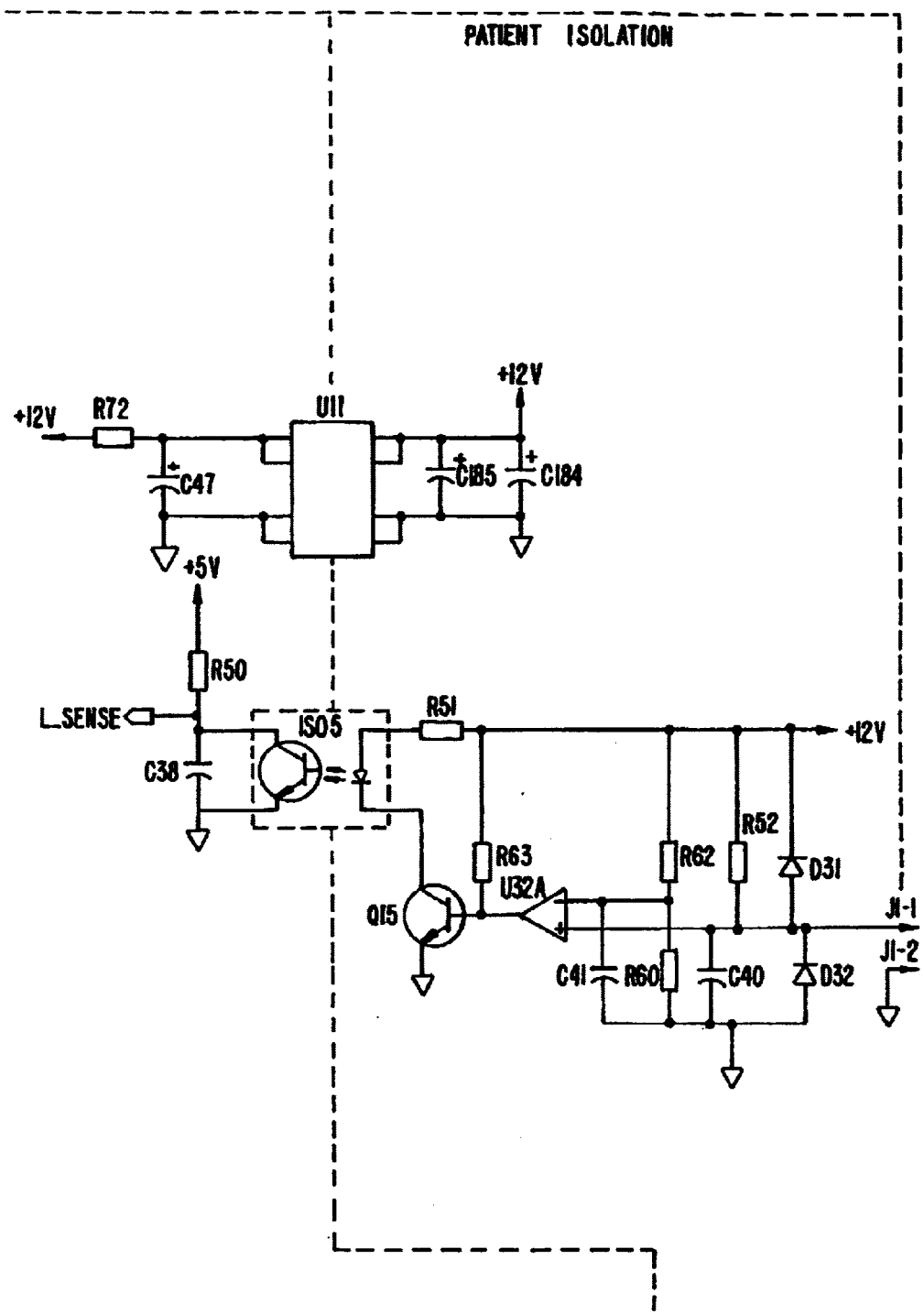
Figure 22E:
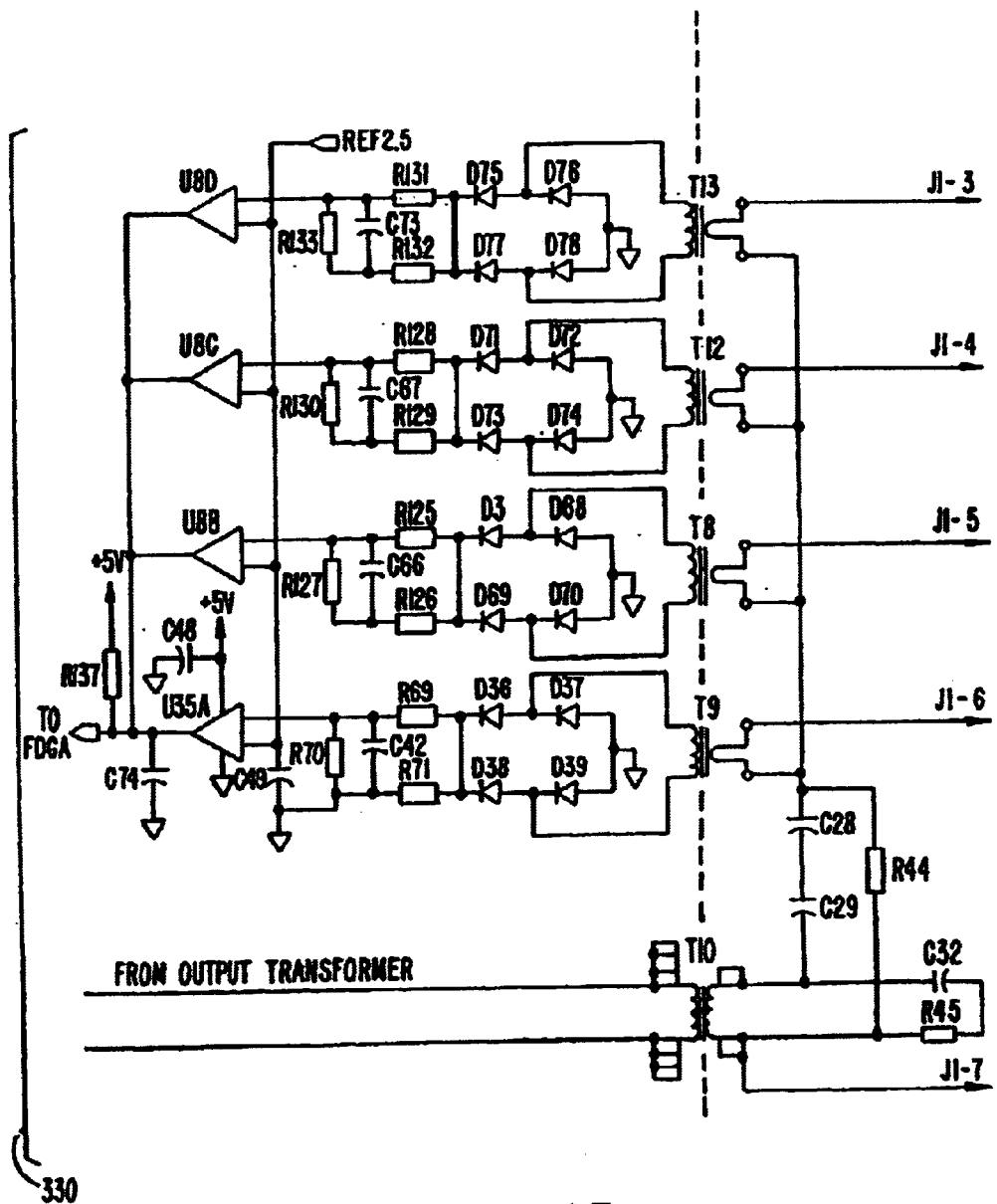
Figure 22:
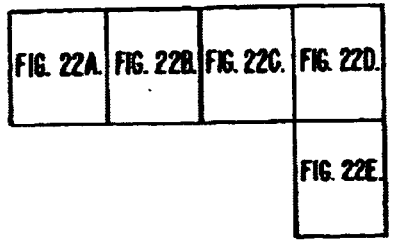

Although the power limiting device 300 and the spark limiting device 330 may be used individually, it is understood that the two devices may also be used concurrently in the power supply. In a preferred embodiment, the power supply of the present invention has the power limiting device 300 and the spark limiting device 330 arranged in a serial configuration as shown in FIGS. 21, 22A–E. This configuration provides for the circuit isolation mandated by safety regulations for medical device power supplies. As shown in FIG. 21, the power supply has P/O primary isolation, P/O secondary isolation, and patient isolation. Using devices 300 and 330 also provides protection for both converters (DC/DC and DC/AC) used to provide stability of the power output. Due to the various isolation barriers required to meet safety and regulatory standards for medical device power supplies, the spark limiting device 330 is typically located closer to the electrode output while the power limiting device 300 is more isolated from the electrode output. The additional amount of isolation circuitry introduces a lag time into the responsiveness of the power limiting device. Thus, one device reacts slower while the device closer to the electrode reacts faster. In one embodiment, there is about a 200 ms delay in order for the current to reach the power limiting device 300.

As an example of how the devices 300 and 330 would function together, when an attached RF catheter touches a metallic object, such as a stent within a body passage, the spark limiting device 330 activates to reduce the current output from the power supply to zero. The current output may be reduced to some nonzero value so long as sparks are not generated. The spark limiting device 330 introduces a delay and then checks to see if it can power up. During this time, the power limiting device 300 also continues to check about every duty cycle to see if power should be increased. In one embodiment, the power limiting device 300 introduces more delay into the system since its duty cycle is longer than the 2–90 ms delay of the spark limiting device 330. As soon as the probe is removed from the extremely low impedance site and current drawdown stays within acceptable ranges, the probe resumes normal operations. If the catheter is no longer in contact with target tissue, then the power supply will most likely be in pulsatile mode while awaiting to be repositioned.

Referring again to FIG. 1, conductive fluid 30 is provided to tissue ablation region 8 of catheter 6 via a lumen (not shown in FIG. 1) within catheter 6. Fluid 30 is supplied to the lumen from the source 100 along a conductive fluid supply line 102 and a conduit 103, which is coupled to the inner catheter lumen at multi-lumen fitment 114. The source of conductive fluid (e.g., isotonic saline) may be an irrigant pump system (not shown) or a simple gravity-driven supply, such as an irrigant reservoir 100 positioned several feet above the level of the patient and tissue ablating region 8. A control valve 104 may be positioned at the interface of fluid supply line 102 and conduit 103 to allow manual control of the flow rate of electrically conductive fluid 30. Alternatively, a metering pump or flow regulator may be used to precisely control the flow rate of the conductive fluid.

System 2 further includes an aspiration or vacuum system (not shown) to aspirate liquids and gases from the target site, as well as syringes 106, 108 for inflating distal and proximal balloons 18, 40, respectively. By way of example, as the plunger of syringe 108 is depressed, fluid in the syringe chamber is displaced such that it flows through a conduit 107 and an internal lumen 57 within catheter 6 (not shown in FIG. 1) to expand and inflate balloon 40. Likewise, syringe 106 is provided at the proximal end of guide wire 28 for inflating distal balloon 18, as shown by translation vectors 116, 118. Also, guidewire 28 can be advanced or retracted relative to tissue ablation region 8 of catheter 6 as shown by translation vectors 116, 118 such that, for each increment of relative displacement 116 at the proximal end of catheter 6, there is a corresponding displacement 118 of the hollow guidewire 28 relative to the tissue ablating region 8 of catheter 6.

Figure 2B:
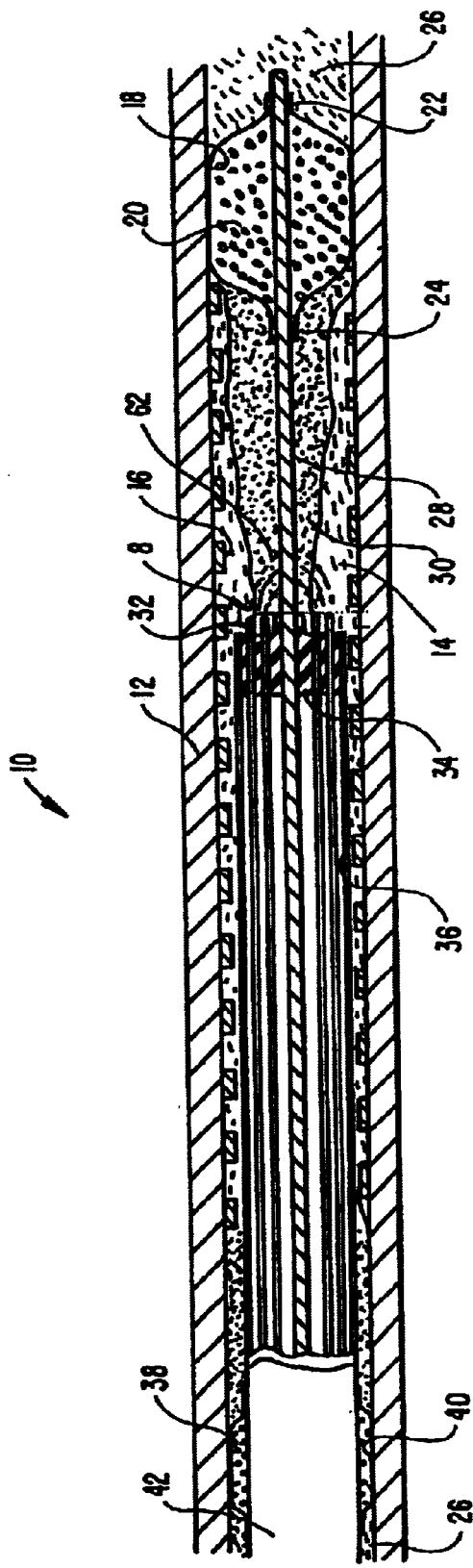
Figure 2C:
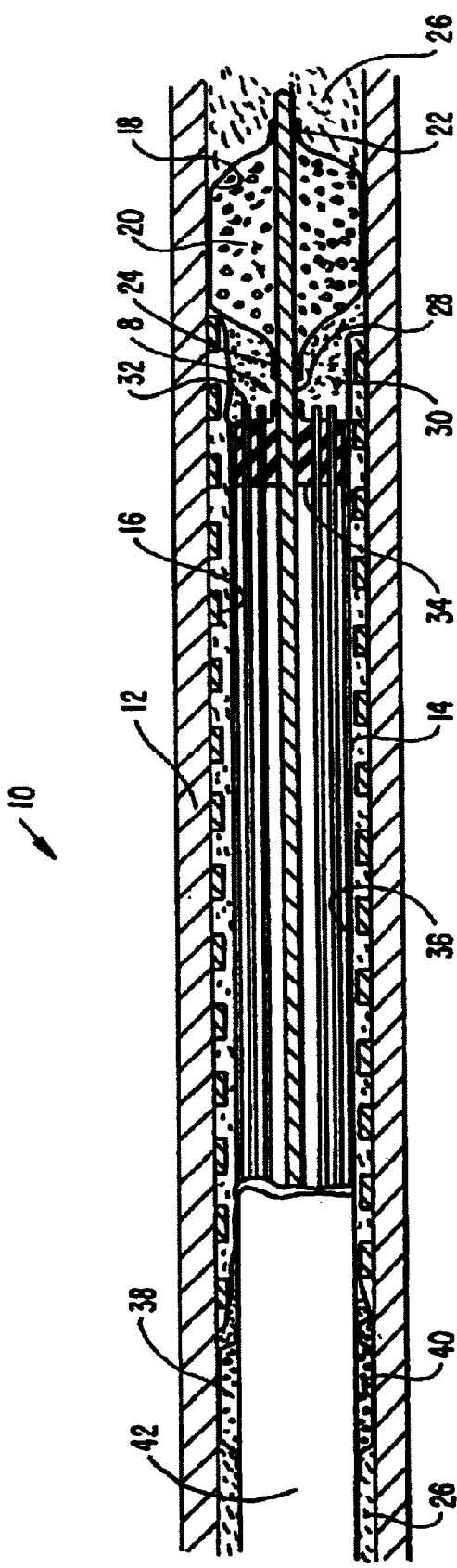

Referring now to FIGS. 2A–2C, one embodiment of the method and apparatus of the present invention will be described in detail. As shown, tissue ablating region 8 of catheter 6 progresses through occlusive media 14, such as atheromatous media or thrombus within a body lumen 10, e.g., a blood vessel. The principles of the present invention are also applicable to any body lumen which becomes partially or totally occluded. The present invention is particularly useful in a lumen containing a lumenal prosthesis, such as a stent 16, stent-graft or graft, which may be metallic, non-metallic, or a non-metallic coated metallic structure. A particular advantage of the present invention is the confinement of current flow paths (not shown) between the return electrode (hollow guide wire 28 in the present example) and one or more active electrodes 32 to the vicinity of tissue ablating region 8. This confinement of current flow paths minimizes the undesired flow of current through portions or all of stent 16, which may otherwise induce non-specific tissue injury beyond the site of recanalization of the occluded lumen 10.

Referring to FIG. 2A, tissue ablating region 8 of catheter 6 is positioned proximal to the occlusive media 14 within lumen 10. The distal region of hollow guide wire 28 is positioned distal to the occlusive media 14 either before or after the initial positioning of tissue ablation region 8. Once hollow guide wire 28 is positioned as shown in FIG. 2A, proximal balloon 40 (not shown in FIG. 2A) is inflated to effect a seal between catheter shaft 42 and interior wall 12 of lumen 10 to minimize the flow of bodily fluid 26 (e.g., blood) from regions proximal to the tissue ablating region 8 of catheter 6. Electrically conductive and biologically compatible fluid 30 (e.g., isotonic saline) is delivered into lumen 10 for a sufficient period of time and under a sufficient positive pressure to displace naturally occurring bodily fluid 26 in the region between the tissue ablating region and the distal tip of guide wire 28. After the bodily fluid has been displaced, distal balloon 18 can be inflated to effect a seal between balloon 18 and the interior wall 12 of lumen 10.

The supply of electrically conductive fluid 30 is continuously delivered to region 8 and may be balanced with the aspiration of fluid from the site of intended recanalization. The active electrode(s) 32 is (are) then energized by applying a high frequency voltage between active electrode(s) 32 and return electrode or guide wire 28. A high electric field is created at the surface of active electrode(s) 32 which causes the volumetric removal or ablation or target tissue in close proximity with active electrode(s) 32. The flow of electrical current between return electrode 28 and active electrode(s) 32 is shown by current flux lines 62 in FIG. 2B. As the occlusive media 14 is ablated, gaseous products are generated (not shown) which are entrained in the electrically conductive fluid 30 and removed through aspiration lumen 58 (not shown in FIGS. 2A, 2B). The current flux lines 62 are generally confined to the central portion of tissue ablation region 8 because they generally flow inward towards return electrode 28 and because the occlusive media 14 generally shields the outer region of lumen (including stent 16) from flux lines 62. This minimizes undesirable interaction between the electrical current and stent 16.

Referring to FIG. 2C, this ablation procedure is continued until the desired length of the lumen containing occlusive media is recanalized. During the recanalization process, the products of ablation are confined between proximal balloon 40 and distal balloon 18 to minimize, for example, the injection of any non-condensable gaseous products of ablation into the blood stream which could otherwise lead to the formation of injurious or life-threatening emboli. Once the occlusive media 14 has been volumetrically removed (i.e., ablated), the energy application is suspended, the valve on the aspiration lumen is closed, control valve 104 is closed and balloons 18, 40 are deflated. The time period from the initial inflation of balloons 18, 40 to the deflation of these balloons is typically about 15–45 seconds, depending on the length and the extent of occlusion in the vessel. For longer occlusions, the above process may be repeated several times with intervals of no balloon inflation so that vital oxygen-bearing blood can be reperfused through the zone of intended recanalization to preserve the tissue distal to the recanalization zone.

Figure 3A:
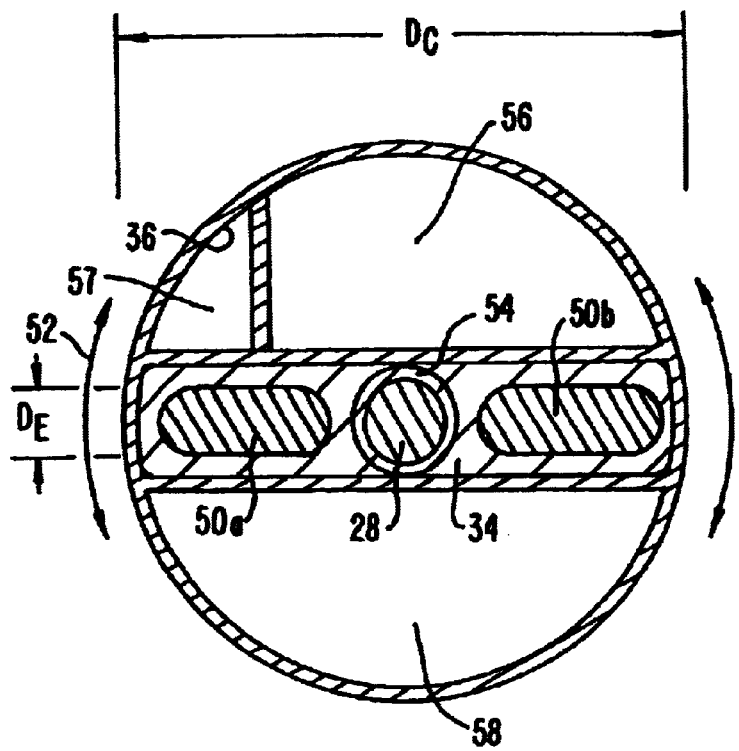
FIGS. 3A and 3B are transverse and longitudinal cross-sectional views, respectively, of a first embodiment of the distal portion of the catheter.
Figure 3B:
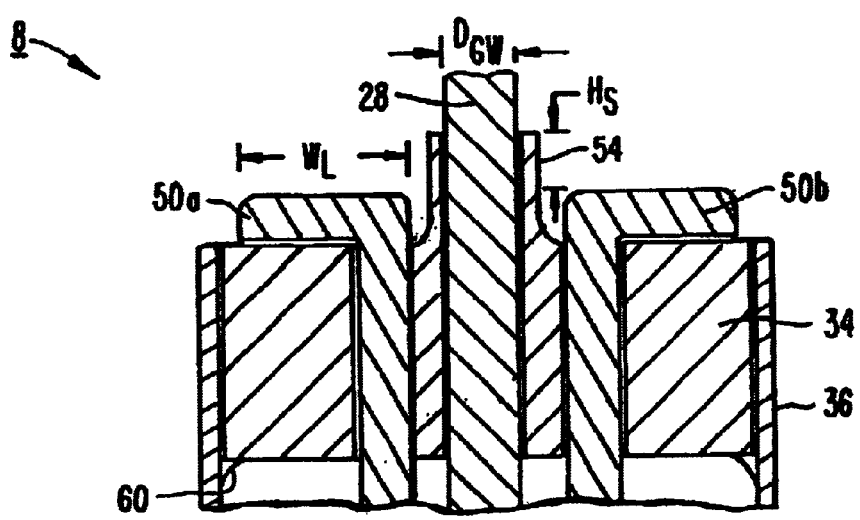

A first embodiment of tissue ablation region 8 of catheter 6 is shown in FIGS. 3A and 3B. As shown, two active electrodes 50a and 50b are secured within an electrically insulating support member 34. The electrodes 50a, 50b are preferably composed of a refractory, electrically conductive metal or alloy, such as platinum, titanium, tantalum, tungsten, stainless steel, gold-plated, copper, nickel, and the like. The support member 34 is secured to the distal end of catheter 6 with a biocompatible adhesive 60 between support member 34 and outer sleeve 36. An electrically insulating sleeve 54 preferably extends above the distal plane of active electrodes 50a, 50b by a distance $H_s$. A central lumen in support member 34 provides a passageway for guide wire 28 that permits axial displacement and rotation of tissue ablating region 8 relative to guide wire 28.

In an exemplary embodiment, the support member 34 will comprise an inorganic insulator, such as ceramic, glass, glass/ceramic or a high resistivity material, such as silicone or the like. An inorganic material is generally preferred for the construction of the support member 34 since organic or silicone based polymers are known to rapidly erode during sustained periods of the application of high voltages between electrodes 50a, 50b and the return electrode 28 during tissue ablation. However, for situations in which the total cumulative time of applied power is less than about one minute, organic or silicone based polymers may be used without significant erosion and loss of material of the support member 34 and, therefore, without significant reduction in ablation performance.

As shown in FIG. 3A, an irrigation lumen 56 and an aspiration lumen 58 are provided to inject electrically conductive fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40. Alternatively, the fluid lumen 57 may terminate within the proximal balloon 40.

In use with the present invention, catheter 6 is rotated approximately 180 degrees clockwise and then approximately 180 degrees counter clockwise as the electrodes 50a, 50b are energized by power supply 80 (FIG. 1) to effect ablation of the occlusive media. Using a reciprocating rotational motion combined with a small amount of pressure in the longitudinal direction to advance tissue ablation region 8 through the longitudinal length of the occlusive media 14 allows recanalization of the occluded vessel as described with reference to FIGS. 2A–2C. The cross-sectional shape of the active electrodes may be round wires as shown in FIG. 3B, or they may have shaped surfaces to enhance the electric field intensity at the distal surfaces of the active electrodes 50a, 50b. Suitable electrode designs for use with the present invention may be found in co-pending, commonly assigned application Ser. No. 08/687,792, filed Jul. 19, 1996, the complete disclosure of which is incorporated herein by reference for all purposes.

Return electrode 28 comprises an electrically conducting material, usually a metal, which is selected from the group consisting of stainless steel alloys, platinum or its alloys, titanium or its alloys, molybdenum or its alloys, and nickel or its alloys. The return electrode 28 may be composed of the same metal or alloy which forms the active electrodes 50a, 50b to minimize any potential for corrosion or the generation of electrochemical potentials due to the presence of dissimilar metals contained within an electrically conductive fluid 30, such as isotonic saline (discussed in greater detail below).

Figure 4A:
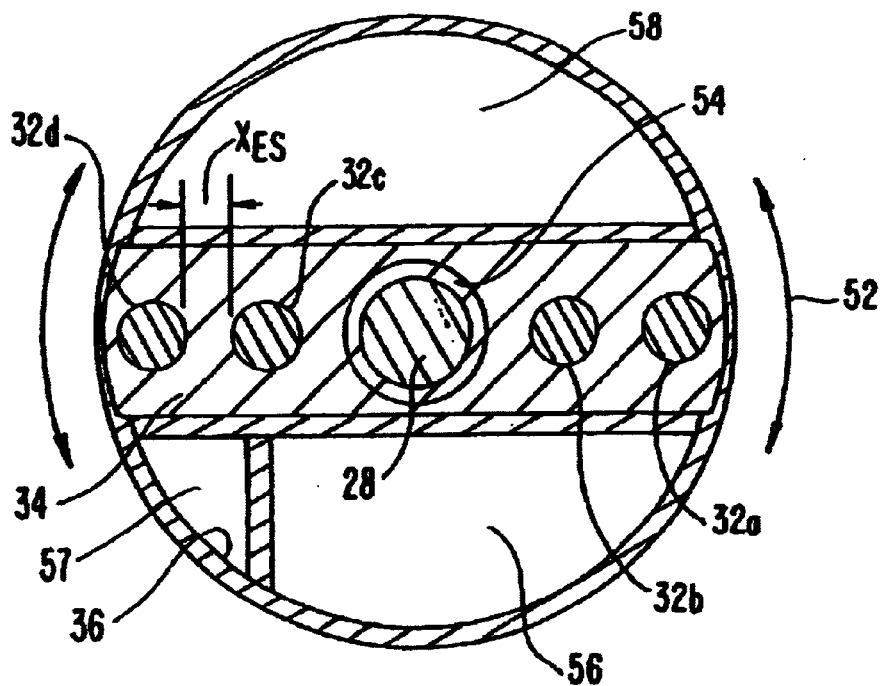
FIGS. 4A and 4B are transverse and longitudinal cross-sectional views, respectively, of a second embodiment of the distal portion of the catheter.
Figure 4B:
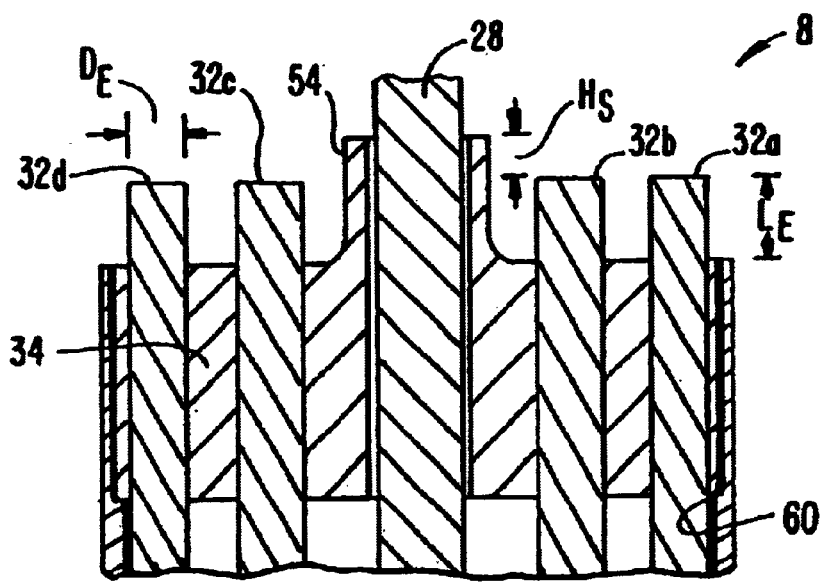

Referring now to FIGS. 4A and 4B, a second embodiment of tissue ablation region 8 of catheter 6 will now be described. In this embodiment, four active electrodes 32*a*, 32*b*, 32*c*, 32*d* are secured within an electrically insulating support member 34. Similar to the previous embodiment, support member 34 is secured to the distal end of catheter 6 with a biocompatible adhesive 60 between support member 34 and outer sleeve 36. An electrically insulating sleeve 54 preferably extends above the distal plane of active electrodes 50*a*, 50*b* by a distance $H_s$. A central lumen in support member 34 provides a passageway for guide wire 28 that permits axial displacement and rotation of tissue ablating region 8 relative to guide wire 28. As shown in FIG. 4A, an irrigation lumen 56 and an aspiration lumen 58 are provided to inject electrically conductive fluid 30 and remove gaseous products of ablation 48 from the site of recanalization. An additional fluid lumen 57 provides fluid communication between inflation syringe 108 and proximal balloon 40. This fluid lumen 57 is filled with a sealant, or terminates, in those portions of the catheter distal to proximal balloon 40.

In use, catheter 6 is rotated approximately 180 degrees clockwise and then approximately 180 degrees counter clockwise as the electrodes 32 are energized by generator 80 (FIG. 1) to effect ablation of the occlusive media. Using a reciprocating rotational motion combined with a small amount of pressure to advance tissue ablation region 8 through the longitudinal length of the occlusive media 14 allows recanalization of the occluded vessel as described with reference to FIGS. 2A–2C. The cross-sectional shape of the active electrodes may be round wires as shown in FIG. 4B, or they may have shaped surfaces to enhance the electric field intensity at the distal surfaces of the active electrodes 32 as described co-pending, commonly assigned application Ser. No. 08/687,792, filed Jul. 19, 1996 the complete disclosure of which has previously been incorporated herein by reference.

Figure 5A:
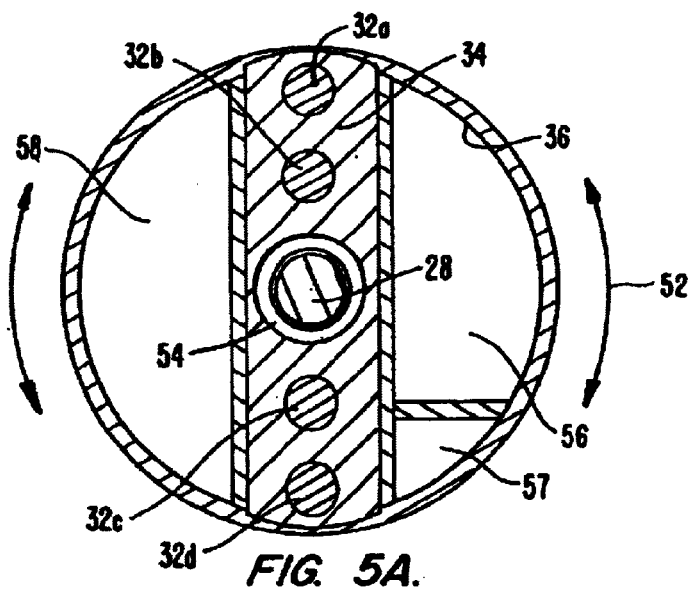
FIGS. 5A and 5B are transverse and longitudinal cross-sectional views, respectively, of the second embodiment of the distal portion of the catheter further illustrating the inflow of conductive liquid and aspiration of conductive liquid and gaseous products.
Figure 5B:
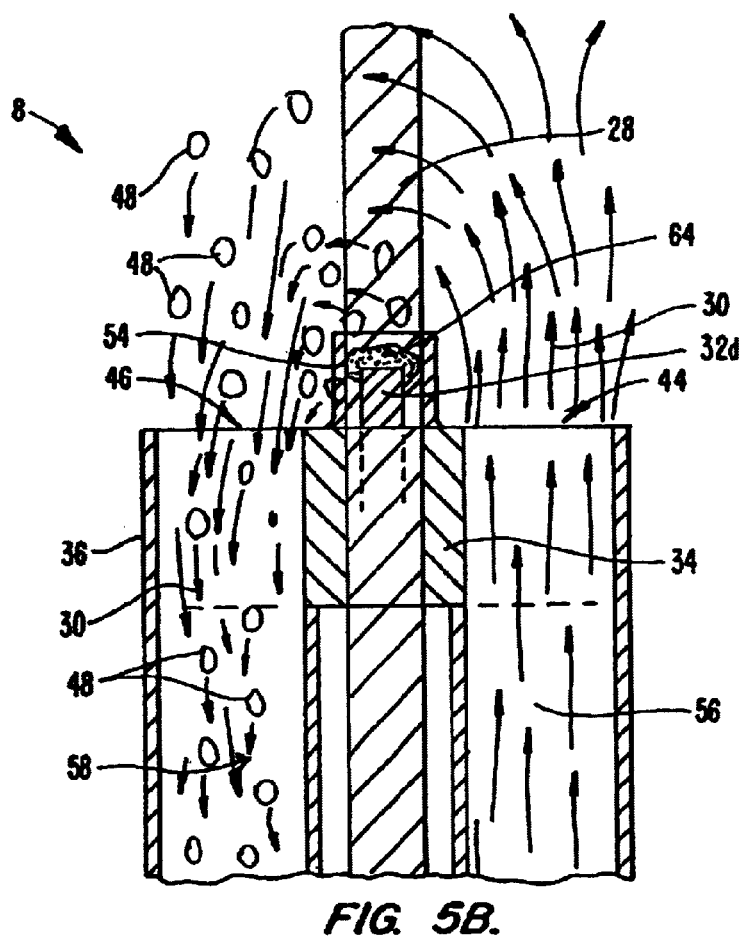

The embodiment of FIGS. 4A and 4B is illustrated in greater detail in FIGS. 5A and 5B. As shown, electrically conductive fluid flows through irrigation lumen 56 of catheter 6 to and through irrigation port 44 and subsequently surrounds the target site (i.e., occlusive media 14). When high frequency voltage is applied between the return electrode 28 and active electrodes 32*a–d*, a vapor layer 64 forms at and around active electrodes 32*a–d* with concomitant volumetric removal (ablation) of the occlusive media 14. A more detailed description of this phenomena can be found in commonly assigned, co-pending application Ser. No. 08/561,958, filed on Nov. 22, 1995 the complete disclosure of which has previously been incorporated herein by reference. The occlusive media 14 is decomposed into gaseous products of ablation 48 which are entrained in electrically conductive fluid 30 and evacuated through aspiration port 46 and to the proximal end of catheter 6 via aspiration lumen 58.

Figure 6A:
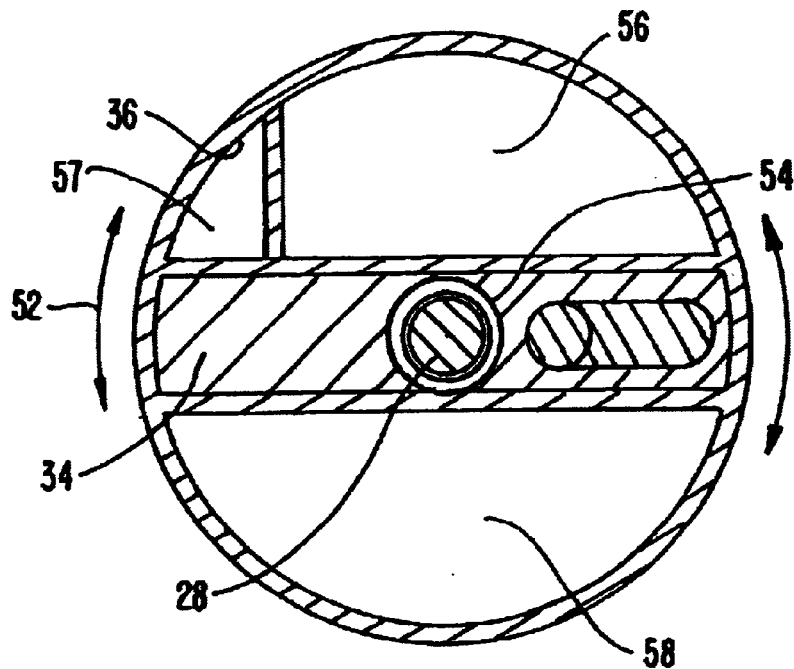
FIGS. 6A and 6B are transverse and longitudinal cross-sectional views, respectively, of a third embodiment of the distal portion of the catheter.
Figure 6B:
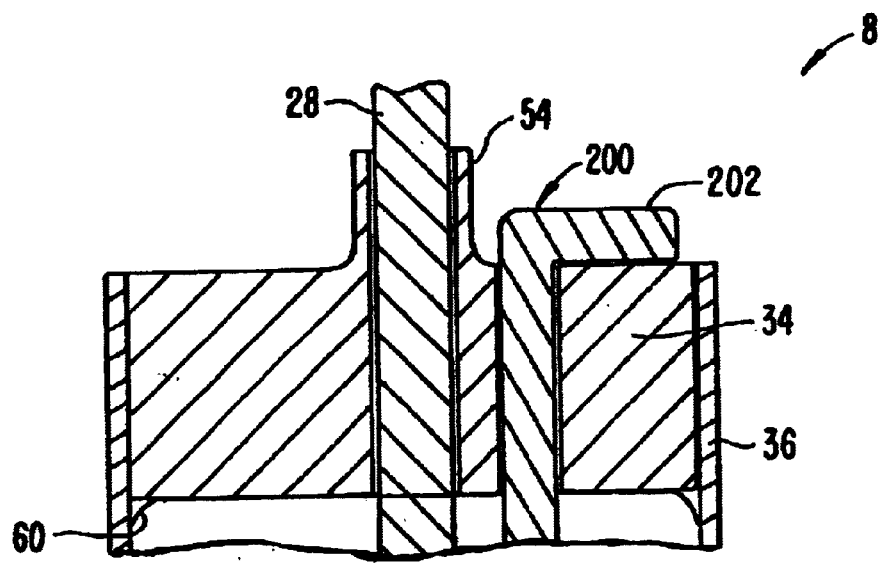

A third embodiment of tissue ablation region 8 is illustrated in FIGS. 6A and 6B. Many of the elements of this embodiment are the same as those of previously described embodiments, and therefore their description will not be repeated. As shown, a single active electrode 200 is secured within support member 34. Active electrode 200 preferably has an L-shaped distal end so that a distal portion 202 of electrode 200 extends radially outward along the distal surface of support member 34. As before, catheter 6/electrode 200 is rotated in both directions, as the region 8 is advanced through the lumen to recanalize the lumen.

Figure 7A:
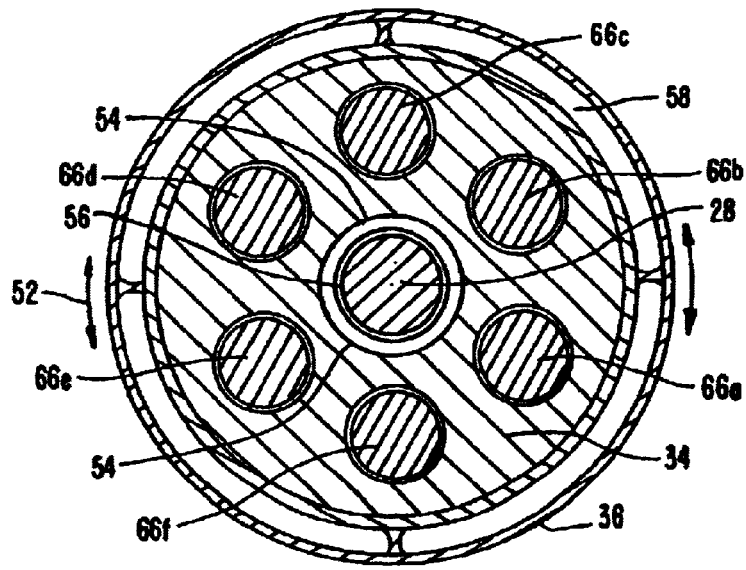
FIGS. 7A and 7B are transverse and longitudinal cross-sectional views, respectively, of a fourth embodiment of the distal portion of the catheter.
Figure 7B:
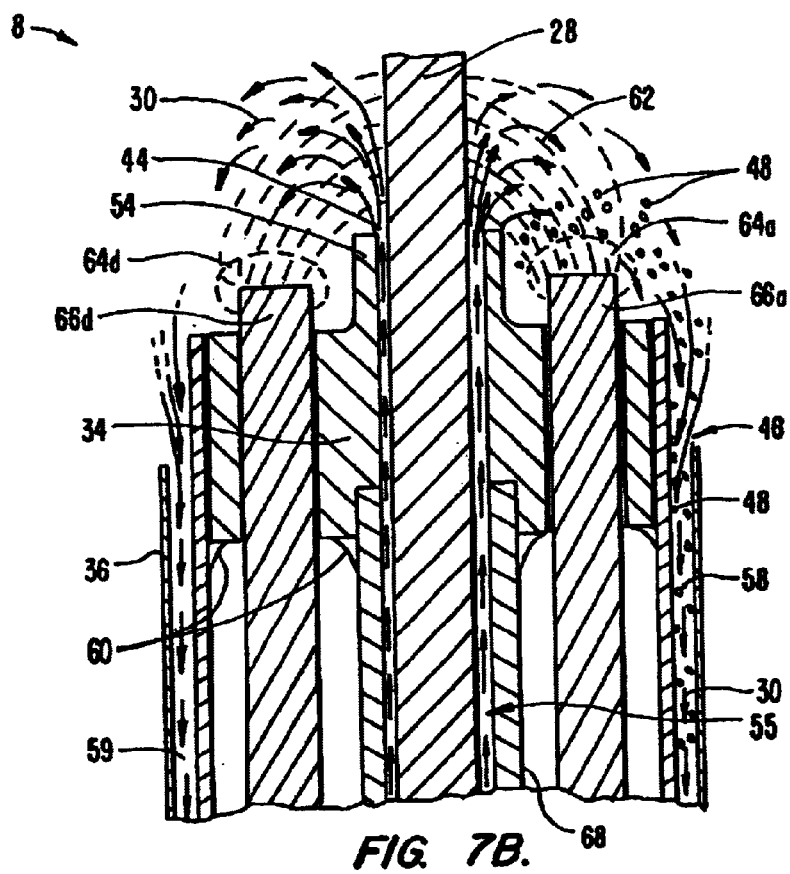

A fourth embodiment of tissue ablation region 8 is illustrated in FIGS. 7A and 7B. Many of the elements of this embodiment are the same as in previous embodiments, and therefore will not be repeated. As shown, six active electrodes 66*a*–66*f* are secured within inorganic support member 34. An annular irrigation lumen 56 and an aspiration lumen 58 are provided to inject electrically conductive fluid 30 and remove gaseous products of ablation 48 from the site of recanalization. When high frequency voltage is applied between the return electrode 28 and active electrodes 66*a–f*, a vapor layer 64 forms at and around active electrodes 66*a–f* with concomitant volumetric removal (ablation) of the occlusive media 14. For this embodiment and that shown in FIGS. 8A and 8B, rotation of catheter 6 may be limited to +/−30 degrees due to the greater number and circumferential distribution of active electrodes. The power or current supplied to each electrode 66*a–f* may be individually controlled by active or passive mechanisms as previously described in commonly assigned, co-pending application Ser. No. 08/561,958, filed on Nov. 22, 1995. The occlusive media 14 is decomposed into gaseous products of ablation 48 which are entrained in electrically conductive fluid 30 and evacuated through aspiration port 46 and onto the proximal end of catheter 6 via aspiration lumen 58. As shown in FIG. 7B, the current flux lines 62 are confined to the central portions of tissue ablation region 8.

Figure 8A:
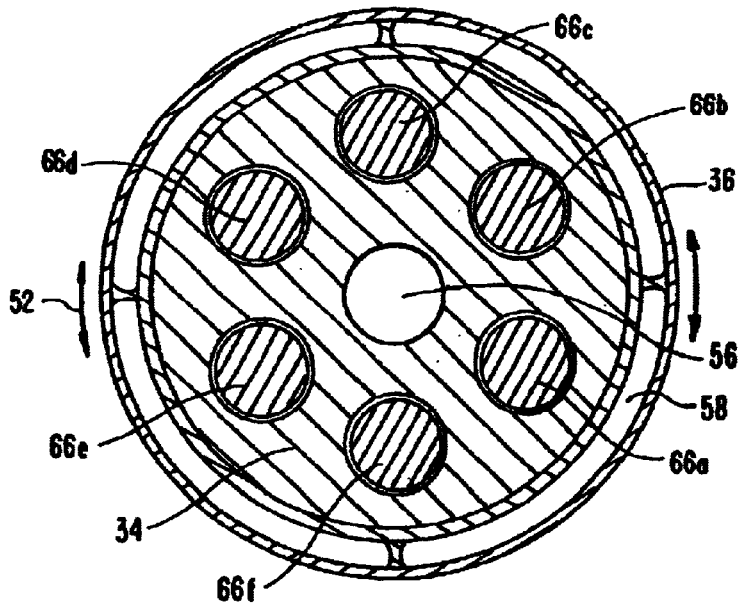
FIGS. 8A and 8B are transverse and longitudinal cross-sectional views, respectively, of a fifth embodiment of the distal portion of the catheter.
Figure 8B:
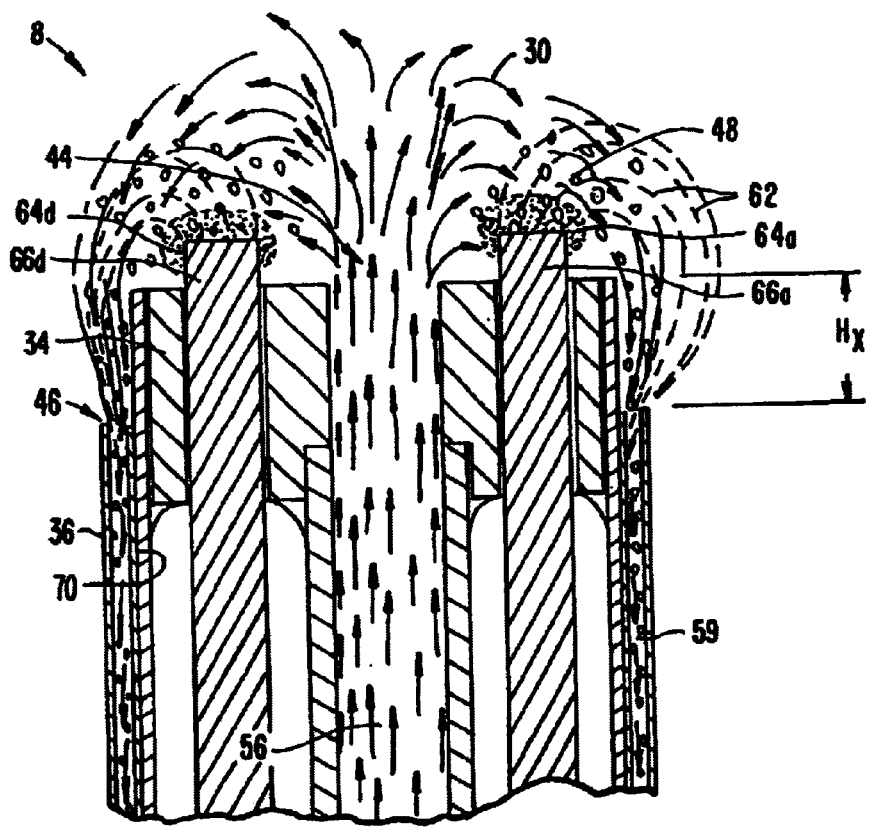

FIGS. 8A and 8B illustrate a fifth embodiment of the present invention. This embodiment is similar to the fourth embodiment in that six active electrodes 66*a*–66*f* are secured within inorganic support member 34. A return electrode 70 (e.g., metal sleeve) is positioned proximal to the active electrodes 66*a*–66*f* by a distance $H_x$. In this embodiment, current flux lines 62 travel proximally from the distal tips of electrodes 66 to the proximally spaced return electrode 70.

Figure 9A:
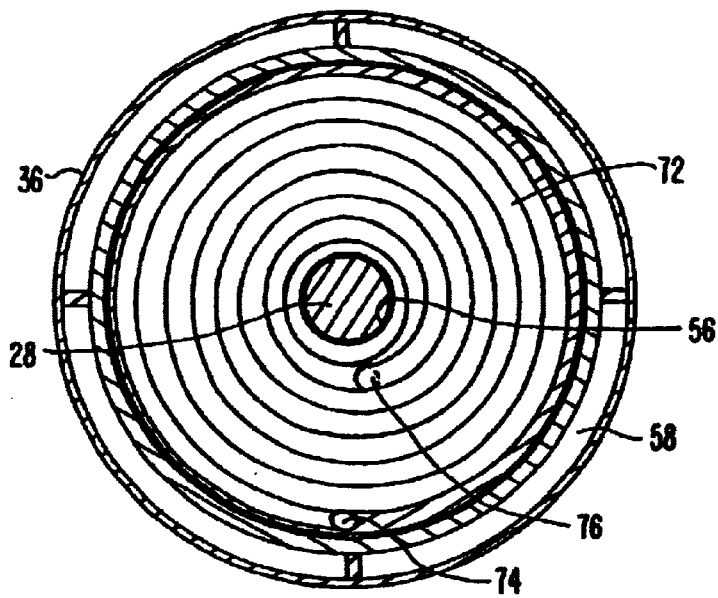
FIGS. 9A and 9B are transverse and longitudinal cross-sectional views, respectively, of a sixth embodiment of the distal portion of the catheter.
Figure 9B:
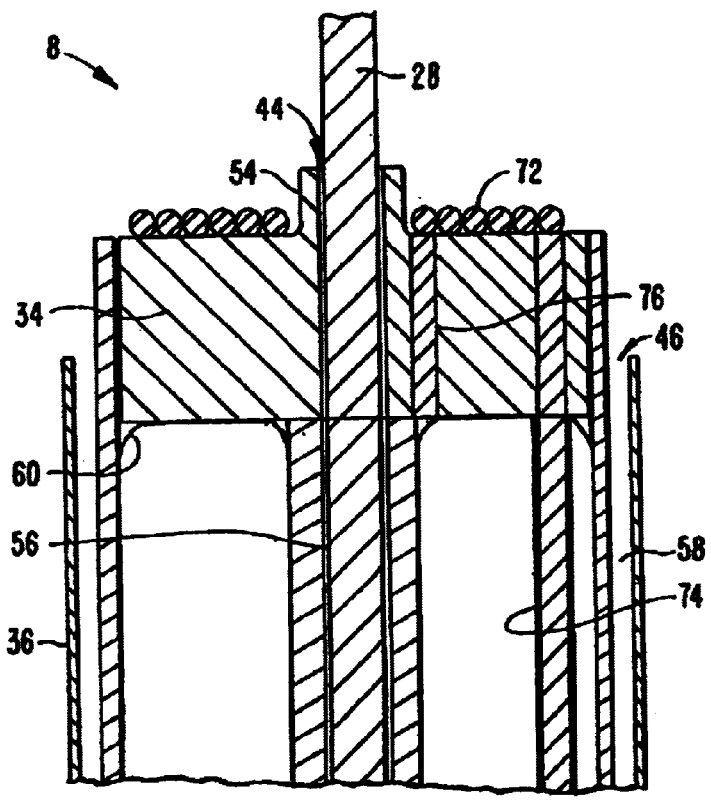

Referring to FIGS. 9A and 9B, a sixth embodiment of the invention will now be described. As shown, a single active electrode 72 is secured within inorganic support member 34. In this embodiment, active electrode 72 comprises a coiled wire having a plurality of concentric coils tightly and helically wrapped and secured on support member 34 (FIG. 9B). Preferably, the helical coil extends around return electrode 28 in concentric configuration, as shown in FIG. 9A.

Figure 10A:
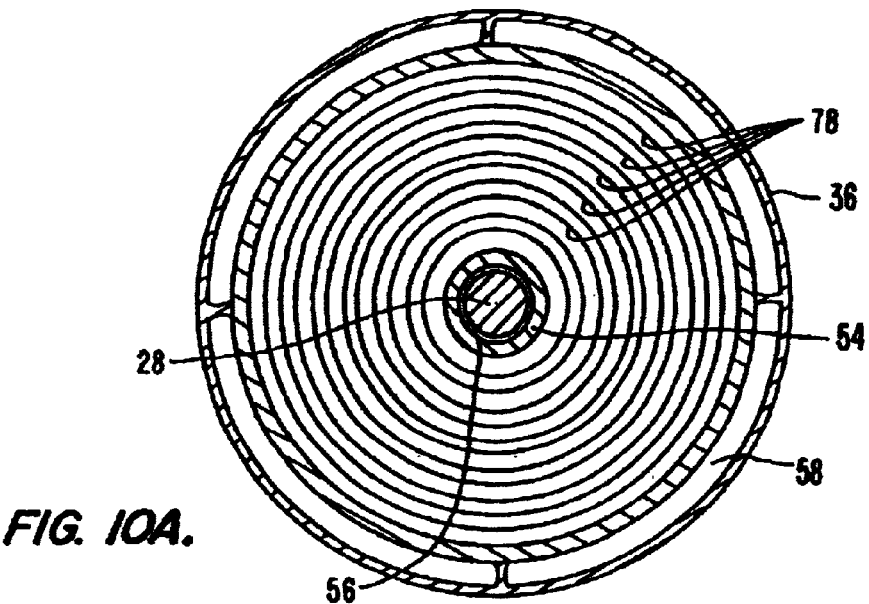
FIGS. 10A and 10B are transverse and longitudinal cross-sectional views, respectively, of a seventh embodiment of the distal portion of the catheter.
Figure 10B:
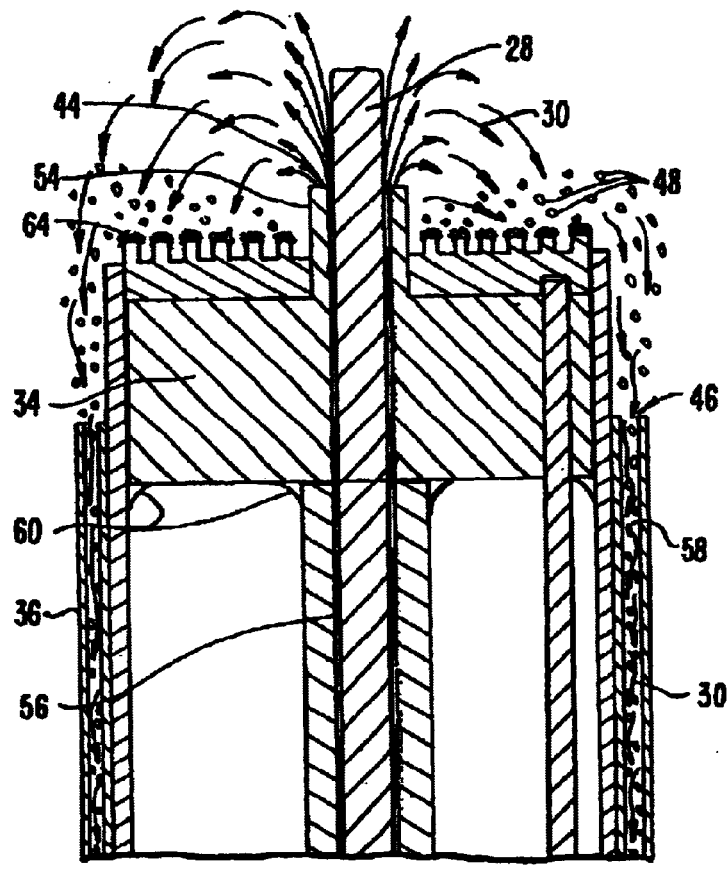

A seventh embodiment of the invention is shown in FIGS. 10A and 10B. This embodiment is similar to the sixth embodiment except that the active electrode defines a series of concentric machined grooves to form concentric circular electrodes 78 surrounding return electrode 28. The distal edges of electrodes 78 generate regions of high electric field intensities when high frequency voltage is applied between return electrode 28 and concentric active electrodes 78. A vapor layer 64 forms at and around active electrodes 78 with concomitant volumetric removal (ablation) of the occlusive media. The embodiments of FIGS. 9 and 10 are usually advanced through the occlusive media without rotation.

In another aspect of the invention, the catheter includes a radially expandable portion for allowing the diameter of the active electrodes to be varied according to the diameter of the body lumen. In some instances, stents will not expand uniformly resulting in portions of the stent having smaller inner diameters. In other instances, vessel wall pressure may cause portions of the stent to spring back to its original shape or partially back to this shape so that the overall inner diameter of the stent varies in the axial direction. Accordingly, the present invention allows the diameter of the working end of the catheter to vary (either automatically in response to the body lumen or stent inner diameter, or through activation by the surgical team) to facilitate advancement through non-uniform stents or body lumens.

Figure 11:
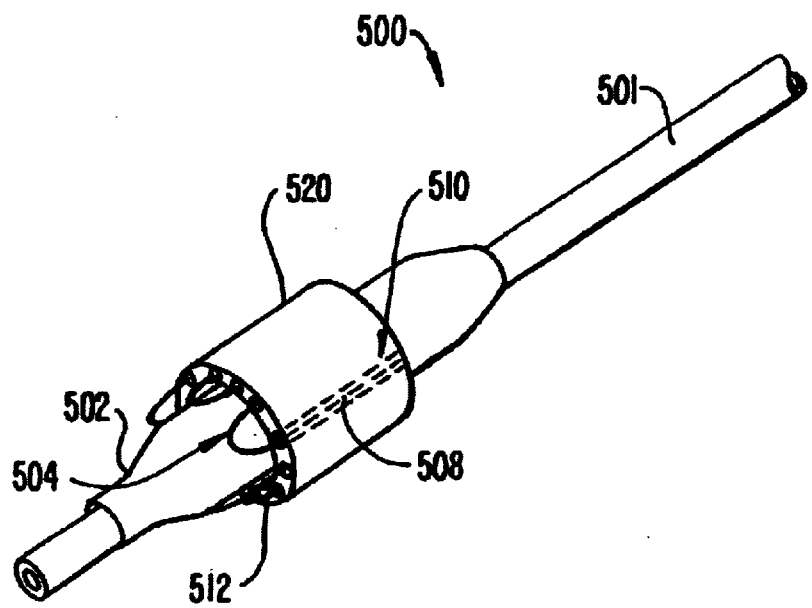
FIGS. 11 and 12 illustrate another embodiment of an electrosurgical catheter incorporating a radially expansible working end.
Figure 12:
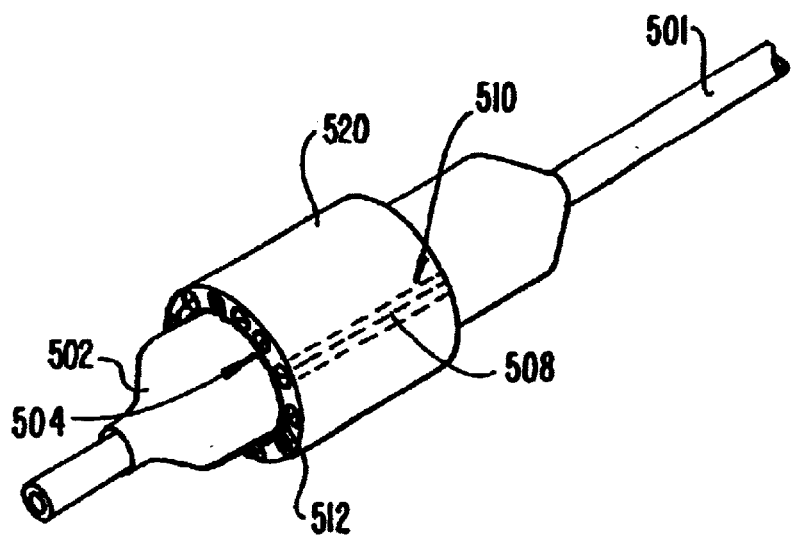

Referring now to FIGS. 11 and 12, a catheter 500 includes a catheter body 501 and a radially expansible working end portion 502 (e.g., a balloon or similar expansible member) supporting a plurality of active electrodes 504 circumferentially spaced around the working end 502. Working end 502 preferably comprises an elastic material that will allow the working end 502 to expand to a diameter at least 25% greater than its original diameter, usually at least 100% greater than the original diameter, and often at least 200% greater than the original diameter (see FIG. 12). As shown, active electrodes 504 are loops 512 formed by a pair of elongate wires 508 extending through tubular support members 510. This configuration provides the distal end of active electrodes 504 with sufficient flexibility to expand outward (the loop straightens in the expanded configuration), as shown in FIG. 12. Of course, active electrodes 504 may comprise a variety of other configurations. In addition, catheter 500 may include a single annular active electrode, as discussed above. Tubular support members 510 preferably comprise an inorganic material, such as ceramic or glass. Support members 510 are loosely coupled to each other with a flexible sheath 520. As the balloon 502 expands (FIG. 12), tubular support members 510 expand away from each other.

In the embodiment of FIGS. 11 and 12, the guidewire (not shown) functions as the return electrode. However, it will be understood that the return electrode may be positioned on the catheter proximal to active electrodes 504, and may be part of the expandable working end 502 of catheter 500. Alternatively, one or more of the active electrodes 504 may serve as the return electrode(s) by applying the opposite polarity to these active electrodes 504.

In other configurations (not shown in the figures), the working end of the catheter will taper in the distal direction (e.g., in a series of steps) so that the surgeon can advance the catheter through a severely occluded body lumen. The catheter may include a series of axially spaced active electrode(s) that are electrically isolated from each other to allow for each set to be independently activated. By way of example, in a severely occluded body lumen, the surgeon may activate the distal set of active electrode(s) to remove the innermost occlusive media, advance these distal active electrode(s) through the vacancy left by the removed occlusive media, and then activate a more proximal, and radially outward, set of active electrode(s) to remove occlusive media radially outward from the initially removed media.

Figure 23:
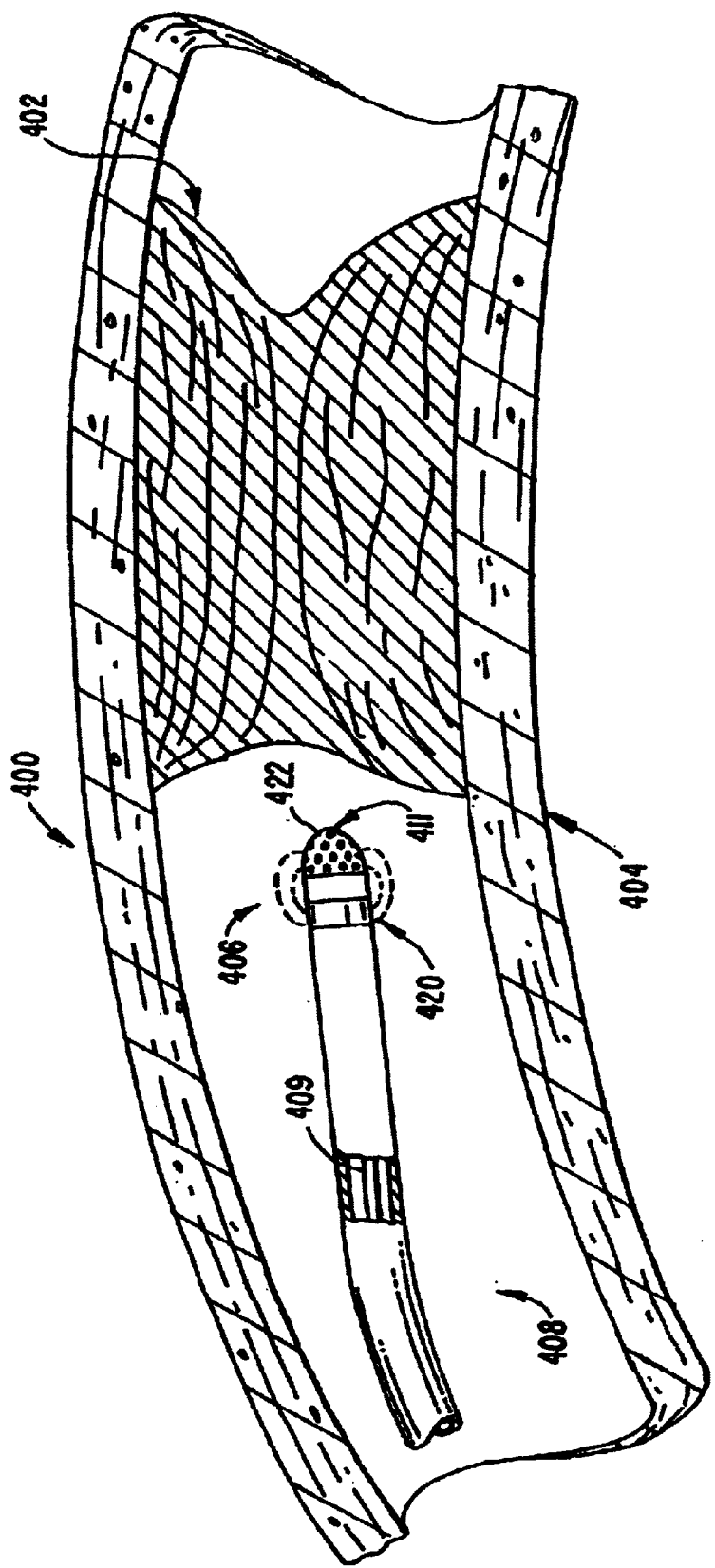
FIG. 23 illustrates a method of volumetrically removing media in a body passage having a total occlusion.

Referring now to FIG. 23, a method for recanalizing a severe occlusion 402 in a body passage 400 will be described. As shown, the occlusion 402 completely blocks the body passage, making it extremely difficult to recanalize with conventional catheter techniques. In these circumstances, it is necessary to at least partially recanalize (creating an opening through) the occlusion before conventional catheter procedures can begin. Conventional methods for recanalizing severe occlusions include hot-tipped catheters, laser catheters, and drill-tipped catheters. These approaches rely on very aggressive treatment of the stenotic material, which can expose the blood vessel wall 404 to significant injury, for example, vessel perforation.

According to the present invention, the working end 406 of an electrosurgical catheter 408 is advanced through the body passage 400 to the site of recanalization. The catheter 408 may be advanced with a variety of techniques, such as a guidewire, steerable catheter and the like. Once the surgeon has reached the point of major blockage, electrically conductive fluid is delivered through one or more internal lumen(s) 409 within the catheter to the tissue. In some embodiments, the catheter may be configured to operate with a naturally occurring body fluid, e.g., blood, as the conductive medium. The fluid flows past the return electrode 420 to the active electrodes 422 at the distal end of the catheter shaft. The rate of fluid flow is controlled with a valve (not shown) such that the zone between the occlusion and active electrode(s) 422 is constantly immersed in the fluid. The power supply 28 is then turned on and adjusted such that a high frequency voltage difference is applied between active electrodes 422 and return electrode 420. The electrically conductive fluid provides the conduction path (see current flux lines) between active electrodes 422 and the return electrode 420.

Figure 24A:
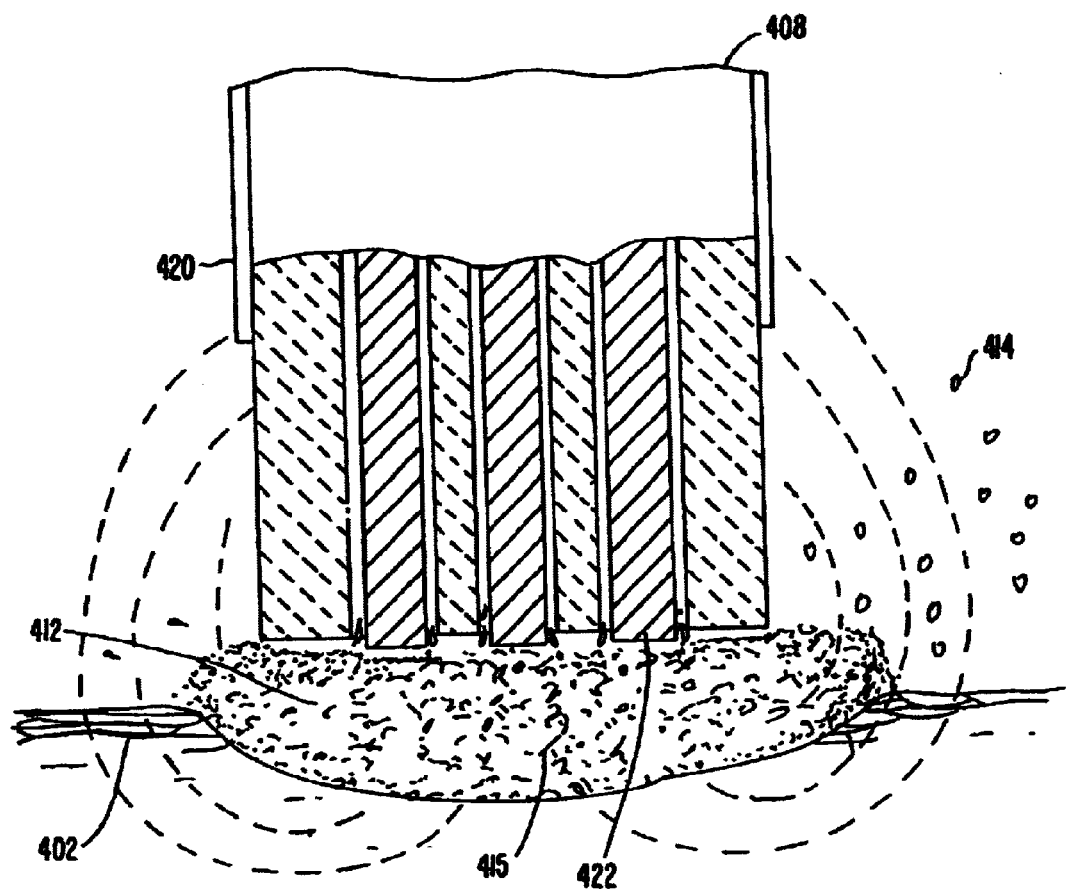
FIGS. 24A and 24B illustrate the volumetric removal of occlusive media in more detail.
Figure 24B:
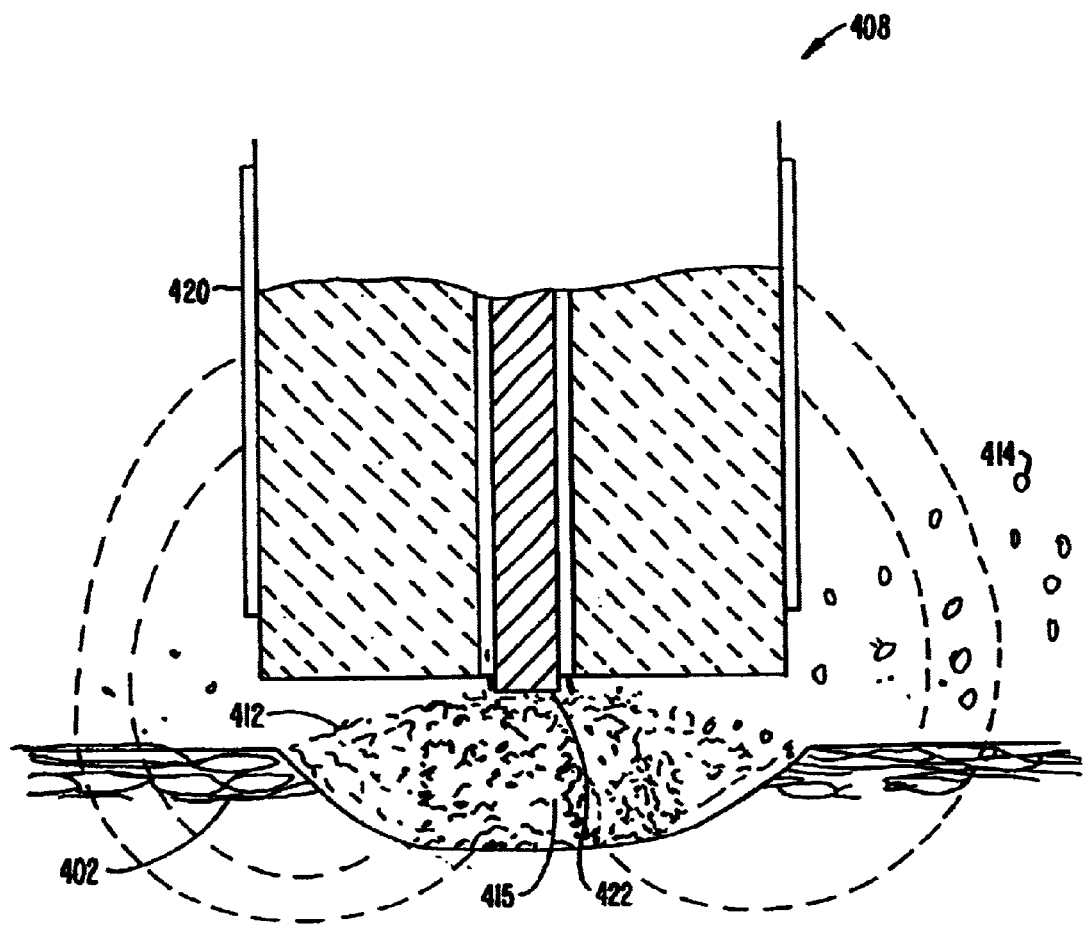

FIGS. 24A and 24B illustrate the volumetric removal of occlusive media in more detail. As shown, the high frequency voltage is sufficient to convert the electrically conductive fluid (not shown) between the occlusion 402 and active electrode(s) 422 into an ionized vapor layer 412 or plasma. As a result of the applied voltage difference between active electrode(s) 422 and the occlusive media 402 (i.e., the voltage gradient across the plasma layer 412), charged particles 415 in the plasma (e.g., electrons) cause the molecular dissociation of components of occlusive media. This molecular dissociation is accompanied by the volumetric removal (i.e., ablative sublimation) of occlusive materials and the production of low molecular weight ablation by-products 414, e.g., gases such as oxygen, nitrogen, carbon dioxide, hydrogen and methane. This process can be precisely controlled to minimize damage and necrosis to the surrounding vessel wall 404. During the process, the gases 414 may be aspirated through catheter 408. In addition, excess electrically conductive fluid, and other fluids (e.g., blood) may be aspirated from the target site to facilitate the surgeon's view.

Figure 25:
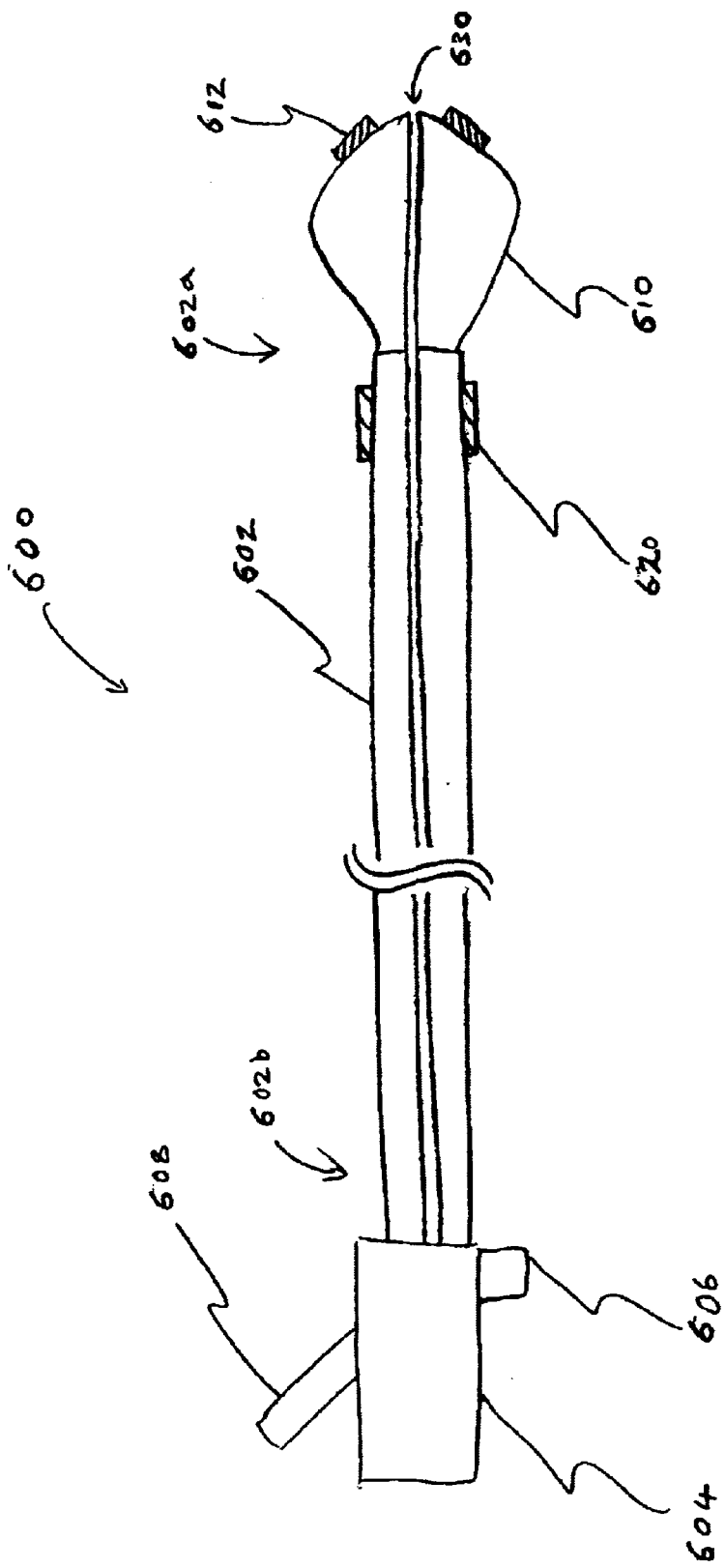
FIG. 25 is a longitudinal sectional view of an electrosurgical catheter, according to another embodiment of the invention.
Figure 30:
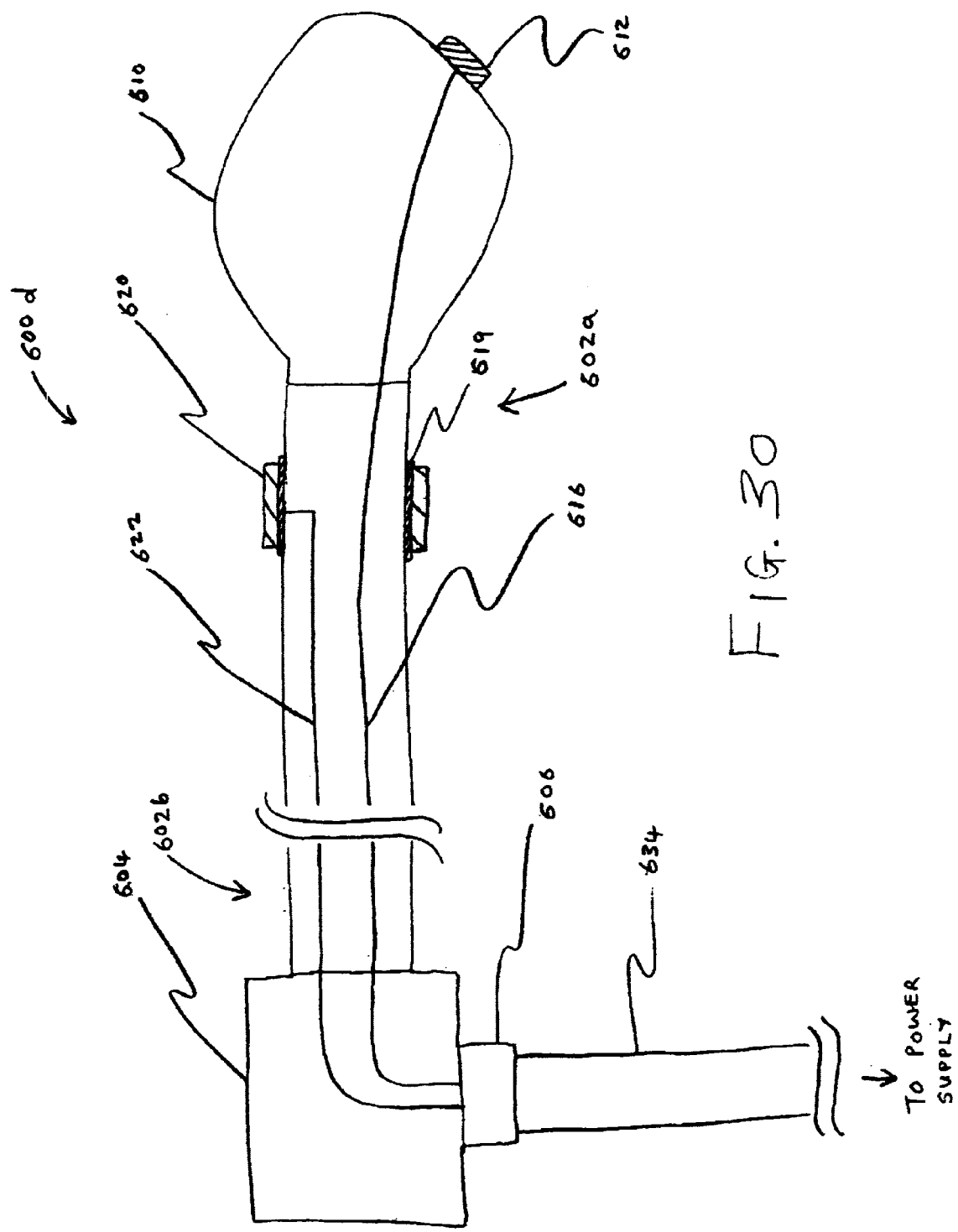
FIG. 30 illustrates a catheter having electrode leads coupled to a cable connector.

FIG. 25 shows another embodiment of an electrosurgical catheter 600 in longitudinal section. Catheter 600 generally includes a shaft 602 and a handle 604. Shaft 602 may be flexible or rigid, and includes a shaft distal end portion 602$a$ and a shaft proximal end portion 602$b$. Shaft 602 may be constructed from a pliable material, for example, various plastics. According to one embodiment, shaft 602 may be constructed from a thermoplastic, polyether—based polyamide, such as a polyether block amide (PEBAX). An exemplary material from which shaft 602 may be constructed comprises PEBAX 63D (Modified Polymer Components, Inc., Sunnyvale, Calif.). Catheter 600 further includes a spacer or electrode support 610 having at least one active electrode 612 arranged thereon. Typically, catheter 600 includes a plurality of active electrodes 612. At least one return electrode 620 is disposed on shaft distal end 602 at a location proximal to support 610. Return electrode 620 may be disposed up to about 15 mm proximal to the exposed portion of active electrodes 612. Flexible embodiments of catheter 600 typically include a guidewire lumen 630 for guiding catheter 600 on a guidewire 640 (FIG. 26B). Guidewire lumen 630 may be constructed from a pliable material, for example, various plastics. An exemplary material from which guidewire lumen 630 is constructed comprises polyethylene. Rigid embodiments of catheter 600 may or may not include a guidewire lumen 630. Handle 604 may include a cable connector 606 and a fluid delivery connector 608. Cable connector 606 is in communication with active electrodes 612 and return electrode 620 via electrode leads (FIG. 30).

Figure 27:
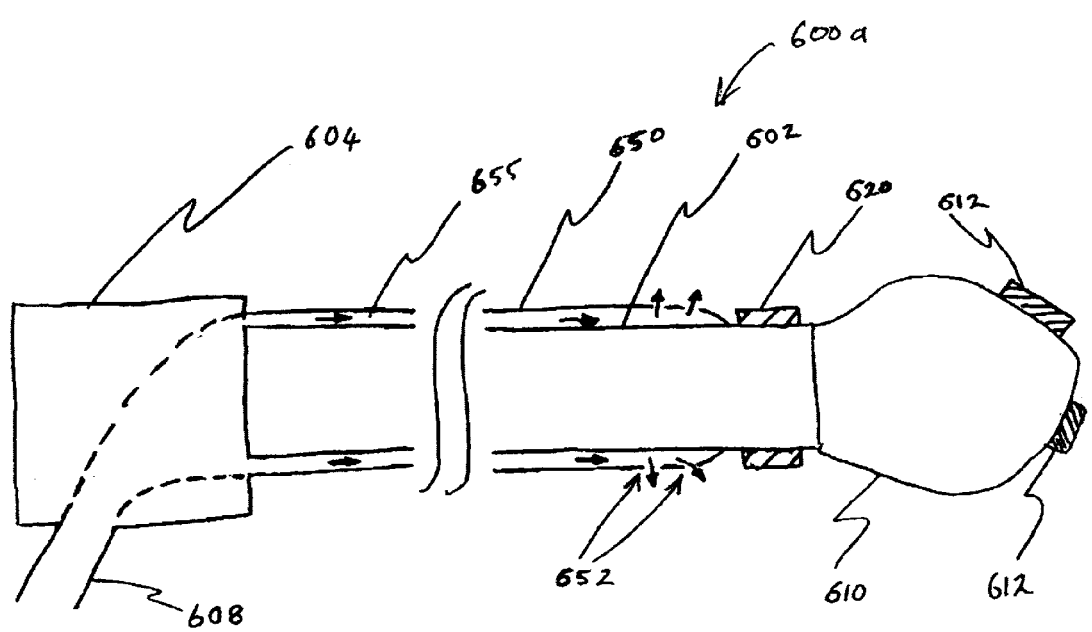
FIG. 27 shows a catheter including a fixed, external fluid delivery unit, according to one embodiment of the invention.
Figure 29:
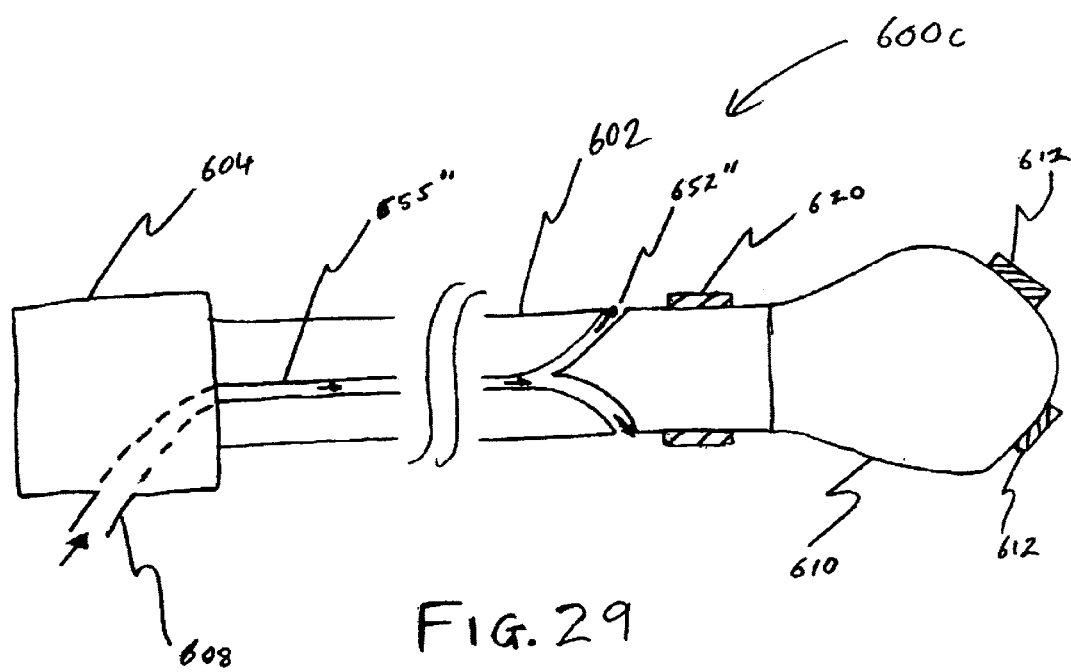
FIG. 29 shows a catheter having an internal fluid delivery unit.

Fluid delivery connector 608 allows the input of an electrically conductive fluid to shaft distal end portion 602$a$ via a fluid delivery lumen 655/655'/655" (FIGS. 27–29).

Catheter 600 may include one or more strain relief units (not shown) located at the point of union of shaft 602 and handle 604. Such strain relief units typically comprise a synthetic polymeric material and serve to prevent distortion of shaft 602 at the joint with handle 604. Catheter 600 may further include a thin external coating (not shown) of a biocompatible material on at least shaft distal end portion 602a of shaft 602. The thin external coating may also be present on at least a portion of electrode support 610. The thin external coating provides lubricity and facilitates guiding or tracking of shaft distal end portion 602a to a target site within a patient's body (e.g., a partly occluded vessel or stent). The thin external coating may comprise a synthetic polymeric material, such as polyvinylpyrrolidone ((PVP), also known as polyvidone).

Figure 26A:
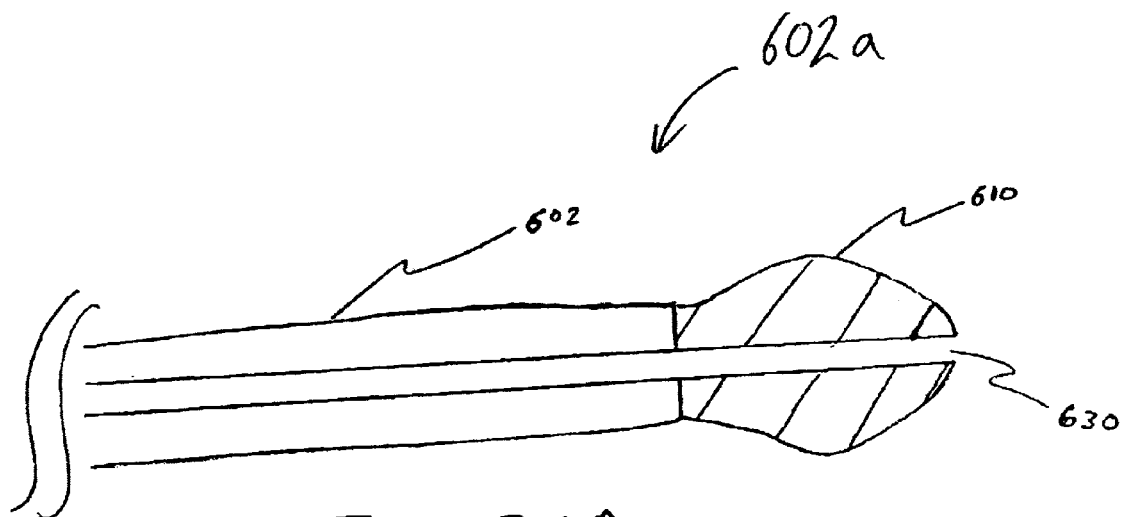
FIGS. 26A and 26B are longitudinal sections of the distal end portion of a catheter showing a guidewire lumen with and without a guidewire, respectively.
Figure 26B:
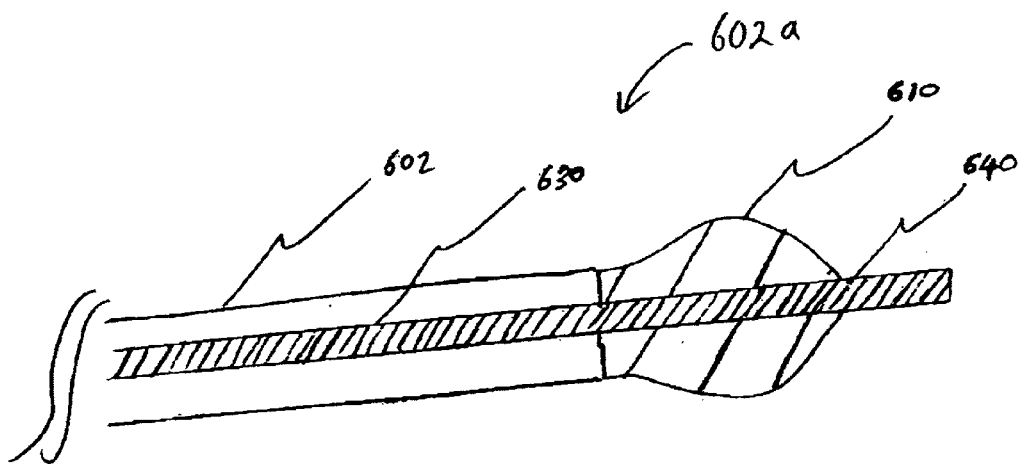

FIG. 26A is longitudinal sectional view of shaft distal end portion 602a of catheter 600 showing guidewire lumen 630 as a void. Typically, guidewire lumen 630 is centrally located along the longitudinal axis of shaft 602. FIG. 26B shows shaft distal end portion 602a with a guidewire 640 positioned within guidewire lumen 630. Guidewire lumen 630 allows shaft distal end portion 602a to be guided along guidewire 640 to a target site within a patient's body.

Referring now to FIG. 27 there is provided an electrosurgical catheter 600a having a fixed, external fluid delivery unit, according to one embodiment of the invention. An external sheath 650 extends along shaft 602 from shaft proximal end 602b to shaft distal end 602a, and defines an annular fluid delivery lumen 655 between shaft 602 and external sheath 650. External sheath 650 may be constructed from a pliable material, for example, various plastics, such as PEBAX, polyethylene, polyurethane or nylon. An exemplary material from which external sheath 650 is constructed comprises PEBAX 63D. In the embodiment of FIG. 27, external sheath 650 is fixed to shaft 602 at shaft distal end 602a at a position proximal to return electrode 620. Electrically conductive fluid (represented as solid arrows) entering catheter 600 at fluid delivery connector 608 flows distally along fluid delivery lumen 655 to shaft distal end 602a where it exits at fluid delivery ports 652. Fluid may be delivered from a source of electrically conductive fluid (e.g., source 100, FIG. 1) by gravity or via a pumping mechanism. Delivery of electrically conductive fluid from fluid delivery ports 652 creates a current flow path between active electrodes 612 and return electrode 620. Guidewire lumen 630 is omitted from FIG. 27 for the sake of clarity.

Referring now to FIGS. 28A, 28B there is provided an electrosurgical catheter 600b having a moveable, external fluid delivery unit, according to another embodiment of the invention. As seen in FIGS. 28A, 28B, a moveable external sheath 650' is in communication at its proximal end with a second handle 605 having fluid delivery connector 608. Second handle 605 and moveable external sheath 650' are slidably engaged on shaft 602. Moveable external sheath 650' defines an annular fluid delivery lumen 655' between shaft 602 and external sheath 650'. The distal terminus of moveable external sheath 650' defines an annular fluid delivery port 652' at shaft distal end portion 602a proximal to return electrode 620. The distance between fluid delivery port 652' and return electrode 620 may be varied over a distance ranging from at least L1 (FIG. 28A) to L2 (FIG. 28B) by moving second handle 605 and external sheath 650' longitudinally with respect to shaft 602.

FIG. 29 shows a catheter 600c having an internal fluid delivery unit, according to another embodiment of the invention. In this embodiment fluid delivery connector 608 is in communication with an internal fluid delivery lumen 655''. Electrically conductive fluid (represented by solid arrows) is delivered to the exterior of shaft 602 via at least one fluid delivery port 652'' at shaft distal end portion 602a at a location proximal to return electrode 620. Guidewire lumen 630 is omitted from FIG. 29 for the sake of clarity.

Referring now to FIG. 30 there is provided an electrosurgical catheter 600d having an integral catheter cable 634 attached to handle 604 via cable connector 606. Catheter cable 634 is adapted for coupling active electrodes 612 and return electrode 620 to a power supply (e.g., FIGS. 1, 13–22E, 31B). Cable connector 606 is coupled to active electrodes 612 via active electrode lead 616. A single active electrode 612 and a single active electrode lead 616 are shown in FIG. 30 for the sake of clarity. In practice, each of a plurality of active electrodes 612 is coupled to a corresponding active electrode lead 616. Cable connector 606 is also coupled to return electrode 620 via return electrode lead 622. In the embodiment of FIG. 30, return electrode 620 is disposed on an insulating electrode liner 619 which may be constructed from a layer of an insulating material such as a polyimide. Liner 619 serves to electrically insulate return electrode 620 from other catheter components.

Figure 31A:
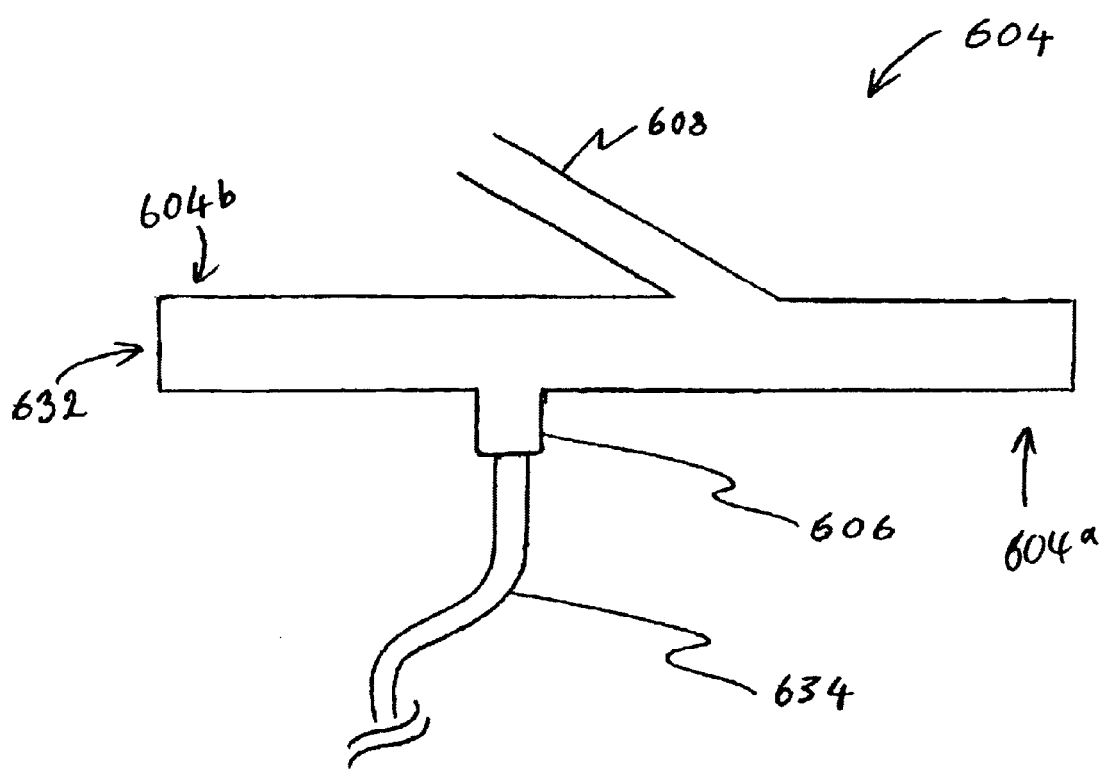
FIG. 31A schematically represents a catheter handle having an integral catheter cable, according to one embodiment of the invention.

FIG. 31A shows a side view of a catheter handle 604 including integral catheter cable 634 attached to handle 604 via cable connector 606, according to one embodiment of the invention. Handle 604 further includes fluid delivery connector 608 and auxiliary connector 632 at handle proximal end 604b. Handle 604 is attached to shaft proximal end 602b (not shown in FIG. 31A at handle distal end 604a. Auxiliary connector 632 may accommodate guidewire 640, one or more conduits for transporting balloon inflation fluid, e.g., conduit 107 (FIG. 1), or a multi-lumen fitment 114 (FIG. 1).

Figure 31B:
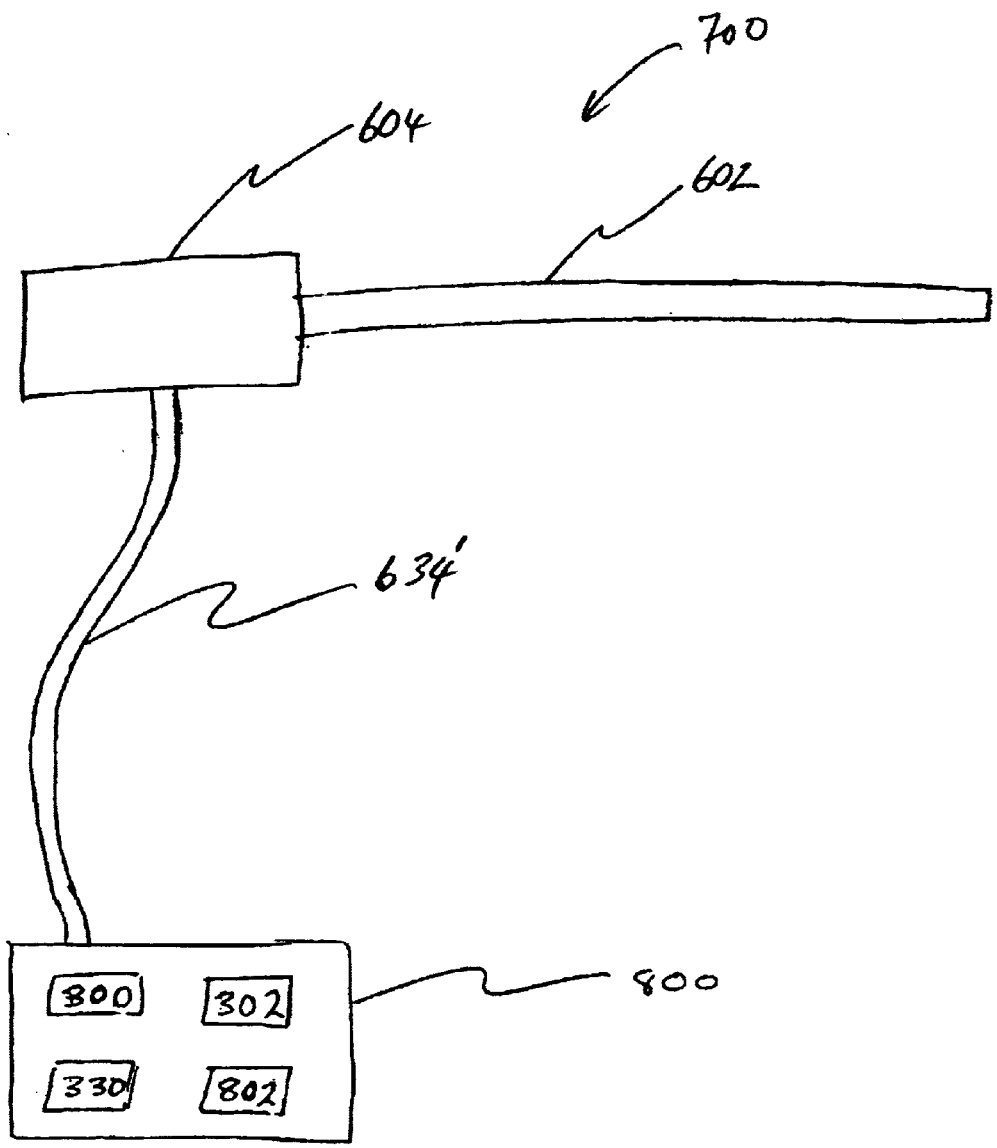
FIG. 31B schematically represents an electrosurgical system including a catheter coupled to a power supply via a catheter cable.

FIG. 31B schematically represents an electrosurgical system 700, including catheter 600 coupled to a power supply 800 via a catheter cable 634'. Catheter cable 634' may be integral with handle 604 of catheter 600 (e.g., FIG. 31A), or catheter cable 634' may be a separate, detachable component of system 700. Power supply 800 preferably includes one or more power regulatory components for limiting or preventing delivery of power from power supply 800 under certain circumstances. Power supply 800 may have structures, elements, features, and characteristics of the power supply described hereinabove, for example, as described with reference to FIGS. 13–22E. Typically, power supply 800 includes one or more of the following power regulatory components: a power limiting device 300, a spark limiting device 330, a current sensor 302, and a fluid interlock unit 802. Each of these power regulatory elements has been described hereinabove. An exemplary power supply 800 is the ArthroCare System 6000 Controller (ArthroCare Corporation, Sunnyvale, Calif.).

Figure 32:
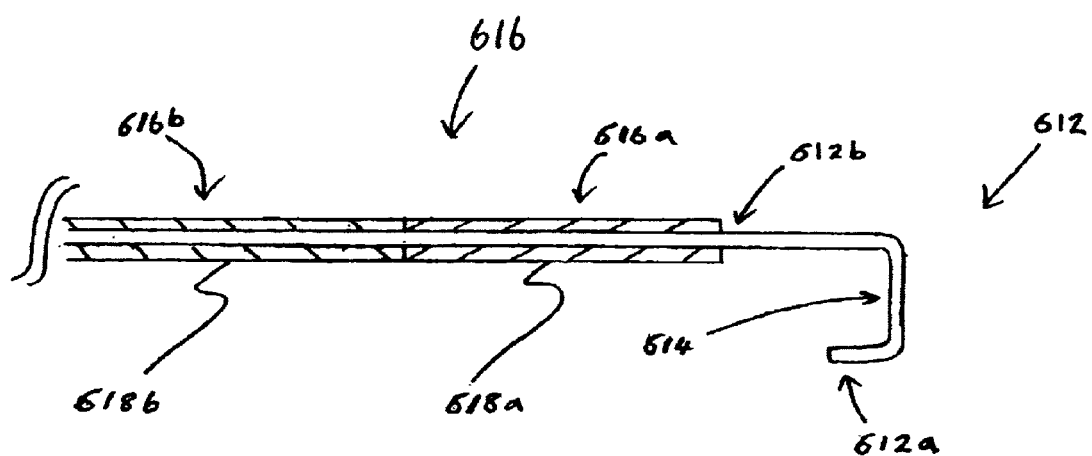
FIG. 32 shows an active loop electrode in communication with an electrically insulated electrode lead.

FIG. 32 shows an active electrode 612 in communication with an electrically insulated active electrode lead 616. Active electrode lead 616 includes a lead distal portion 616a and a lead proximal portion 616b. Lead distal portion 616a has a layer of distal insulation 618a thereon, and lead proximal portion 616b has a layer of proximal insulation 618b thereon. Active electrode 612 includes a free end 612a, a loop portion 614, and a connected end 612b in communication with lead distal portion 616a. In one embodiment, active electrode 612 and active electrode lead 616 each comprise a wire having a diameter in the range of from about 0.004" to about 0.009". In one embodiment, active electrode 612 and lead distal portion 616a each comprise a metal such as platinum, platinum-iridium, platinum-tantalum, platinum-molybdenum, platinum-silver, platinum-tungsten, molybdenum, titanium, tungsten, or tantalum. Active electrode 612 and lead distal portion 616a may each consist essentially of platinum. Further, active electrode 612 and lead distal portion 616a may each consist essentially of an alloy of platinum and iridium, wherein the alloy comprises from about 75% to about 99.95% platinum and from about 0.05% to about 25% iridium. Typically, active electrode 612 and lead distal portion 616a comprises from about 85% to about 95% platinum, and from about 5% to about 15% iridium. In one embodiment, active electrode 612 and lead distal portion 616a are both formed from a single length of insulated platinum/iridium (Pt/Ir) wire, from which the insulation layer has been removed over a portion of its length to form active electrode 612. In one embodiment, lead proximal portion 616b comprises molybdenum. Proximal insulation 618b of lead proximal portion 616b may comprise a fluoropolymer resin, such as a modified ethylenetetrafluoroethylene (ETFE). An exemplary fluoropolymer resin is Tefzel®=ETFE (DuPont). Distal insulation 618a on lead distal portion 616a may comprise a polyimide, or a fluoropolymer resin, such as Tefzel®. Typically, lead proximal portion 616b is substantially longer than lead distal portion 616a, the former generally occupying from about 70% to about 98% of the total length of active electrode lead 616.

The active electrode may comprise a wire having a diameter in the range of from about 0.002" to about 0.020", and in some embodiments, from about 0.002" to about 0.008". The wire can comprise an alloy of platinum and iridium. Additionally, the proximal active electrode lead portion can comprise at least 50% molybdenum.

FIGS. 33A–B, 34A–B, 35A–B, and 36A–B each show an end view and a side view of active electrodes 612 arranged on an electrode support 610, according to four different embodiments of the invention. Electrode support 610 may be somewhat rotund or bulbous in shape, and includes a support distal portion 610a, a belly portion 610b representing a point of maximum width or girth of support 610, and a support proximal portion 610c. In one embodiment, electrode support 610 tapers from narrow to broad in a direction proximal to support distal portion 610a towards belly portion 610b, and tapers from broad to narrow in a direction proximal to belly portion 610b towards support proximal portion 610c. According to certain embodiments, the terminals of active electrodes 612, including loop portion 614, are restricted to locations on support 610 distal to belly portion 610b. By restricting active electrodes 612 to locations distal to the widest portion of support 610, the likelihood of inadvertent contact of active electrodes 612 with a prosthesis or the walls of a body passage is minimized. Electrode support 610, as well as shaft 602, may be provided in a broad range of diameters suitable for clearing occlusions from body passages having a wide variety of sizes.

Figure 33A:
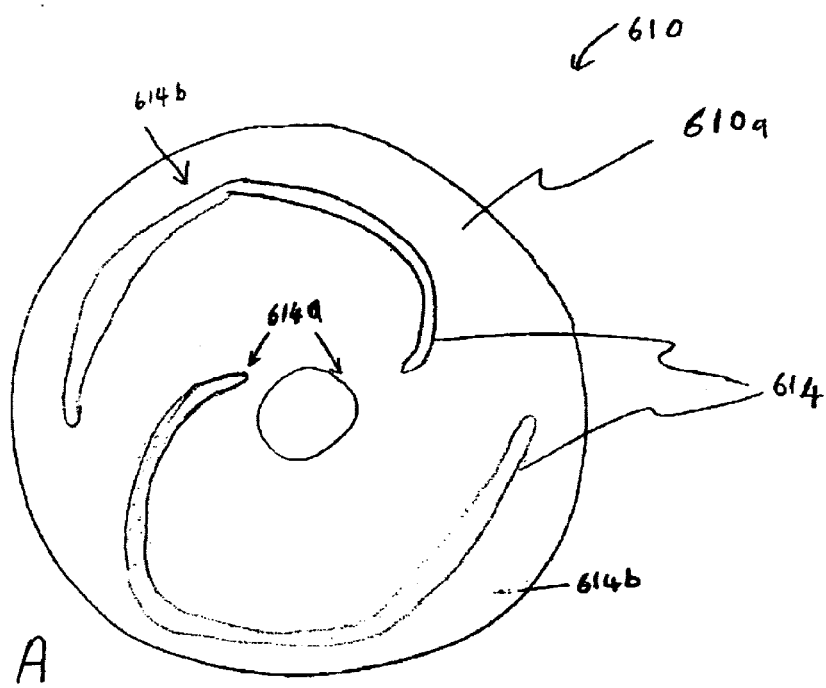
FIGS. 33A–B, 34A–B, 35A–B, and 36A–B each show an end view and a side view of active electrodes arranged on an electrode support, according to four different embodiments of the invention.
Figure 33B:
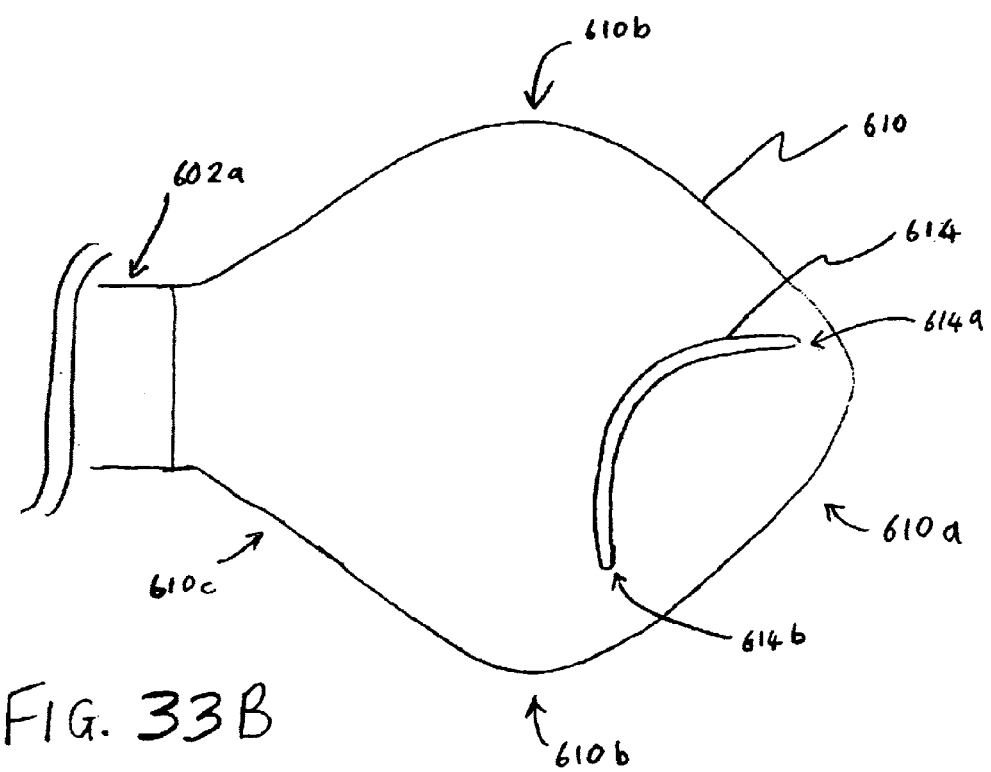
Figure 34A:
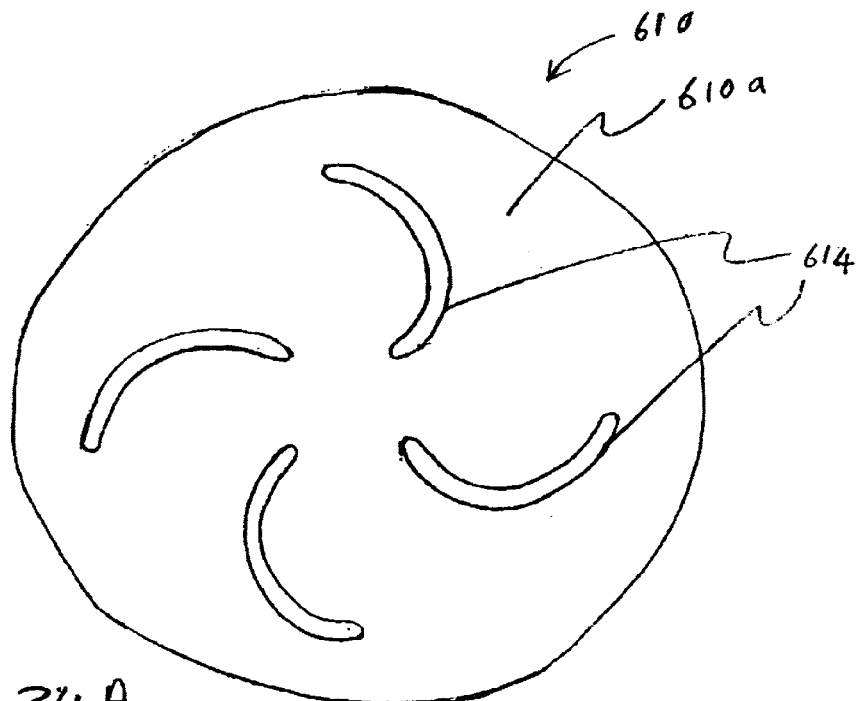
Figure 34B:
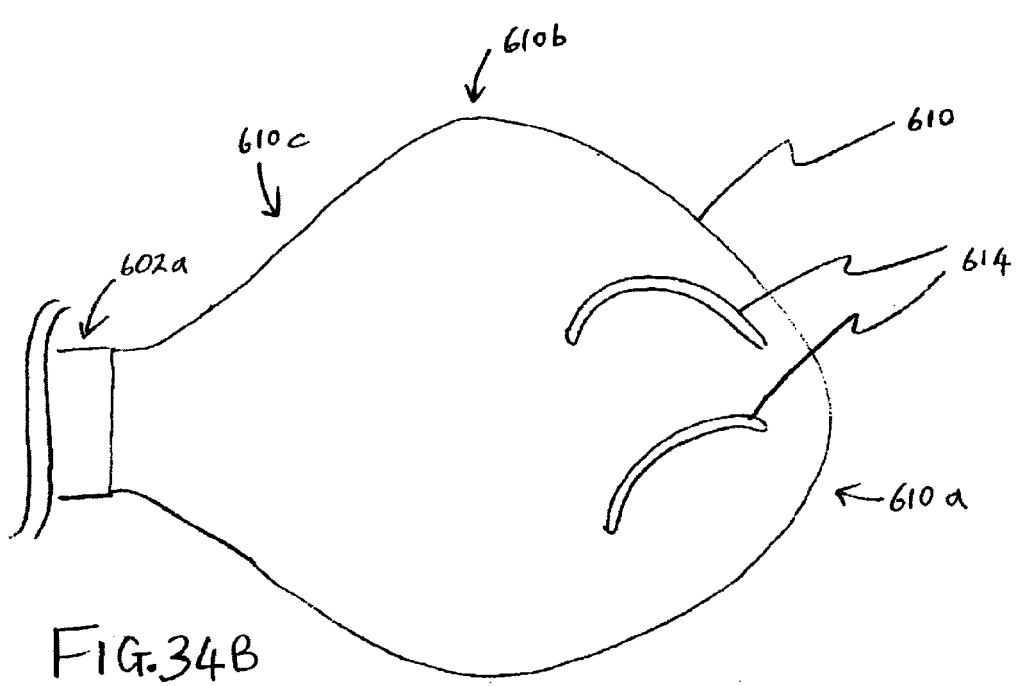
Figure 35A:
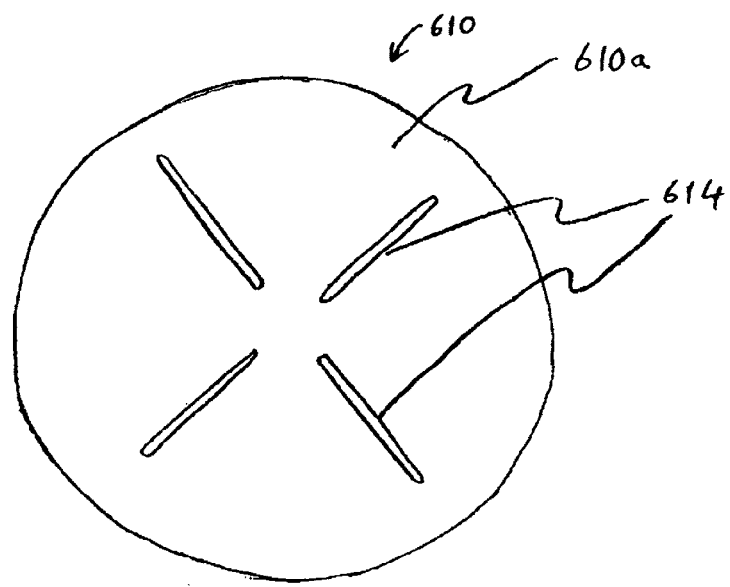
Figure 35B:
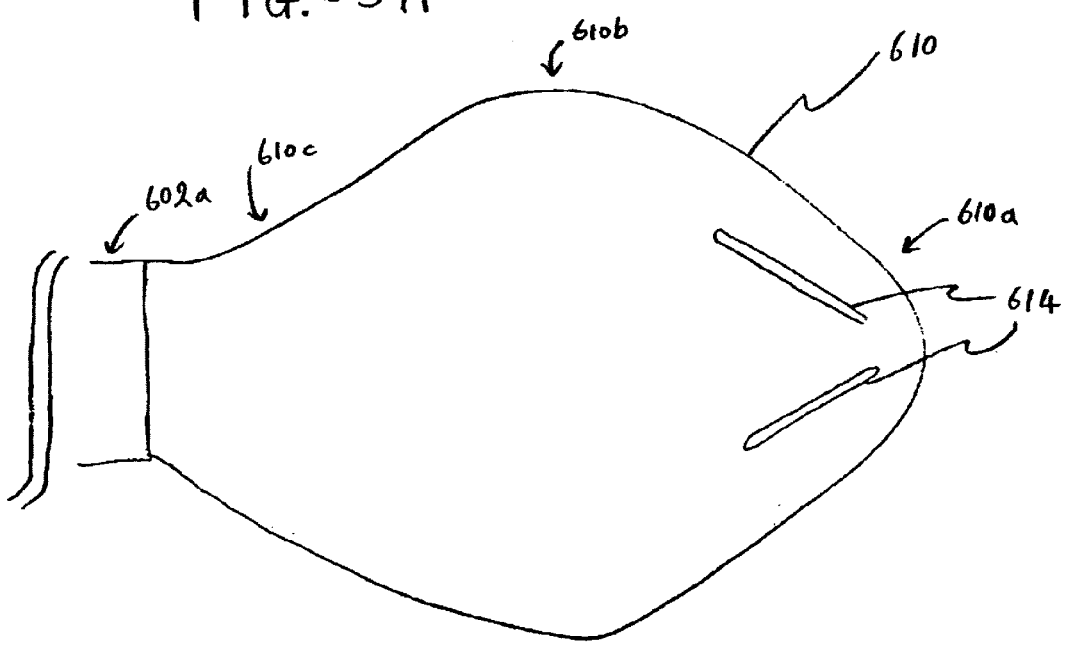
Figure 36A:
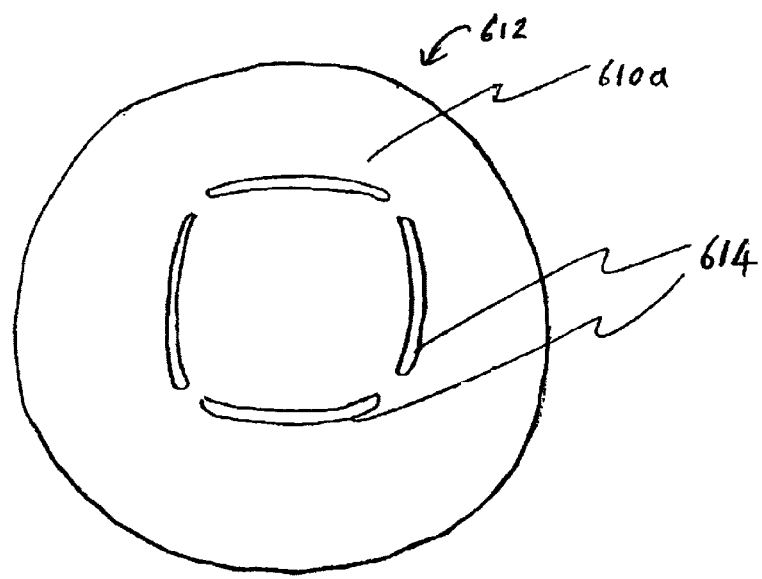
Figure 36B:
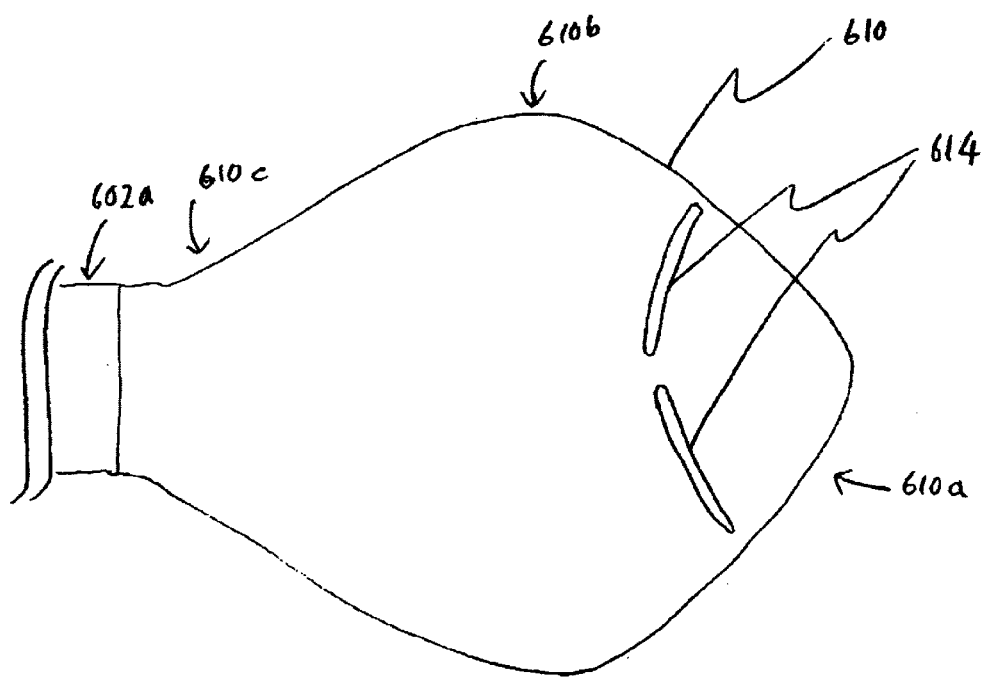

FIGS. 33A and 33B show electrode support 610 having two active electrodes 612 arranged thereon, wherein the active electrode terminals include loop portion 614 in the form of a curved wire radiating proximally from a position 614a somewhat proximal to the apex of support 610. Loop portions 614 terminate at a location 614b distal to belly portion 610b. FIGS. 34A and 34B show an electrode support 610 having an arrangement of active electrodes 612 similar to that of FIGS. 33A and 33B, but having four active electrodes 612 each having loop portion 614. As for FIGS. 33A and 33B, loop portions 614 terminate at a location distal to belly portion 610b. FIGS. 35A and 35B show electrode support 610 having four active electrodes 612 arranged thereon, wherein loop portion 614 of each active electrode 612 is in the form of a substantially straight wire radiating proximally on support distal end 610a from a position somewhat proximal to the apex of support 610. FIGS. 36A and 36B show electrode support 610 having four active electrodes 612 arranged thereon, wherein loop portion 614 of each active electrode 612 is in the form of a slightly curved wire, and the four active electrodes 612 are arranged substantially equidistant from the apex of support 610 to form a quasi ring-shaped active electrode array.

Figure 37B:
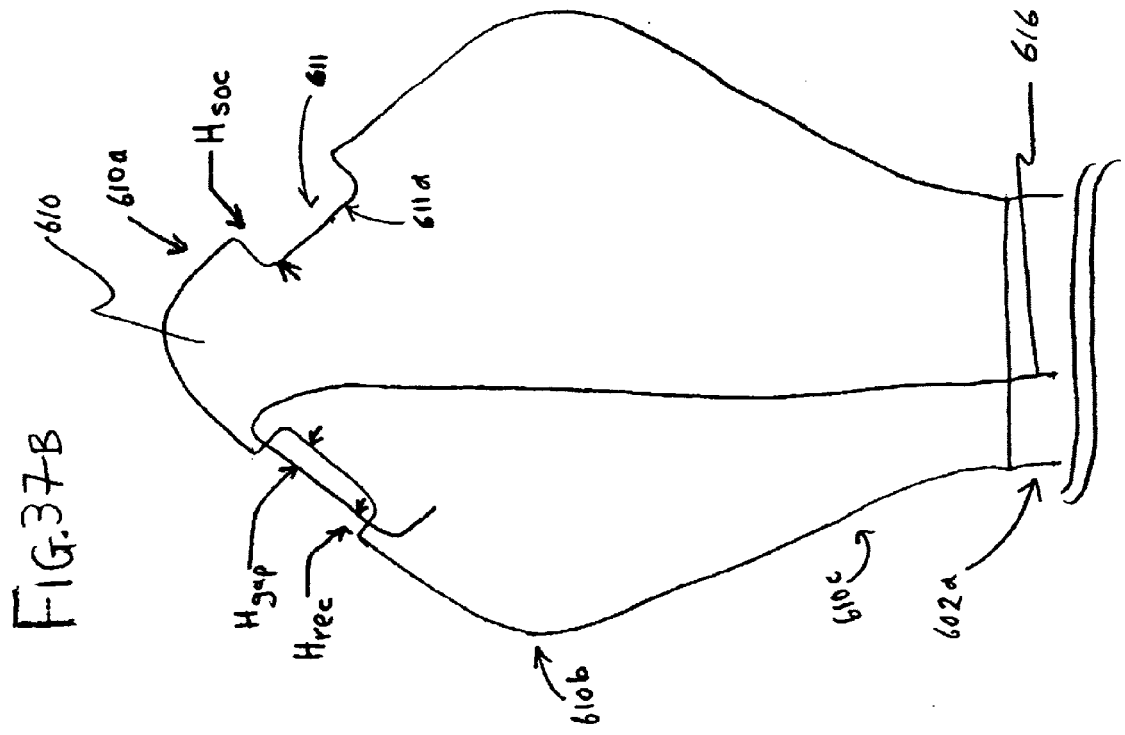
FIG. 37B shows an active electrode recessed within an electrode support having an electrode socket.
Figure 37A:
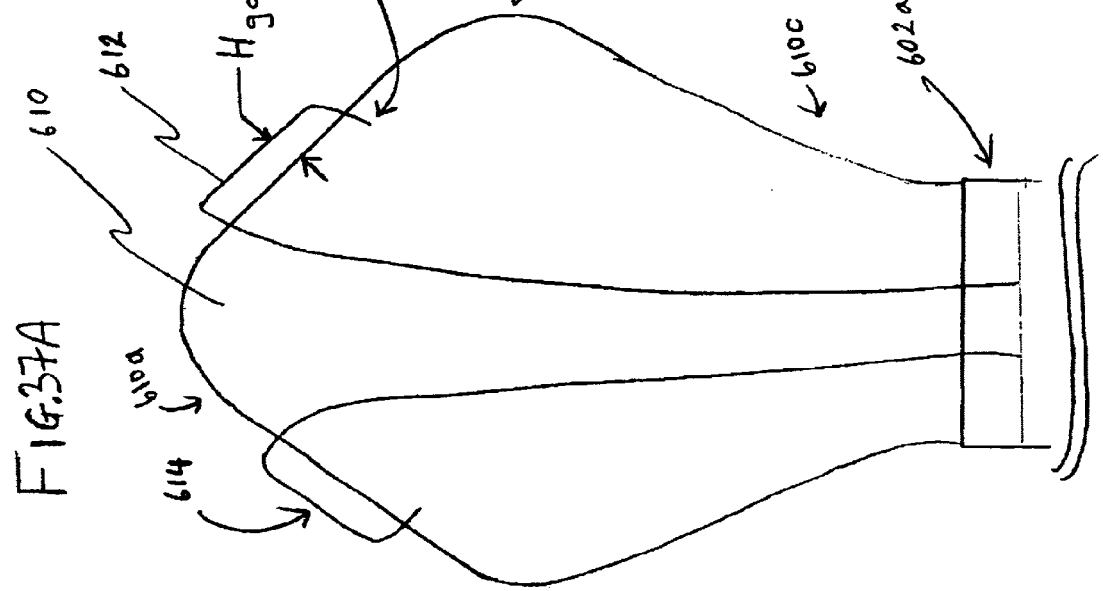
FIG. 37A shows an electrode gap between an active electrode and an electrode support.

FIG. 37A shows electrode support 610 having a pair of active electrodes 612 arranged therein. Support distal end 610a may have a substantially conical external surface. Loop portion 614 may be arranged substantially parallel to the external surface of support distal end 610a. In the embodiment of FIG. 37A, active electrodes 612 each have a loop portion 614 which defines an electrode gap, $H_{gap}$, between the external surface of electrode support 610 and loop portion 614 of the active electrode terminal. The value of $H_{gap}$ typically ranges from about zero up to about 0.200" (0.00 mm to about 5 mm), more typically from about 0.00 mm to about 0.25 mm, and preferably in the range of from about 0.002" to about 0.010". In embodiments wherein loop portion 614 is not recessed within electrode support 610, these values for $H_{gap}$ generally represent the distance to which active electrodes 612 extend beyond the external surface of electrode support 610.

FIG. 37B shows an active electrode terminal recessed within electrode support 610, the latter having a plurality of active electrode sockets 611 located within support distal end 610a. Recessed active electrodes 612 provide an additional level of safety during use of catheter 600, a feature which is particularly valuable when targeting a highly sensitive structure or body passage, e.g., the carotid artery. In the embodiment of FIG. 37B, each active electrode socket 611 accommodates loop portion 614 of active electrode 612. Active electrode socket 611 typically has a depth or height, $H_{soc}$ in the range of from about 0.004" to about 0.010". The depth or height, $H_{rec}$, to which loop portion 614 is recessed within socket 611 typically ranges from about 0.001" to about 0.010". In the embodiment of FIG. 37B, the value of $H_{gap}$ between loop portion 614 and base 611a of socket 611 is typically in the same range as that stated with reference to FIG. 37A. Only one active electrode is shown in FIG. 37B, for the sake of clarity.

Figure 37C:
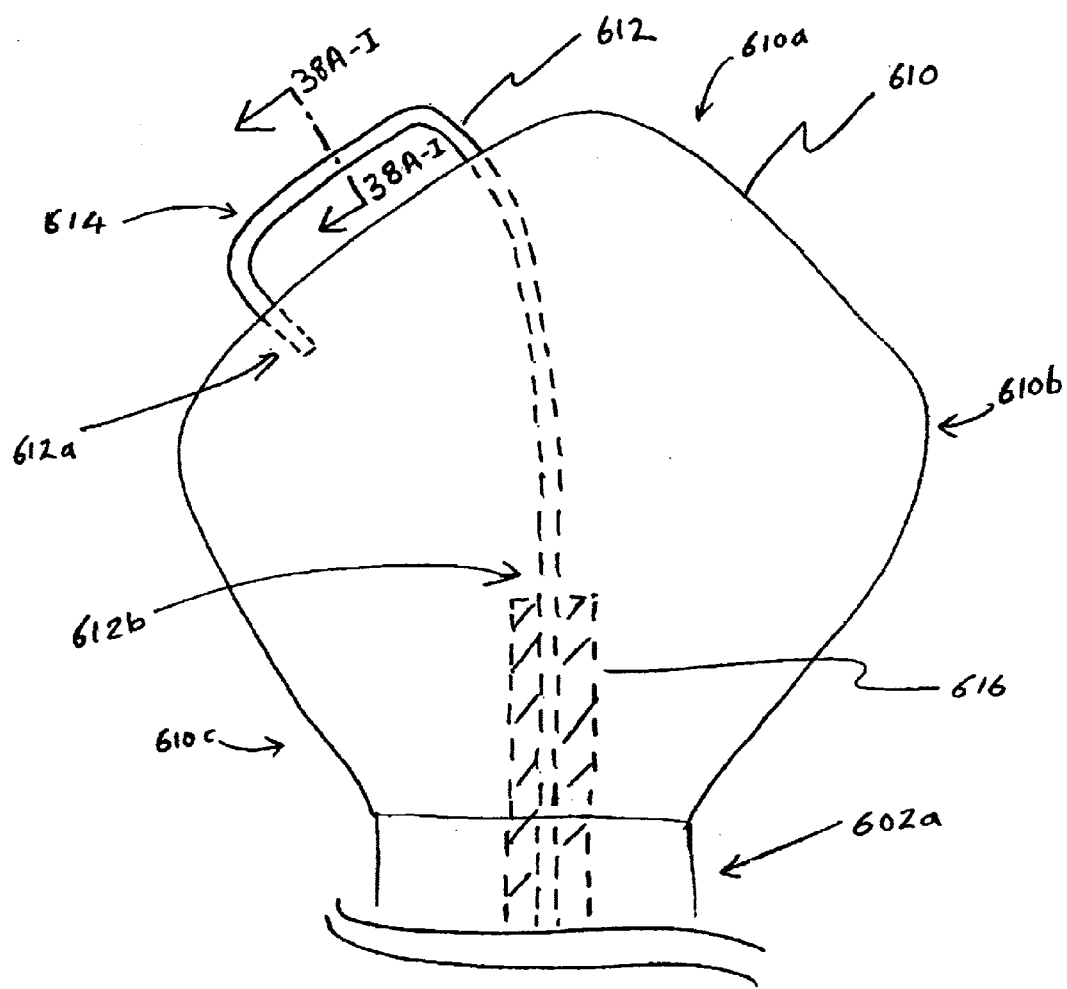
FIG. 37C shows an active loop electrode arranged on a support distal end of an electrode support.

FIG. 37C shows an active loop electrode 612 arranged on support distal end 610a of a bulbous electrode support 610, according to one embodiment of the invention. Electrode support 610 comprises an electrically insulating material such as a silicone rubber, a polyurethane, Teflon, or a ceramic. Preferably, active electrode 612, including free end 612a, is sealed within electrode support 610. In one embodiment, electrode support 610 comprises a silicone rubber. Silicone rubber offers a number of advantages, including the ability to seal the active electrode terminals within the electrode support, electrical insulation, minimum stiction with tissue and blood, as well as good temperature and thermal shock resistance. In addition, silicone rubber causes minimal damage to body tissues. Active electrode 612 is in communication with active electrode lead 616 at active electrode connected end 612b.

Figure 38A:
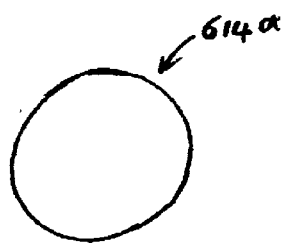
FIGS. 38A–J each show a cross-section of a loop portion of the active loop electrode of FIG. 37C, as seen along the lines 38A–J of FIG. 37C.
Figure 38B:
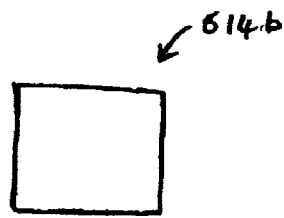
Figure 38C:
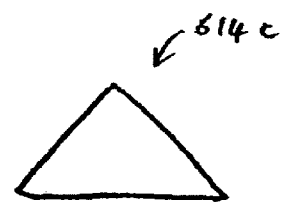
Figure 38D:
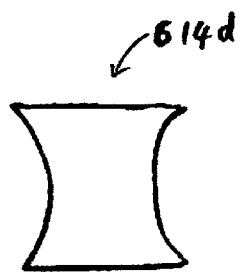
Figure 38E:
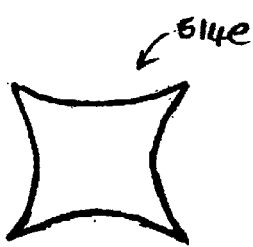
Figure 38F:
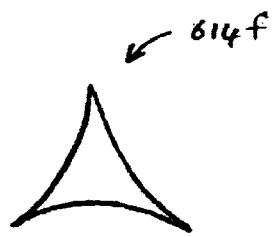
Figure 38G:
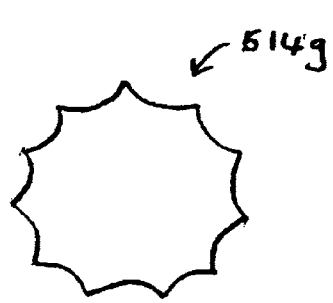
Figure 38H:
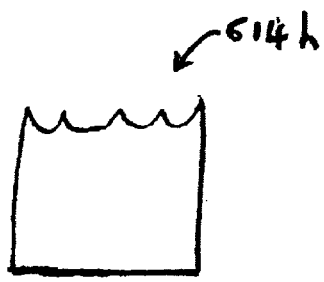
Figure 38I:
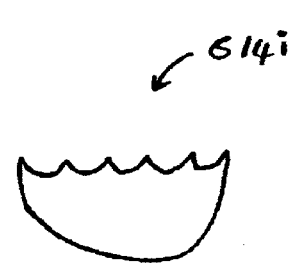
Figure 38J:
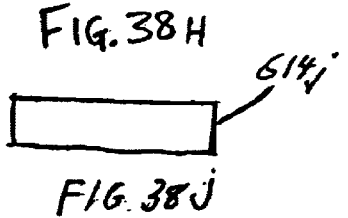

A wide variety of different cross-sectional shapes for loop portion 614 are possible. FIGS. 38A–I each show a cross-section of a loop portion 614a–i of active electrode 612, as seen along the lines 38A–I of FIG. 37C. For example, loop portion 614 may be substantially round or circular, substantially square, or substantially triangular in cross-section, as depicted in FIGS. 38A–C, respectively. Loop portion 614 may have a cross-section having at least one curved side. For example, loop portion 614 of FIG. 38D has two substantially parallel sides and two concave sides. Loop portion 614 of FIG. 38E has four concave sides forming four cusps, while loop portion 614 (FIG. 38F) includes three concave sides forming three cusps. FIGS. 38G–I each depict a cross-section of a loop portion 614 having serrations on at least one side thereof. Loop portion 614g (FIG. 38G) comprises a wire or filament having a substantially circular cross-section, wherein the circumference of the wire is serrated. In another embodiment (not shown) a selected portion of the circumference of a substantially round wire may be serrated. Loop portion 614h (FIG. 38H) comprises a wire having a substantially square cross-section, wherein one side of the wire is serrated. FIG. 38I shows a loop portion 614i comprising a wire of an electrically conductive material, e.g., platinum or Pt/Ir wire, having a substantially semi-circular cross-sectional shape, one portion of which is serrated. FIG. 38J illustrates a rectangular or ribbon wire 614j. In addition, other cross-sectional shapes for loop portion 614 are within the scope of the invention. Preferably, the cross-sectional shape and other features of loop portion 614 promote high current densities in the vicinity of loop portion 614 following application of a high frequency voltage to loop portion 614. High current densities promote generation of a plasma in the presence of an electrically conductive fluid, and the plasma in turn efficiently ablates tissue via the Coblation® procedure or mechanism. Preferably, the cross-sectional shape and other features of loop portion 614 are also adapted for maintenance of the plasma in the presence of an electrically conductive fluid surrounding loop portion 614.

Figure 39A:
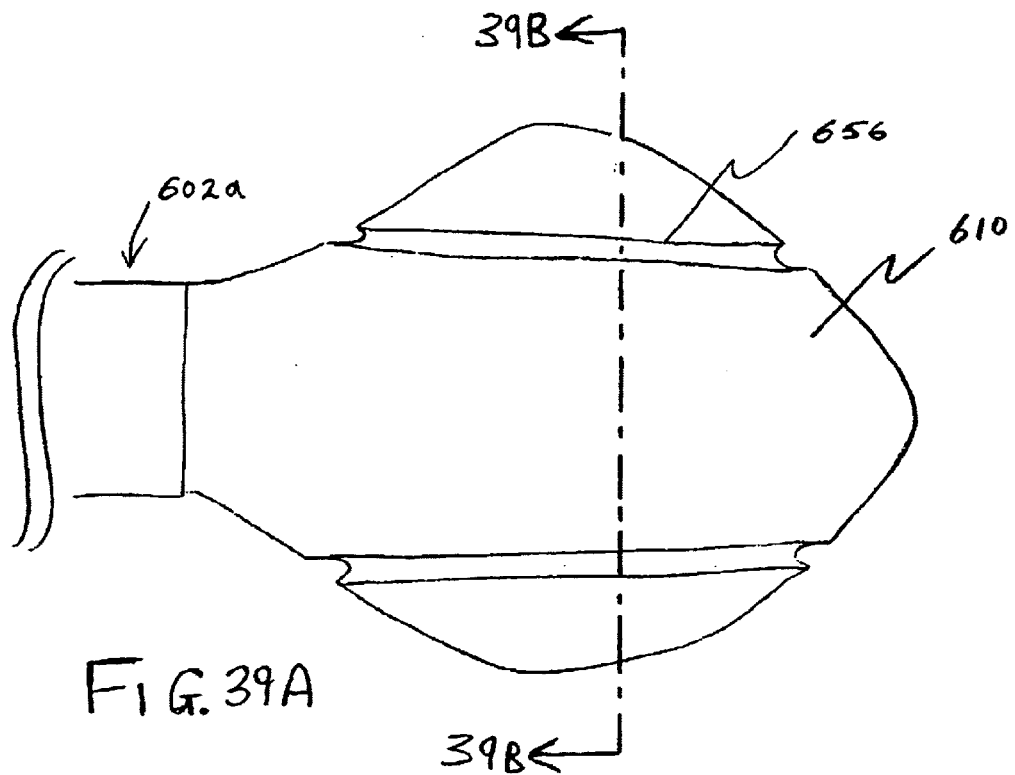
FIGS. 39A and 39B illustrate a side view and an end view, respectively, of an electrode support having a fluid delivery channel therein.
Figure 39B:
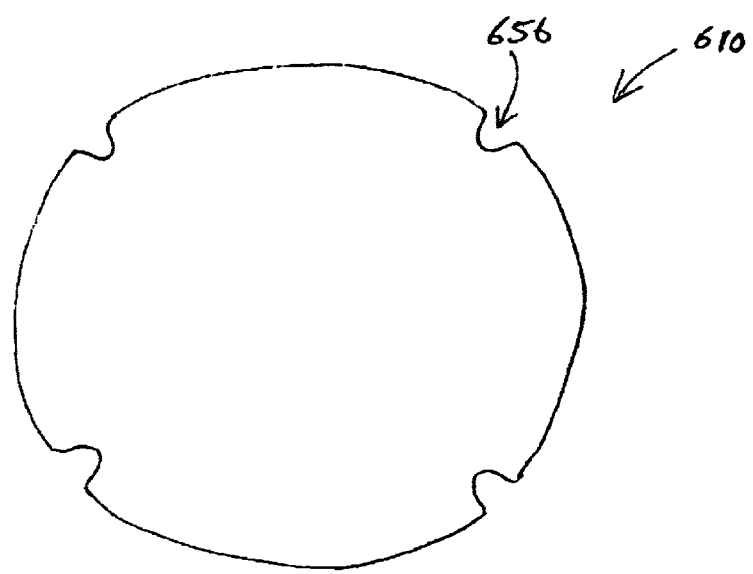

FIG. 39A is a side view of an electrode support 610 having a plurality of fluid delivery channels 656 therein. FIG. 39B is an end view of the electrode support 610 taken along the lines 39B–39B of FIG. 39A showing four fluid delivery channels 656 in the form of grooves in the external surface of support 610. Fluid delivery channels 656 may be straight or curved, and allow for the passage therethrough of an electrically conductive fluid and blood perfusion. Although a total of four channels 656 are depicted in FIG. 39B, other numbers and arrangements for channels 656 are also within the scope of the invention. Active electrodes 612 are omitted from FIGS. 39A, 39B for the sake of clarity.

Figure 40:
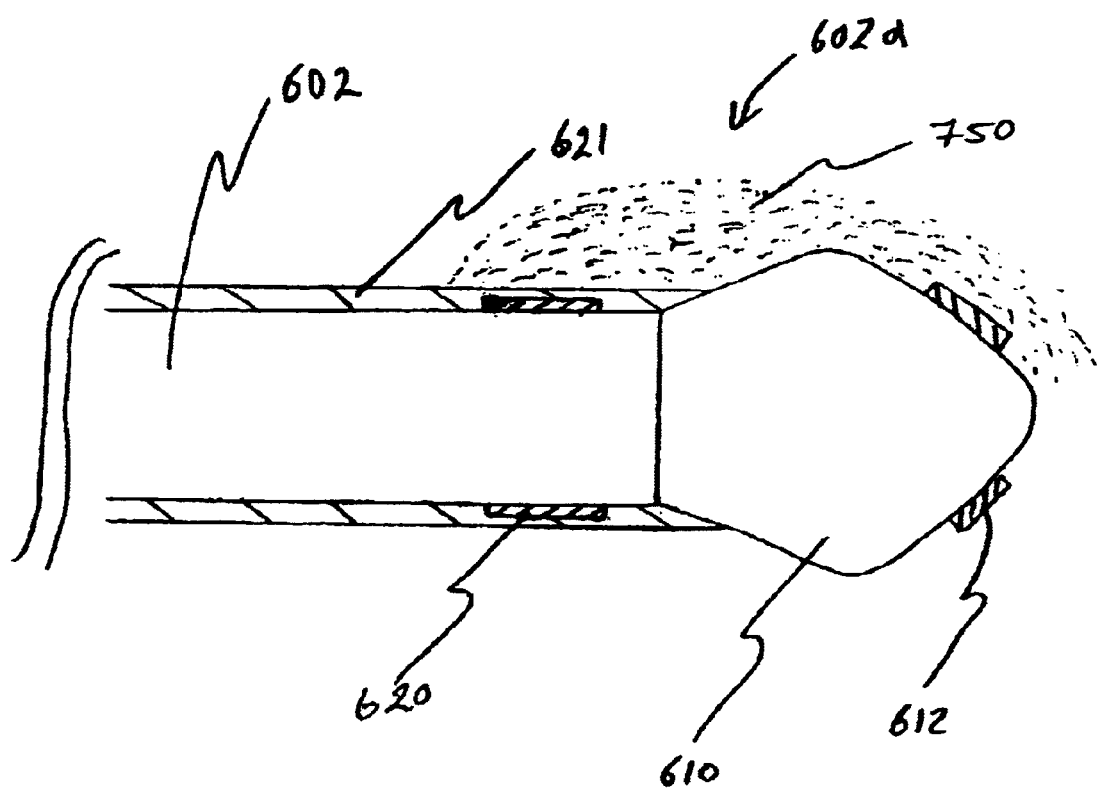
FIG. 40 shows the distal end portion of a catheter having an insulating sleeve covering a return electrode, according to another embodiment of the invention.

FIG. 40 shows shaft distal end portion 602a of a catheter, according to another embodiment of the invention, in which return electrode 620 is covered by an electrically insulating sleeve 621. A quantity of an electrically conductive fluid 750 is delivered to the shaft distal end 602a such that electrically conductive fluid 750 is continuous between active electrodes 612 and sleeve 621 in the region of return electrode 620. The embodiment of FIG. 40 may cause ablation of tissue or occlusive media via a capacitive charge process, in which return electrode 620 functions as the first conducting plate of a capacitor, active electrodes 612 together with electrically conductive fluid 750 function as the second conducting plate, and sleeve 621 functions as the dielectric separating the first and second conducting plates. When a high frequency voltage is applied between the first and second conducting plates, high electric field intensities are generated sufficient to cause molecular dissociation of occlusive media within a body passage, resulting in the formation of low molecular weight ablation by-products, and removal of occlusive media from the target site.

Sleeve 621 may be a coating or layer of a plastic or similar material, such as a polyimide, urethane, a silicone rubber, a fluropolymer, or a polyester. The material of sleeve 621 will depend on the desired characteristics of the capacitor, i.e., dielectric constant, thickness, etc. As shown in FIG. 40, return electrode 620 is disposed on the outer surface of shaft 620 radially inward from sleeve 621. In this manner, return electrode 620 is electrically insulated from active electrodes 612 by sleeve 621, and sleeve 621 also serves to insulate tissue or body structures from return electrode 620. Return electrode 620 preferably comprises a single annular band, e.g., a metal band comprising platinum. The length of return electrode 620 is preferably in the range from 0.5 mm to 10 mm, and more preferably in the range from 1 mm to 5 mm. Return electrode 620 typically has a larger surface area than the total surface area of the plurality of active electrodes, in order to provide a more uniform distribution of charge over the surface of return electrode 620 and to minimize the charge at any one point on the surface of return electrode 620. The smaller surface of active electrodes 612 serves to maximize the charge on the surface of the active electrodes 612. The spacing between the most distal portion of return electrode 620 and active electrodes 612 is preferably in the range from 1.0 mm to 10 mm. The thickness of electrically insulating sleeve 621 in the region of return electrode 620 is typically in the range from 0.01 mm to 0.5 mm, and preferably in the range from 0.02 mm to 0.2 mm.

Figure 41A:
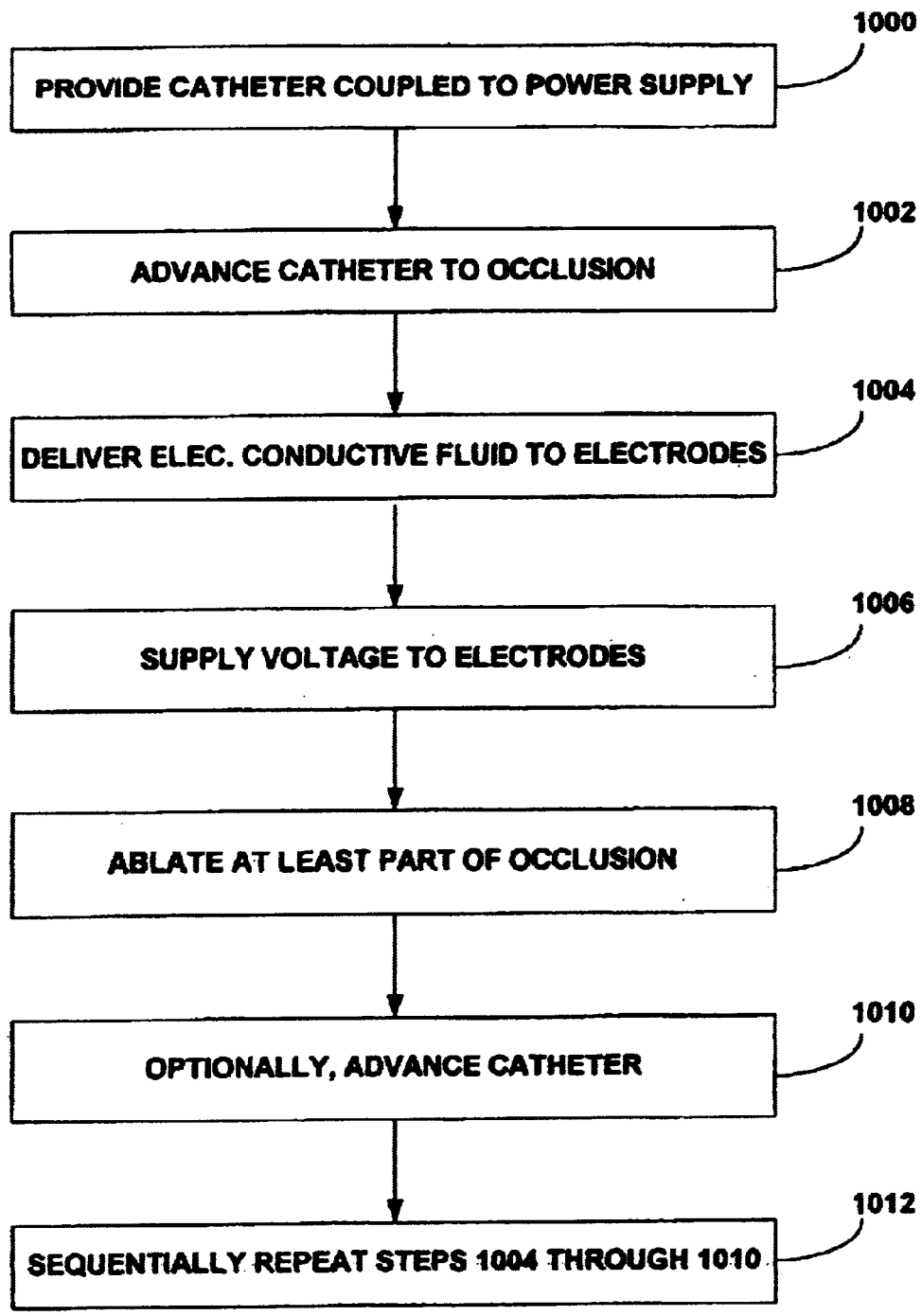
FIG. 41A schematically represents a series of steps involved a method of recanalizing a body passage, according to one embodiment of the invention.

FIG. 41A schematically represents a series of steps involved in a method of recanalizing a body passage, according to one embodiment of the invention. The body passage to be recanalized may be, for example, a partially or totally occluded blood vessel, or a partially occluded stent positioned within a blood vessel. Step 1000 involves providing an electrosurgical catheter coupled to a power supply. The electrosurgical catheter provided in step 1000 may be any one of the various embodiments described hereinabove. The power supply to which the electrosurgical catheter is coupled may be any of the power supplies or controllers described hereinabove, e.g., power supply 800 (FIG. 31B). In one embodiment, each electrode of the catheter is independently coupled to the power supply such that each electrode independently receives power from the power supply, and a first subset of the complement of electrodes can continue to receive power from the power supply when power from the power supply is shut off to a second subset of the complement of electrodes. Step 1002 involves advancing the catheter, and in particular the shaft distal end, to an occlusion or target site. When the target site is at least somewhat remote from a point of ingress, step 1002 typically involves advancing a guidewire to the vicinity of the target site, and thereafter guiding the shaft along the guidewire. The use of guidewires is well known in the art. According to another embodiment, the target site is at least somewhat local to a point of ingress, the catheter shaft is relatively short and relatively rigid, and may lack a guidewire lumen. In the latter case, the catheter may be advanced directly to a target site, either percutaneously or via an orifice or natural opening. In one embodiment, the catheter may be advanced to a target site by introducing the shaft through an introducer tube or device, e.g., a metal cylinder (not shown). Step 1004 involves delivering an electrically conductive fluid, e.g., isotonic saline, to the vicinity of the target site or to the shaft distal end. As an example, electrically conductive fluid may be delivered by means of the fluid delivery devices described hereinabove (e.g., as described with reference to FIGS. 27–29). The electrically conductive fluid may be delivered by gravity feed or via a pumping mechanism from a suitable fluid source, as is well known in the art. In one embodiment, the rate of fluid flow may be controlled with a valve such that a zone encompassing the active electrode(s) and the return electrode is constantly immersed in the fluid during the procedure. The electrically conductive fluid provides a current flow path between the active and return electrodes; or, in alternative embodiments (e.g., FIG. 40), may participate in a capacitive charge process.

Step 1006 involves supplying a suitable high frequency voltage to the electrodes of the electrosurgical catheter. After the power supply has been turned on, the power level may be adjusted such that a high frequency voltage is applied between the active electrodes and the return electrode. Typically, the RMS (root mean square) voltage applied will is in the range of from about 5 volts to 1000 volts, preferably from about 10 volts to 500 volts RMS, and more preferably from about 100 volts to 300 volts RMS, depending on the size, number, and arrangement of the active electrodes; the operating frequency; and the particular procedure (e.g., the nature of the body passage and the type of occlusion to be ablated). Typically, the peak-to-peak voltage will be in the range of from about 10 volts to 2000 volts, preferably in the range of 20 volts to 1000 volts, and more preferably in the range of about 200 volts to 600 volts. The frequency of the voltage applied between the active electrodes and the return electrode for the removal of an occlusion within a body passage or lumen is typically in the range of from about 400 kHz to about 600 kHz, and preferably from about 450 kHz to about 500 kHz.

Step 1008 involves ablating, via a cool ablation mechanism, at least a part of the occlusive material of the occlusion at the target site. During steps 1006 and 1008, the distal portion of the catheter shaft may be advanced forward as the active electrodes are energized, with or without rotational movement of the shaft distal end. Alternatively, the catheter shaft can be advanced longitudinally through the occlusive material during step 1008 without any reciprocating rotational motion.

According to one aspect of the invention, occlusive material in a body passage may be ablated during a process in which the temperature at the target site is in the range of from about 40° C. to about 45° C., and preferably the temperature is about 42° C. Typically, during the entire recanalizing method of the invention, neither the body passage nor the occlusive material occupying the body passage is exposed to a temperature exceeding about 45° C. In this way, damage to a sensitive body passage, e.g., the walls of a blood vessel, is minimized. The ability to maintain a relatively low temperature in the range of from about 40° C. to about 45° C. during the recanalization procedure is made possible by a number of features of the electrosurgical system of the instant invention, including: the power supply design (e.g., as described with reference to FIGS. 13–22E); the delivery of a suitable amount of electrically conductive fluid to the distal end of the catheter shaft; the shape, size, and arrangement of the active electrodes; and the low resistivity of the electrodes and electrode leads. After step 1008, if additional recanalization of the body passage is called for, the catheter may be advanced in step 1010 such that the shaft distal end and active electrodes are in at least close proximity to a further region of occlusive material. Thereafter, steps 1004 through 1010 may be sequentially repeated in step 1012, an appropriate number of times until the body passage has been suitably recanalized.

Figure 41B:
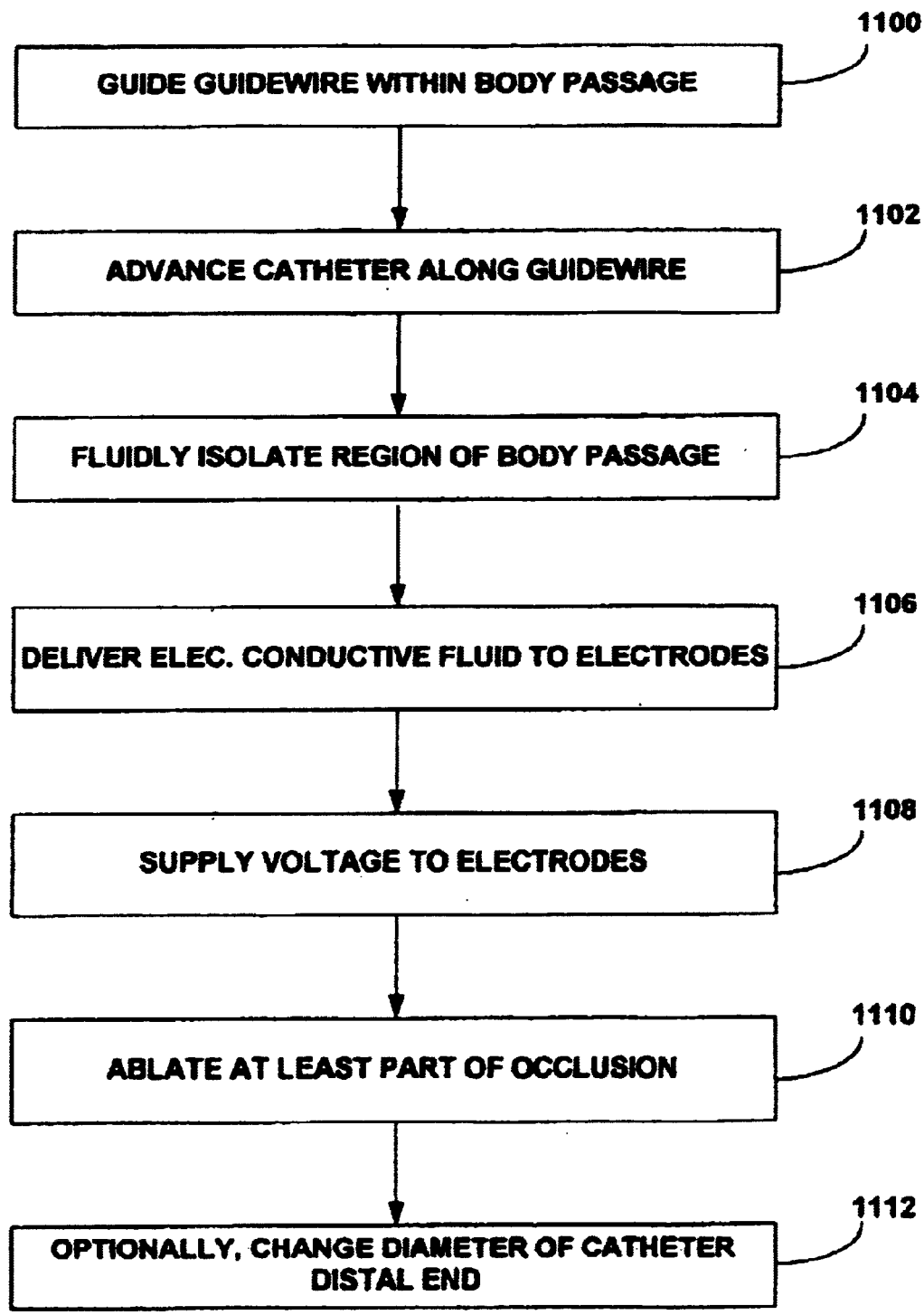
FIG. 41B schematically represents a series of steps involved a method of recanalizing a body passage, according to another embodiment of the invention.

FIG. 41B schematically represents a series of steps involved in a method of recanalizing a body passage, according to another embodiment of the invention. Steps 1100 and 1102 involve guiding a guidewire to a site targeted for treatment within a body passage, and advancing an electrosurgical catheter along the guidewire, essentially as described hereinabove with reference to FIG. 41A. Typically, the target site includes an occlusion within a body passage or within a prosthesis. Step 1104 involves fluidly isolating a region within the body passage to be recanalized. As an example, a blood vessel may be blocked at a first position distal to the occlusion by means of a distal inflatable balloon, and blocked at a second position proximal to the occlusion by means of a proximal inflatable balloon, in order to effectively isolate the target site on a temporary basis. In this manner, blood flow to the target site within the body passage can be prevented, and at the same time the fluidly isolated region can be flooded with isotonic saline during ablation of the occlusion. The inflatable balloons may be integral with the electrosurgical catheter (e.g., FIG. 1), or may be part of a device used in conjunction with the electrosurgical catheter. The use of inflatable balloons, e.g., to distend or occlude blood vessels, is well known in the art. Steps 1106 through 1110 are analogous to steps 1004 through 1008, described hereinabove with reference to FIG. 41A.

In one embodiment, the catheter includes an expansible distal end (e.g., FIGS. 11, 12), and after at least a portion of the occlusion has been ablated according to step 1110, the diameter of the distal end may be changed, step 1112. For example, the shaft distal end having a first diameter may be advanced to an occlusion, and a portion of the occlusion may be ablated to partially recanalize the body passage. Thereafter, the diameter of the distal end may be increased and a further portion of the occlusion may be ablated in order to further recanalize the body passage.

Figure 42:
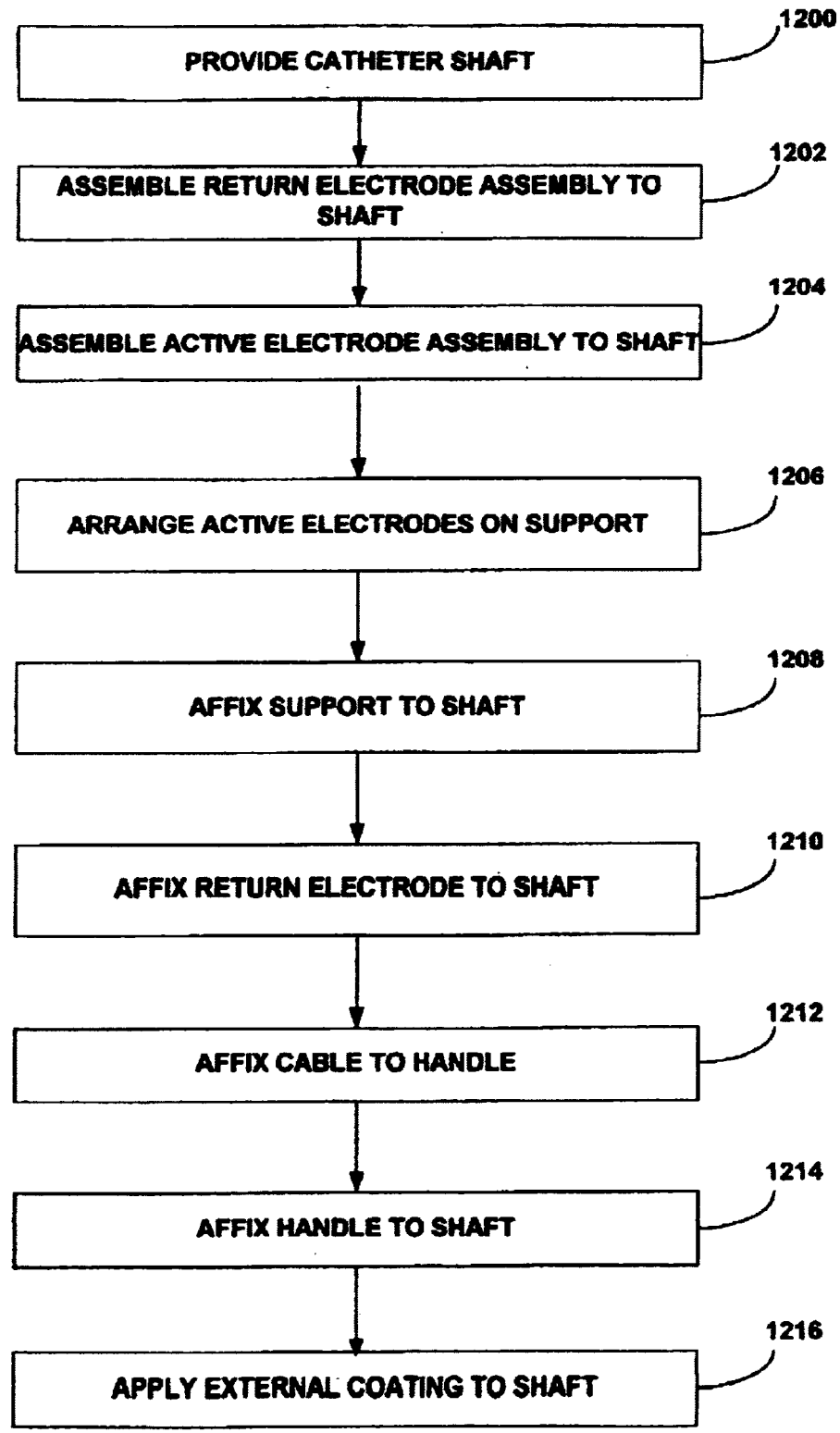
FIG. 42 schematically represents a series of steps involved a method of making an electrosurgical catheter, according to a further embodiment of the invention.

FIG. 42 schematically represents a series of steps involved a method of making an electrosurgical catheter, according to a further embodiment of the invention, wherein step 1200 involves providing a catheter shaft. Typically, step 1200 involves providing a length of a tubular flexible polymeric material, such as a polyether block amide (PEBAX). The diameter and length of the shaft is to some extent a matter of design choice, and is dependent, inter alia, on the intended purpose of the catheter. In the case of catheters designed for coronary artery angioplasty procedures, the shaft provided in step 1200 typically has a length in the range of from about 120 to 150 cm, and more typically about 130 to 140 cm. In certain embodiments wherein the catheter includes an external fluid delivery sheath, the shaft is ensheathed within an external sheath, the latter typically comprising a suitable length of a tubular flexible polymeric material such as PEBAX 63D, and having an internal diameter greater than the external diameter of the shaft. The external sheath may be either fixed (e.g., FIG. 27), or moveable (FIGS. 28A, 28B). In the former case, after the shaft has been ensheathed within the external sheath, the external sheath is affixed to the shaft, for example the external sheath may be bonded to the shaft at the shaft distal end portion proximal to the return electrode.

Step 1202 involves assembling a return electrode assembly to the shaft, wherein the return electrode assembly includes a return electrode coupled to a return electrode lead. The return electrode may comprise an annular band comprising platinum, tantalum or alloys, e.g., a Pt/Ir, Pt/Ta or Pt/Mo alloy. The return electrode lead may comprise a first length of insulated wire comprising platinum or Pt/Ir, coupled to a second length of insulated wire comprising molybdenum, essentially as described hereinabove for the active electrode/active electrode lead with reference to FIG. 32 (pure or clad wire). The return electrode may be coupled to the return electrode lead by spot welding, or other techniques well known in the art. A return electrode in the form of an annular band may be assembled to the shaft on an insulating liner (FIG. 32) comprising an electrically insulating material, such as a polyimide.

Step 1204 involves assembling an active electrode assembly to the shaft. In one embodiment, the active electrode assembly includes a hybrid active electrode lead comprising a first wire of a first composition, and a second wire of a second composition, essentially as described with reference to FIG. 32. However, in contrast to the active electrode/active electrode lead depicted in FIG. 32, in a currently preferred embodiment the steps of removing the insulation from a portion of the electrode lead and bending the electrode terminal to form the loop portion are performed after step 1204. In one embodiment, the guidewire lumen may also be assembled into the shaft after step 1204. Typically, the guidewire lumen comprises a synthetic polymer, such as polyethylene. In one embodiment, the proximal end of the active electrode leads and of the return electrode lead are coupled to a cable connector at the proximal end of the catheter.

After step 1204, a suitable length of electrical insulation may be removed from the distal portion of the active electrode lead. Thereafter, step 1206 involves arranging the active electrodes on the distal portion of the electrode support. Typically, the electrical insulation is removed from the active electrode lead over a length ranging from about 6 mm to about 18 mm to expose the active electrode terminal. In one embodiment, the active electrodes may be arranged on the electrode support by forcing the active electrode terminal through a pliable electrode support, e.g., an electrode support comprising silicone rubber. Thereafter, the distal portion of the active electrode terminal protruding from the distal end of the electrode support may be bent to form a loop portion and a free end, the former exposed on the external surface of the electrode support, and the latter buried within the electrode support (e.g., FIGS. 37A–C). In an alternative embodiment, after the active electrode terminal has been exposed by removing a length of electrical insulation from the active electrode lead, the active electrode terminal may be bent to provide a loop portion and a free end, and the active electrodes may be arranged within the electrode support by molding the electrode support around the active electrode terminal such that the loop portion is exposed on the surface of the electrode support.

Typically, step 1206 involves arranging the active electrodes on the electrode support such that a gap ($H_{gap}$, e.g., FIG. 37A) exists between the loop portion and the surface of the electrode support. According to certain embodiments, the loop portion of the active electrodes are recessed to some extent within the electrode support. In the case of recessed active electrodes, a gap may be achieved by accommodating the loop portion within an electrode socket within the electrode support (FIG. 37B). Step 1208 involves affixing the electrode support to the shaft distal end. Step 1210 involves affixing the return electrode to the shaft. The electrode support and the return electrode may both be affixed to the shaft with a suitable bonding agent, such as Loctite 4981 (Loctite Corporation, Rocky Hill, Conn.). In certain embodiments, the catheter includes an integral catheter cable for coupling the active and return electrodes to a power supply. Step 1202 involves affixing the catheter cable to the handle or proximal portion of the catheter. Typically, the catheter cable is connected to the handle via a cable connector (e.g., FIGS. 30, 31A). Step 1214 involves affixing the handle to the shaft proximal end. Typically, step 1214 involves coupling the shaft to the handle via one or more strain relief units. The strain relief unit(s) typically comprise polyethylene or other synthetic polymer, and serve to prevent distortion or kinking of the shaft proximal end portion at its point of attachment to the handle. In a further step (not shown in FIG. 42) an external coating may be applied to the distal portion of the shaft and electrode support, step 1216. The external coating may be applied to the distal portion of the shaft by a dipping process. The external coating serves to promote lubricity of the shaft distal end and electrode support, and to facilitate guiding the catheter to a target site. The external coating is generally absent from the return electrode and from the active electrodes. An exemplary material for applying to the catheter distal end as an external coating is polyvinylpyrrolidone (PVP) (available from Sigma-Aldrich), or can be contracted from SurModics or STS Biopolymers.

During the percutaneous introduction and removal of the catheter shaft, various measures may be taken to prevent iatrogenic injury to the walls of the body lumen or passage as well as to the other tissues encountered along the pathway to the target site. In one embodiment, catheter 600 includes a compliant, atraumatic safety sheath (not shown) which extends over at least the distal end of the catheter. In use, the sheath is advanced forward during introduction of the catheter shaft to the target site or occlusion. Once the target site has been accessed, the compliant, atraumatic safety sheath is retracted (e.g., by a distance of 1.5 to 2.0 cm) to expose the active electrode(s). The safety sheath is preferably constructed using thin-walled plastic tubing selected to provide bio-compatibility, compliance and low friction during insertion and removal. A number of plastic materials are available for this purpose and include Teflon, polypropylene and polyvinyl chloride. The activation mechanism for advancing and retracting the safety sheath may be either (1) the thin-walled plastic tubing is moved relative to the catheter body at a location external to the patient's body, or (2) a drive rod or wire (not shown) within the catheter body is used to actuate a short segment of the safety sheath (e.g., a length of 4 to 8 cm) located at the distal end of the catheter body.

Typically, the platinum-iridium electrodes of the invention comprise up to about 30%, and preferably between 5% and 15%, of iridium to mechanically strengthen the electrodes. Applicants have found that platinum or platinum/iridium electrodes provide more efficient ionization of the conductive fluid, less thermal heating of surrounding tissue, and overall superior ablation. Because platinum has a low thermal conductivity and low resistivity, heat production is minimized and there is a more efficient transfer of energy into the electrically conductive fluid to create the plasma. As an additional benefit, Applicants have found that platinum/platinum-iridium electrodes have superior anti-corrosion properties and anti-oxidation properties in the presence of the electrically conductive fluid as compared with other electrode materials. Other possibilities include Tantalum and the following clads: Pt/Ta, Pt/Mo, Pt/W and Pt/Ag.

While the exemplary embodiments of the present invention have been described in detail, by way of example and for clarity of understanding, a variety of changes, adaptations, and modifications will be obvious to those of skill in the art. For example, each of the embodiments can be used with a power limiting device 300 and/or a spark limiting device 330. Additionally, any of the above described embodiments can comprise an electrode support having a larger outer diameter than the diameter of the shaft. Moreover, while not illustrated, each of the above described apparatus can be used with a rapid-exchange catheter. Therefore, the scope of the present invention is limited solely by the appended claims.

What is claimed is:

1. An electrosurgical catheter, comprising:
   a shaft having a shaft proximal end portion and a shaft distal end portion;
   an electrode support arranged on the shaft distal end portion, the electrode support having a support distal end;
   at least one active electrode disposed on the support distal end, wherein the at least one active electrode comprises a metal wire comprising from about 75% to about 99.95% platinum and from about 0.05% to about 25% iridium; and
   at least one return electrode disposed on the shaft distal end portion and wherein the at least one return electrode is arranged on an insulating liner, and the insulating liner is disposed on the shaft.

2. The electrosurgical catheter of claim 1, wherein the insulating liner comprises a polyimide.

3. The electrosurgical catheter of claim 1, wherein the at least one active electrode comprises a loop portion consisting essentially of an alloy of platinum and iridium.

4. The electrosurgical catheter of claim 1, wherein the at least one active electrode comprises a plurality of active electrodes, each of the plurality of active electrodes is in communication with a corresponding one of a plurality of active electrode leads, each of the plurality of active electrode leads comprises a wire having a diameter in the range of from about 0.002" to about 0.008", and the wire comprises an alloy of platinum and iridium.

5. The electrosurgical catheter of claim 1, wherein the at least one active electrode is in communication with an active electrode lead, the active electrode lead comprising a distal active electrode lead portion and a proximal active electrode lead portion coupled to the distal active electrode lead portion, wherein the distal active electrode lead comprises from about 75% to about 99.95% platinum and from about 0.05% to about 25% iridium.

6. The electrosurgical catheter of claim 5, wherein the proximal active electrode lead portion comprises at least 50% molybdenum.

7. An electrosurgical catheter, comprising:
   a shaft having a shaft proximal end portion and a shaft distal end portion;
   an electrode support arranged on the shaft distal end portion, the electrode support having a support distal end, a support proximal end, and a belly portion located between the support distal end and the support proximal end, wherein the width of the belly portion is greater than the width of the shaft;
   at least one active electrode disposed on the electrode support; and
   at least one return electrode disposed on the shaft distal end portion at a location proximal to the electrode support.

8. The electrosurgical catheter of claim 7, wherein the shaft comprises a material selected from the group consisting essentially of a polyether-based polyamide, polyurethane, polyethylene and nylon.

9. The electrosurgical catheter of claim 7, wherein the electrode support comprises a material selected from the group consisting of: a ceramic, a glass, polytetrafluoroethylene, urethane, a polyurethane, a polyimide, and a silicone rubber.

10. The electrosurgical catheter of claim 7, wherein the electrode support tapers from narrow to broad from the support distal end to the belly portion.

11. The electrosurgical catheter of claim 10, wherein the electrode support tapers from broad to narrow from the belly portion to the support proximal end.

12. The electrosurgical catheter of claim 10, wherein the electrode support comprises a silicone rubber.

13. The electrosurgical catheter of claim 7, further comprising at least one lumen extending along the shaft.

14. An electrosurgical catheter, comprising:
   a shaft having a shaft proximal end portion and a shaft distal end portion;
   an electrode support arranged on the shaft distal end portion, the electrode support having a support distal end, a support proximal end, and a belly portion located between the support distal end and the support proximal end;
   at least one active electrode disposed on the electrode support, wherein the at least one active electrode is located distal to the belly portion; and
   a return electrode disposed on the shaft distal end portion proximal to the electrode support, the return electrode in communication with a return electrode lead
   and wherein each of the at least one active electrodes comprises a metal wire, and the metal wire comprises a material selected from the group consisting of platinum, indium, molybdenum, titanium, aluminum, nickel, tungsten, and tantalum.

15. The electrosurgical catheter of claim 14, wherein the at least one active electrode comprises a plurality of active electrodes, and each of the plurality of active electrodes comprises a loop electrode.

16. The electrosurgical catheter of claim 15, wherein each of the loop electrodes comprises a first free end, a loop portion, and a second connected end.

17. The electrosurgical catheter of claim 16, wherein each of the second connected ends is in communication with a distal active electrode lead.

18. The electrosurgical catheter of claim 17, further comprising at least one proximal active electrode lead, each of the at least one proximal active electrode leads in communication with a corresponding one of the distal active electrode leads.

19. The electrosurgical catheter of claim 17, wherein each of the loop electrodes and each of the distal active electrode leads consists essentially of platinum.

20. The electrosurgical catheter of claim 17, wherein each of the loop electrodes and each of the distal active electrode leads consist essentially of a platinum-iridium alloy.

21. The electrosurgical catheter of claim 17, wherein each of the loop electrodes and each of the distal active electrode leads comprise from about 75% to about 99.95% platinum and from about 0.05% to about 25% iridium.

22. The electrosurgical catheter of claim 14, wherein each of the at least one active electrodes comprises a metal wire having a diameter in the range of from about 0.002" to about 0.020".

23. The electrosurgical catheter of claim 14, wherein each of the at least one active electrodes includes a loop portion comprising a metal wire having a cross-sectional shape selected from the group consisting of substantially round, substantially square, and substantially triangular.

24. The electrosurgical catheter of claim 14, wherein each of the at least one active electrodes includes a loop portion comprising a metal wire having a cross-sectional shape including at least one cusp or serration.

25. The electrosurgical catheter of claim 14, wherein the width of the belly portion is greater than or equal to the width of the shaft.

26. The electrosurgical catheter of claim 14, wherein the support distal end portion is substantially conical in shape.

27. The electrosurgical catheter of claim 14, wherein each of the at least one active electrodes includes a loop portion, and the loop portion is curved.

28. The electrosurgical catheter of claim 14, wherein the return electrode comprises an annular band of a metal.

29. The electrosurgical catheter of claim 28, wherein the return electrode consists essentially of platinum.

30. The electrosurgical catheter of claim 28, wherein the return electrode consists essentially of a platinum-iridium alloy.

31. The electrosurgical catheter of claim 14, wherein the return electrode comprises from about 75% to about 99.95% platinum and from about 0.05% to about 25% iridium.

32. The electrosurgical catheter of claim 14, wherein the shaft is at least substantially rigid and has a length in the range of from about 120 cm to about 140 cm.

33. The electrosurgical catheter of claim 14, wherein the shaft is flexible and has a length in the range of from about 120 cm to about 150 cm.

34. The electrosurgical catheter of claim 14, wherein an external surface of the shaft distal end has an external hydrophilic coating.

35. The electrosurgical catheter of claim 14, wherein the return electrode comprises notches to increase a surface area of the return electrode.

36. The electrosurgical catheter of claim 14, wherein the return electrode comprises a pitch coil to minimize current induction.

* * * * *